US012753437B2

(12) United States Patent
Yoseph et al.

(10) Patent No.: US 12,753,437 B2
(45) Date of Patent: Oct. 6, 2026

(54) METHODS OF ISOLATING T CELLS AND T-CELL RECEPTORS FROM PERIPHERAL BLOOD BY SINGLE-CELL ANALYSIS FOR IMMUNOTHERAPY

(71) Applicant: The United States of America, as represented by the Secretary, Department of Health and Human Services, Bethesda, MD (US)

(72) Inventors: Rami Yoseph, Gaithersburg, MD (US); Amy R. Copeland, Washington, DC (US); Sri Krishna, North Bethesda, MD (US); Frank J. Lowery, III, Clarksburg, MD (US); Steven A. Rosenberg, Potomac, MD (US); Paul F. Robbins, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 965 days.

(21) Appl. No.: 17/906,524

(22) PCT Filed: Mar. 19, 2021

(86) PCT No.: PCT/US2021/023225

§ 371 (c)(1),
(2) Date: Sep. 16, 2022

(87) PCT Pub. No.: WO2021/188941

PCT Pub. Date: Sep. 23, 2021

(65) Prior Publication Data

US 2023/0183802 A1 Jun. 15, 2023

Related U.S. Application Data

(60) Provisional application No. 62/992,715, filed on Mar. 20, 2020.

(51) Int. Cl.

| | |
|---|---|
| ***C12Q 1/6881*** | (2018.01) |
| ***A61K 40/11*** | (2025.01) |
| ***A61K 40/32*** | (2025.01) |
| ***A61K 40/42*** | (2025.01) |
| ***A61K 40/46*** | (2025.01) |
| ***C12N 5/078*** | (2010.01) |
| ***C12N 5/0783*** | (2010.01) |
| ***C12Q 1/6869*** | (2018.01) |

(52) U.S. Cl.

CPC ............ *C12Q 1/6881* (2013.01); *A61K 40/11* (2025.01); *A61K 40/32* (2025.01); *A61K 40/4201* (2025.01); *A61K 40/46* (2025.01); *C12N 5/0634* (2013.01); *C12N 5/0636* (2013.01); *C12Q 1/6869* (2013.01); *C12Q 2600/158* (2013.01)

(58) Field of Classification Search

None

See application file for complete search history.

(56) References Cited

U.S. PATENT DOCUMENTS

| | | | | |
|---|---|---|---|---|
| 8,034,334 | B2 | 10/2011 | Dudley et al. | |
| 8,383,099 | B2 | 2/2013 | Dudley et al. | |
| 10,716,809 | B2 * | 7/2020 | Gros | A61K 40/11 |
| 11,629,334 | B2 * | 4/2023 | Gros | C12N 5/0636 514/19.3 |
| 2012/0244133 | A1 | 9/2012 | Rosenberg et al. | |
| 2017/0218042 | A1 | 8/2017 | Tran et al. | |
| 2017/0224800 | A1 | 8/2017 | Tran et al. | |
| 2020/0056237 | A1 | 2/2020 | Lu et al. | |

FOREIGN PATENT DOCUMENTS

| | | | | |
|---|---|---|---|---|
| WO | WO 2016/100977 | A1 | 6/2016 | |
| WO | WO 2016/179006 | A1 | 11/2016 | |
| WO | WO-2017048614 | A1 * | 3/2017 | G01N 33/5094 |
| WO | WO 2019/100001 | A1 | 5/2019 | |
| WO | WO 2019/112932 | A1 | 6/2019 | |
| WO | WO 2019/204338 | A1 | 10/2019 | |

OTHER PUBLICATIONS

Zhong. Expression of PD-1 by CD4+CD25+CD127low Treg cells in the peripheral blood of lung cancer. Onco Targets Ther; 8:1831-1833. (Year: 2015).*

Cillo. immune Landscape of Viral- and Carcinogen-Driven Head and Neck Cancer. Immunity; 52:183-199. (Year: 2020).*

Pauken. Single-cell analyses identify circulating anti-tumor CD8 T cells and markers for their enrichment. J Exp Med; 218(4):1-31. (Year: 2021).*

Lu. Single-Cell Transcriptome Analysis Reveals Gene Signatures Associated with T-cell Persistence Following Adoptive Cell Therapy. Cancer Immunol Res; 7(11): 1824-1836. (Year: 2019).*

Hanada et al., "A phenotypic signature that identifies neoantigen-reactive T cells in fresh human lung cancer", Cancer Cell, 40: 479-493 (2022).

Hanada et al., Supplemental Information for "A phenotypic signature that identifies neoantigen-reactive T cells in fresh human lung cancer", Cancer Cell, 40: 479-493 (2022), 205 pages.

(Continued)

*Primary Examiner* — Maureen Varina Driscoll

(74) *Attorney, Agent, or Firm* — Leydig, Voit & Mayer

(57) ABSTRACT

Provided are methods of preparing an enriched population of T cells having antigenic specificity for a target antigen. The method may comprise isolating T cells from a blood sample of a patient; selecting the isolated T cells which have a gene expression profile; and separating the selected T cells from the unselected cells. The separated selected T cells provide an enriched population of T cells having antigenic specificity for the target antigen. Methods of isolating a TCR, preparing a population of cells that express a TCR, isolated TCRs, isolated populations of cells, pharmaceutical compositions, and methods of treating or preventing a condition in a mammal are also provided.

20 Claims, 24 Drawing Sheets

(56) References Cited

OTHER PUBLICATIONS

Lowery et al., Supplementary Materials for "Molecular signatures of antitumor neoantigen-reactive T cells from metastatic human cancers", Science, 375(6583): 877-884 (2022), 313 pages.
Yossef et al., "Phenotypic signatures of circulating neoantigen-reactive CD8+ T cells in patients with metastatic cancers", Cancer Cell, 41: 2154-2165 (2023).
Yossef et al., Supplemental Information for "Phenotypic signatures of circulating neoantigen-reactive CD8+ T cells in patients with metastatic cancers", Cancer Cell, 41: 2154-2165 (2023), 1,557 pages.
Duhen et al., "Co-expression of CD39 and CD103 identifies tumor-reactive CD8 T cells in human solid tumors", *Nature Communications*, 9:2724, pp. 1-13 (2018).
Fehlings et al., "Late-differentiated effector neoantigen-specific CD8+ T cells are enriched in peripheral blood of non-small cell lung carcinoma patients responding to atezolizumab treatment", *Journal for ImmunoTherapy of Cancer*, 7: 249, pp. 1-15 (2019).
International Searching Authority, International Search Report and Written Opinion issued in International Patent Application No. PCT/US2021/023225, mailed on Jun. 29, 2021.
Cafri et al., "Memory T cells targeting oncogenic mutations detected in peripheral blood of epithelial cancer patients", *Nature Communications*, vol. 10, pp. 1-9 (2019).
Cohen et al., "Isolation of neoantigen-specific T cells from tumor and peripheral lymphocytes", *Journal of Clinical Investigation*, vol. 125, Issue 10, pp. 3981-3991 (2015).
Dudley et al., "Generation of Tumor-Infiltrating Lymphocyte Cultures for Use in Adoptive Transfer Therapy for Melanoma Patients", *Journal of Immunotherapy*, vol. 26, Issue 4, pp. 332-342 (2003).
Fuchs et al., "Gene Expression-Based Identification of Antigen-Responsive CD8+ T Cells on a Single-Cell Level", *Frontiers in Immunology*, vol. 10, pp. 2568-2588 (2019).
Garcia-Garijo et al., "Determinants for Neoantigen Identification", *Frontiers in Immunology*, vol. 10, No. 1392, pp. 1-19 (2019).
Goff et al., "Randomized, Prospective Evaluation Comparing Intensity of Lymphodepletion Before Adoptive Transfer of Tumor-Infiltrating Lymphocytes for Patients with Metastatic Melanoma," *Journal of Clinical Oncology*, vol. 34, Issue 20, pp. 2389-2397 (2016).
Gros et al., "Prospective identification of neoantigen-specific lymphocytes in the peripheral blood of melanoma patients", *Nature Medicine*, vol. 22, Issue 4, pp. 433-438 (2016).
Linnemann et al., "High-throughput identification of antigen-specific TCRs by TCR gene capture". *Nature Medicine*, vol. 19, No. 11, pp. 1534-1541 (2013).
Lowery et al., "Molecular signatures of antitumor neoantigen-reactive T cells from metastatic human cancers", *Science*, vol. 375, No. 6583, pp. 877-884 (2022).
Riddell et al., "The use of anti-SD3 and anti-CD28 monoclonal antibodies to clone and expand human antigen-specific T-cells", *Journal of Immunological Methods*. vol. 128, No. 2 189-201 (1990).
Stoeckius et al., "Simultaneous epitope and transcriptome measurement in single cells", *Nature Methods*, vol. 14, Issue 9, pp. 865-868 (2017).
Tran et al., "T-cell therapy against cancer mutations", *Oncotarget*, vol. 5, Issue 13, pp. 4579-4580 (2014).
Van Der Leun et al., "CD8T cell states in human cancer: insights from single-cell analysis", *Nature Reviews Cancer*, vol. 20, No. 4, pp. 218-232 (2020).
Van Der Maaten et al., "Visualizing Data using t-SNE", *Machine Learning Research*, vol. 9, pp. 2579-2605 (2008).
Kato et al. "Effective screening of T cells recognizing neoantigens and construction of T-cell receptor-engineered T cells." Oncotarget, 9(13):11009-11019. (2018).

* cited by examiner

90th NeoBlood Signature

METHODS OF ISOLATING T CELLS AND T-CELL RECEPTORS FROM PERIPHERAL BLOOD BY SINGLE-CELL ANALYSIS FOR IMMUNOTHERAPY

CROSS-REFERENCE TO RELATED APPLICATIONS

This patent application is the U.S. national stage of PCT/US2021/23225, filed Mar. 19, 2021, which claims the benefit of U.S. Provisional Patent Application No. 62/992,715, filed Mar. 20, 2020, each of which is incorporated by reference in its entirety herein.

STATEMENT REGARDING FEDERALLY SPONSORED RESEARCH OR DEVELOPMENT

This invention was made with Government support under project number ZIA BC 010984 by the National Institutes of Health, National Cancer Institute. The Government has certain rights in the invention.

BACKGROUND OF THE INVENTION

Adoptive cell therapy (ACT) using T cells that target a neoantigen encoded by the cancer-specific mutation can produce positive clinical responses in some patients. Nevertheless, several obstacles to the successful use of ACT for the treatment of cancer and other conditions remain. For example, the current methods used to produce cancer-reactive T cells require significant time and may not readily identify the desired T cell receptors that bind cancer targets. Accordingly, there is a need for improved methods of obtaining an isolated population of cells for ACT.

BRIEF SUMMARY OF THE INVENTION

An aspect of the invention provides a method of preparing an enriched population of T cells having antigenic specificity for a target antigen, the method comprising: isolating T cells from a blood sample of a patient; selecting the isolated T cells which have a gene expression profile; and separating the selected T cells from the unselected cells, wherein the separated selected T cells provide an enriched population of T cells having antigenic specificity for the target antigen, wherein the target antigen is a neoantigen encoded by a cancer-specific mutation, a cancer antigen, or a cancer-associated viral antigen, and the gene expression profile comprises: (a) one or more of ACTG1$^+$, AES$^+$, ANXA2$^+$, ANXA5$^+$, ARPC2$^+$, ARPC3$^+$, CD3D$^+$, CD52$^+$, CD7$^+$, CD62L$^+$, CD99$^+$, CORO1A$^+$, COTL1$^+$, CRIP1$^+$, CXCL13$^+$, EMP3$^+$, FLNA$^+$, FTL$^+$, FYB1$^+$, GAPDH$^+$, H2AFV$^+$, HMGB2$^+$, IL32$^+$, ITGB1$^+$, LSP1$^+$, LTB$^+$, PPIA$^+$, S100A10$^+$, S100A4$^+$, S100A6$^+$, SLC25A5$^+$, TIGIT$^+$, TMSB10$^+$, VIM$^+$, ACTB$^-$, B2M$^-$, BTG1$^-$, CCL4$^-$, CCL4L2$^-$, CCL5$^-$, CD74$^-$, EEF1A1$^-$, FTH1$^-$, GZMK$^-$, HLA-DRA$^-$, MTRNR2L12$^-$, PNRC1$^-$, RPL10$^-$, RPL13$^-$, RPL3$^-$, RPL30$^-$, RPL32$^-$, RPL34$^-$, RPLP1$^-$, RPL39$^-$, RPL5$^-$, RPLP0$^-$, RPS12$^-$, RPS14$^-$, RPS18$^-$, RPS19$^-$, RPS21$^-$, RPS23$^-$, RPS24$^-$, RPS3$^-$, RPS3A$^-$, RPS4X$^-$, RPS6$^-$, and ZC3HAV1$^-$; (b) one or more of CARS$^+$, CD39$^+$ (ENTPD1)$^+$, CD62L$^+$, CD70$^+$, CD82$^+$, CTLA4$^+$, CXCL13$^+$, HLA-DRA$^+$, HLA-DRB1$^+$, ITAGE$^+$, LAG3$^+$, LGALS3$^+$, PDCD1$^+$, SA100A4$^+$, TIGIT$^+$, and TOX$^+$; (c) CD8$^+$ and one or more of ALOX5AP$^+$, ANXA2$^+$, ANXA5$^+$, CARS$^+$, CD82$^+$, CDC25B$^+$, CHN1$^+$, CLECL1$^+$, COTL1$^+$, CYTOR$^+$, FLNA$^+$, GATA3$^+$, HLA-DPA1$^+$, HLA-DQA2$^+$, HLA-DQB1$^+$, HLA-DRA$^+$, HLA-DRB1$^+$, HLA-DRB5$^+$, ITGB1$^+$, ITM2A$^+$, LGALS3$^+$, MYO1G$^+$, P2RY8$^+$, PASK$^+$, RBPJ$^+$, S100A11$^+$, TPM4$^+$, TRADD$^+$, UBXN11$^+$, CCL4$^-$, CCL5$^-$, CCR7$^-$, CYTIP$^-$, EEF1G$^-$, GZMH$^-$, IMPDH2$^-$, LINC02446$^-$, LYAR$^-$, MYC$^-$, NKG7$^-$, NUCB2$^-$, PITPNC1$^-$, PLAC8$^-$, and TCF7$^-$; (d) CD8$^+$ and one or more of ALOX5AP$^+$, ANXA2$^+$, ANXA5$^+$, CARS$^+$, CD82$^+$, CDC25B$^+$, CHN1$^+$, CLECL1$^+$, COTL1$^+$, FLNA$^+$, HLA-DPA1$^+$, HLA-DQA2$^+$, HLA-DQB1$^+$, HLA-DRA$^+$, HLA-DRB1$^+$, HLA-DRB5$^+$, ITGB1$^+$, ITM2A$^+$, LGALS3$^+$, MYO1G$^+$, PASK$^+$, S100A11$^+$, TIGIT$^+$, and UBXN11$^+$; (e) CD8$^+$ and one or more of CD45RO$^+$, CD45RA$^-$, HLA-DR$^+$, CD39$^+$, and CD103$^+$; (f) CD8$^+$ and one or more of CD45RO$^+$, CD45RA$^-$, HLA-DR$^+$, CD39$^+$, and TIGIT$^+$; (g) CD8$^+$ and one or more of CD45RO$^+$, CD45RA$^-$, HLA-DR$^+$, CD39$^+$, and PD-1$^+$; (h) CD4$^+$ and one or more of CD45RO$^+$, CD45RA$^-$, HLA-DR$^+$, and CD39$^+$; (i) CD4$^+$ and one or more of AK4$^+$, APOBEC3G$^+$, C12orf75$^+$, CCL5$^+$, CD74$^+$, COTL1$^+$, CST7$^+$, CXCL13$^+$, CXCR3$^+$, DUSP2$^+$, EEF1A1$^+$, F2R$^+$, GAPDH$^+$, GNLY$^+$, GZMA$^+$, GZMK$^+$, HCST$^+$, HLA-DPA1$^+$, LYAR$^+$, LYST$^+$, MRPL10$^+$, MYO1G$^+$, NKG7$^+$, PABPC1$^+$, PDCD1$^+$, PFN1$^+$, PRF1$^+$, RAB27A+, RPL10$^+$, RPL11$^+$, RPL13$^+$, RPL18A+, RPL19$^+$, RPL30$^+$, RPL32$^+$, RPL34$^+$, RPL8$^+$, RPL9$^+$, RPLP1$^+$, RPS12$^+$, RPS13$^+$, RPS23$^+$, RPS3A$^+$, RPS8$^+$, SARAF$^+$, SELL$^+$, TC2N$^+$, TMSB4X$^+$, and TPT1$^+$; (j) CD4$^+$ and one or more of AC004585.1$^+$, ACM ACTG1$^+$, ALOX5AP$^+$, ANXA1$^+$, ANXA5$^+$, CD52$^+$, CD99$^+$, CNN2$^+$, COTL1$^+$, FAM45A$^+$, FTH1$^+$, FYB1$^+$, GAPDH$^+$, GIMAP4$^+$, GYPC$^+$, IFITM1$^+$, IFITM2$^+$, IGFBP4$^+$, ITGB1$^+$, LCP1$^+$, LIMS1$^+$, LMO4$^+$, MALAT1$^+$, MIF$^F$, MSN$^+$, MT-ND3$^+$, NDUFA12$^+$, PASK$^+$, PFN1$^+$, PGAM1$^+$, PPP2R5C$^+$, RARRES3$^+$, RILPL2$^+$, RPL30$^+$, RPL32$^+$, RPL34$^+$, RPL9$^+$, RPS13$^+$, RPS25$^+$, RPS3A$^+$, S100A11$^+$, S1PR4$^+$, SERF2$^+$, SLC25A5$^+$, SMC4$^+$, TIMP1$^+$, TMSB4X$^+$, VDAC1$^+$, and ZFP36L2$^+$; (k) one or more of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, H1FX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IF127L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1$^+$, MYO1G$^+$, NCK2$^+$, NDUFA7$^+$, NFATC2$^+$, OPTN+, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TLN1$^+$, TMC8$^+$, TMX4$^+$, TOX$^+$, TPM4$^+$, TRAPPC5$^+$, TXN$^+$, UBXN11$^+$, UCP2$^+$, VOPP1$^+$, WNK1$^+$, YWHAE$^+$, and YWHAQ$^+$; (1) one or more of ALOX5AP$^+$, ARID5B$^+$, CCR4$^+$, CD55$^+$, CDKN1B$^+$, COTL1$^+$, CREM$^+$, DCXR$^+$, DGKA$^+$, ELOVL5$^+$, EML4$^+$, EZR$^+$, GATA3$^+$, GPR183$^+$, ICAM2$^+$, IL7R$^+$, ISG20$^+$, ITGB1$^+$, ITM2A$^+$, LEF1$^+$, LEPROTL1$^+$, LTB$^+$, NR3C1$^+$, P2RY10$^+$, PASK$^+$, PLP2$^+$, PPP2R5C$^+$, PRKX$^+$, RALA$^+$, RASA3$^+$, RCAN3$^+$, RHBDD2$^+$, RNASET2$^+$, S100A11$^+$, S1PR1$^+$, S1PR4$^+$, SAMHD1$^+$, SAMSN1$^+$, SELL$^+$, SESN3$^+$, SETD2$^+$, SMCHD1$^+$, TMEM123$^+$, TRAT1$^+$, and ZFP36$^+$; (m) one or more of ALOX5AP$^+$, ANXA2$^+$, ANXA5$^+$, ARID5B$^+$, CAPN2$^+$, CARS$^+$, CDC25B$^+$, CLDND1$^+$, COTL1$^+$, CREM$^+$, CRIP1$^+$, CXCR3$^+$, CYTOR$^+$, DCXR$^+$, EMB$^+$, FBXW5$^+$, FLNA$^+$, GATA3$^+$, HLA-DPA1$^+$, HLA-DPB1$^+$, HLA-DQB1$^+$, HLA-DRA$^+$, HLA-DRB1$^+$, HLA-DRB5$^+$, HNRNPUL1$^+$, ICAM2$^+$, IL10RA$^+$, ISG15$^+$, ISG20$^+$, ITGB1$^+$, ITGB7$^+$, ITM2A$^+$, KLF2$^+$, LGALS3$^+$, MED15$^+$, MX1$^+$, NDUFA12$^+$, NR3C1$^+$, NSMCE1$^+$, P2RY8$^+$, PASK$^+$, PPP2R5C+, RHBDD2$^+$, RNASET2$^+$, S100A11$^+$, S1PR4$^+$, SAMHD1$^+$, SAMSN1$^+$, SELPLG$^+$, SMCHD1$^+$, SPN$^+$, TRADD$^+$, and UBXN11$^+$; (n) one or more of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHEL', FLNA$^+$, FYB1$^+$, GATA3$^+$, GNG2$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, and YWHAB$^+$; or (o) one or more of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHE1$^+$, FBXW5$^+$, FLNA$^+$, FYB1$^+$, GATA3$^+$, GNG2$^+$, GSTK1$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, HNRNPUL1$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, NUDT21$^+$, OCIAD2$^+$, OPTN+, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TGFB1$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, YWHAB$^+$, ANKRD12$^-$, APMAP$^-$, CCL4$^-$, CCL5$^-$, CCR7$^-$, CD48$^-$, CD8B$^-$, CXCR4$^-$, CYTIP$^-$, DARS$^-$, EEF1B2$^-$, EEF1G$^-$, GZMH$^-$, HSP90AB1$^-$, IMPDH2$^-$, ISCU$^-$, LBH$^-$, LINC02446$^-$, LYAR$^-$, MGST3$^-$, MT-ND2$^-$, MT-ND5$^-$, MYC$^-$, NDUFV2$^-$, NFKBIA$^-$, NKG7$^-$, NUCB2$^-$, PDCD4$^-$, PITPNC1$^-$, PLAC8$^-$, PRF1$^-$, PRMT2$^-$, RPL17$^-$, RPS17$^-$, SNHG7$^-$, SNHG8$^-$, STK17A$^-$, TCF7$^-$, TOMM7$^-$, WSB1$^-$, and ZFAS1$^-$.

Another aspect of the invention provides a method of isolating a T cell receptor (TCR), or an antigen-binding portion thereof, having antigenic specificity for a target antigen, the method comprising: preparing an enriched population of T cells having antigenic specificity for the target antigen according to any of the methods described herein with respect to other aspects of the invention; sorting the T cells in the enriched population into separate single T cell samples; sequencing TCR complementarity determining regions 3 (CDR3) in one or more of the separate single T cell samples; pairing an alpha chain variable region comprising a CDR3 with a beta chain variable region comprising a CDR3 encoded by the nucleic acid of the separate single T cell samples; introducing a nucleotide sequence encoding the paired alpha chain variable region and beta chain variable region into host cells and expressing the paired alpha chain variable region and beta chain variable region by the host cells; screening the host cells expressing the paired alpha chain variable region and beta chain variable region for antigenic specificity for the target antigen; and selecting the paired alpha chain variable region and beta chain variable region that have antigenic specificity for the target antigen, wherein the TCR, or an antigen-binding portion thereof, having antigenic specificity for the target antigen is isolated.

Still another aspect of the invention provides a method of preparing a population of cells that express a TCR, or an antigen-binding portion thereof, having antigenic specificity for a target antigen, the method comprising: isolating a TCR, or an antigen-binding portion thereof, according to any of the methods described herein with respect to other aspects of the invention, and introducing a nucleotide sequence encoding the isolated TCR, or the antigen-binding portion thereof, into peripheral blood mononuclear cells (PBMC) to obtain cells that express the TCR, or the antigen-binding portion thereof.

Further aspects of the invention provide related TCRs, or antigen-binding portions thereof, isolated populations of cells, and pharmaceutical compositions prepared according to any of the inventive methods.

Additional aspects of the invention provide related methods of treating or preventing a condition in a mammal and related methods of preparing a medicament for the treatment or prevention of the condition in a mammal, wherein the condition is cancer or a viral condition.

BRIEF DESCRIPTION OF THE SEVERAL VIEWS OF THE DRAWING(S)

Figure 4A:
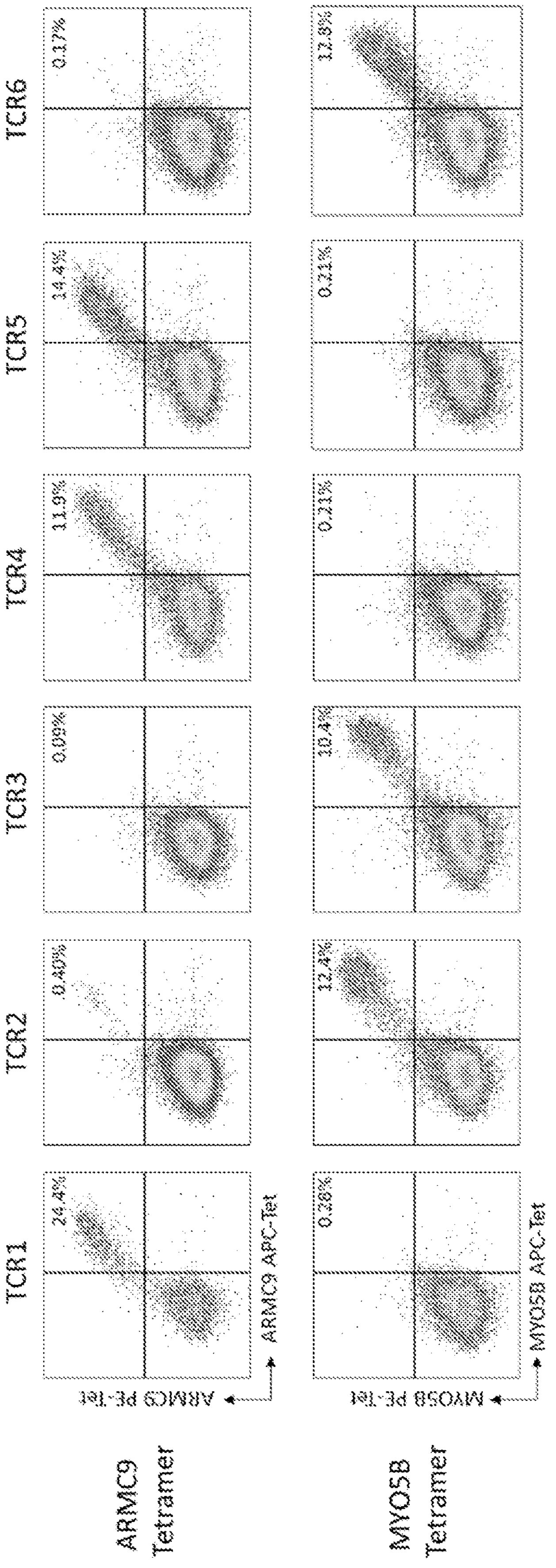
Figure 4B:
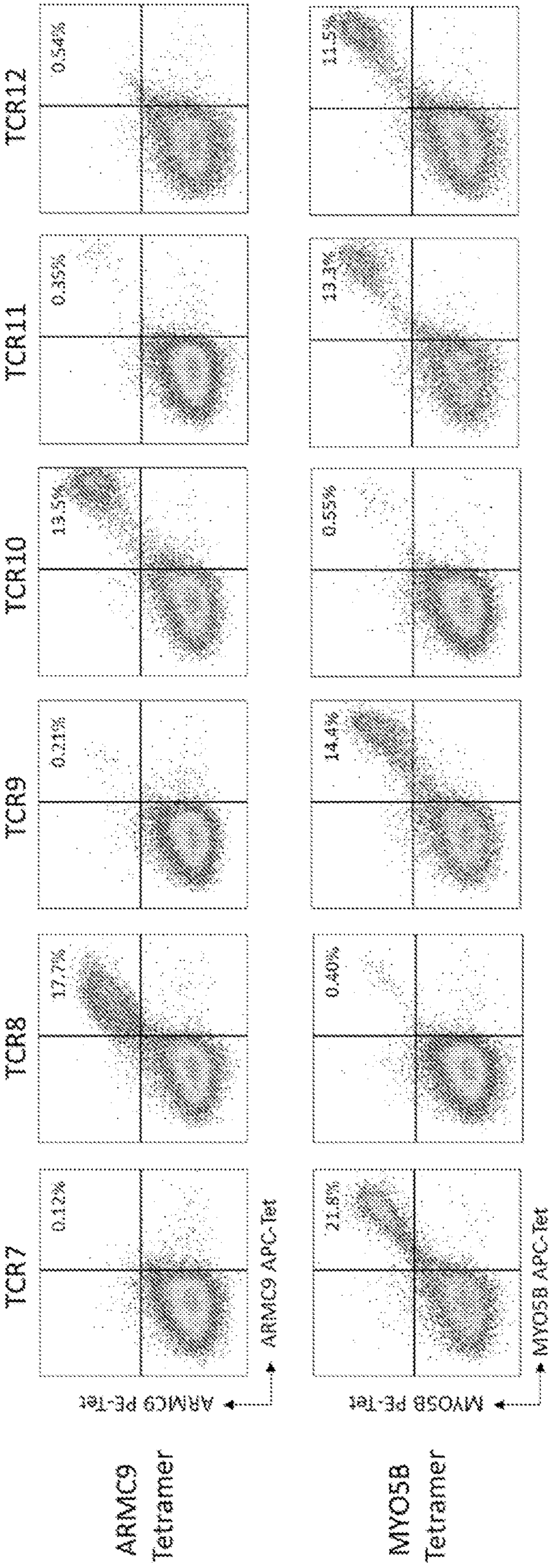
Figure 4C:
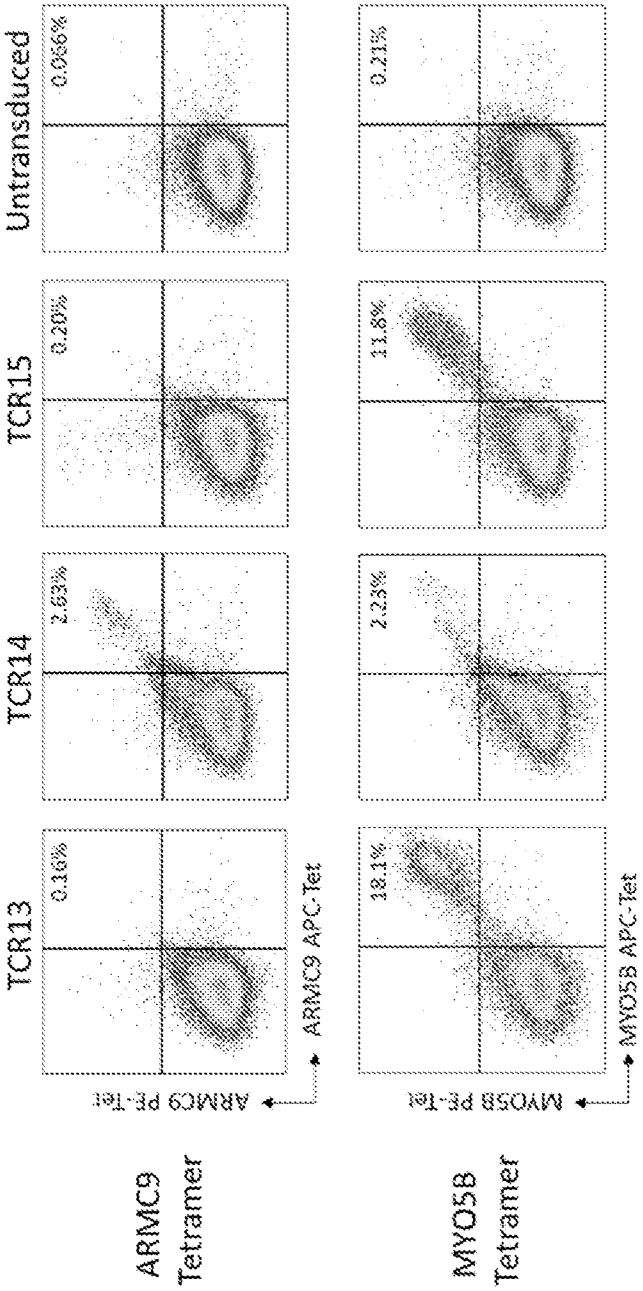

FIGS. 4A-4C show the results of flow cytometric analysis of allogeneic T cells transduced with each one of the top 15 TCRs (TCR1-TCR6 (4A); TCR7-TCR12 (4B); TCR13-TCR14 (4C)) from cluster 4 stained with tetramers of known reactivity (MYO5B or ARMC9). Untransduced cells served as a control (4C). The percentages in the boxes indicate the percentage of transduced cells which bound to the indicated tetramer. PE and APC are the fluorophores that were conjugated to the tetramer (Tet) and used to FACS sort the cells based on their binding.

Figure 2A:
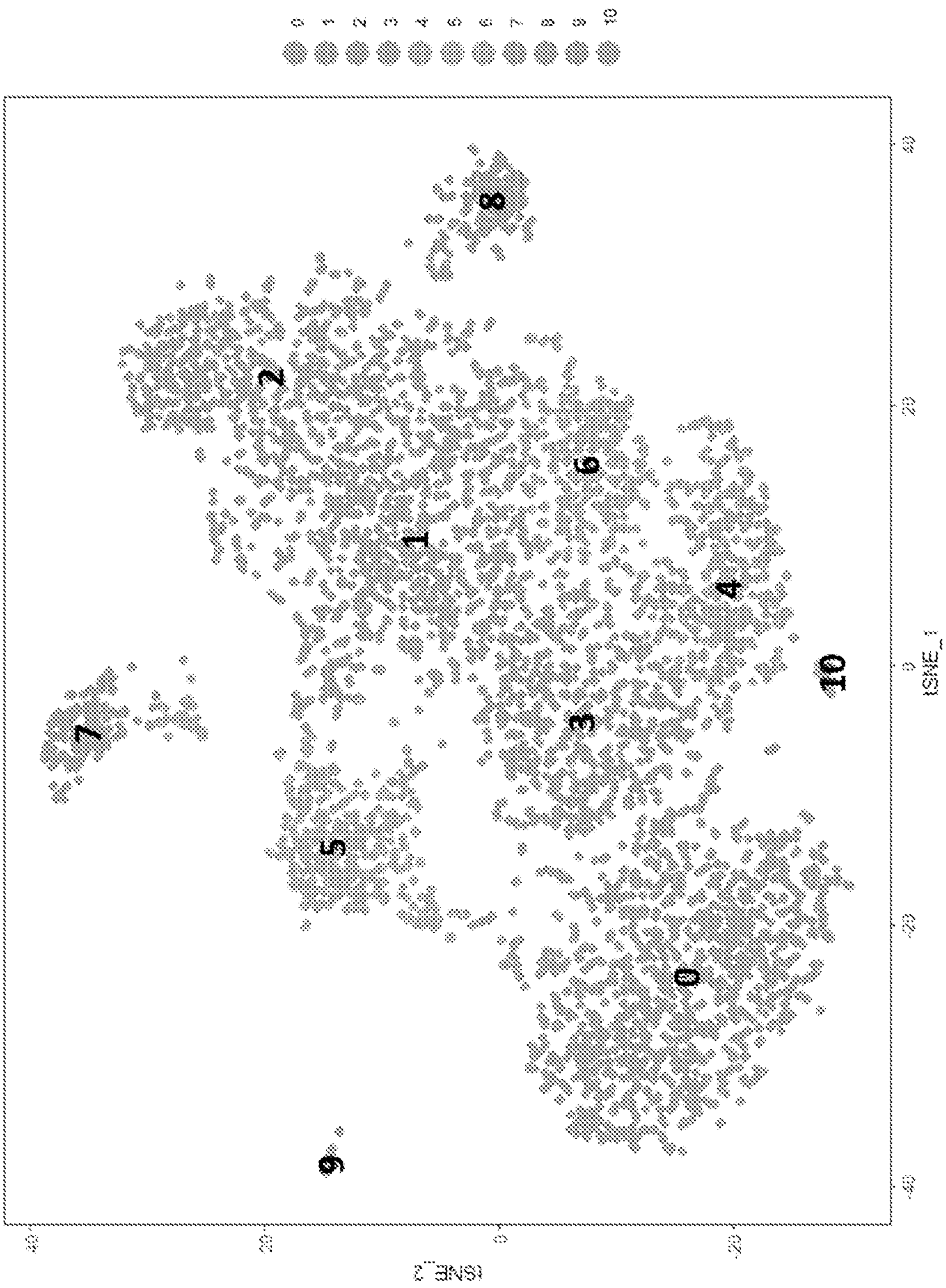
FIG. 2A shows the results of the t-SNE analysis of the single-cell transcriptome of a tetramer-enriched sample from the peripheral blood of colorectal cancer Patient 4246 (t-SNE map). The clusters are numbered 0-10.
Figure 5:
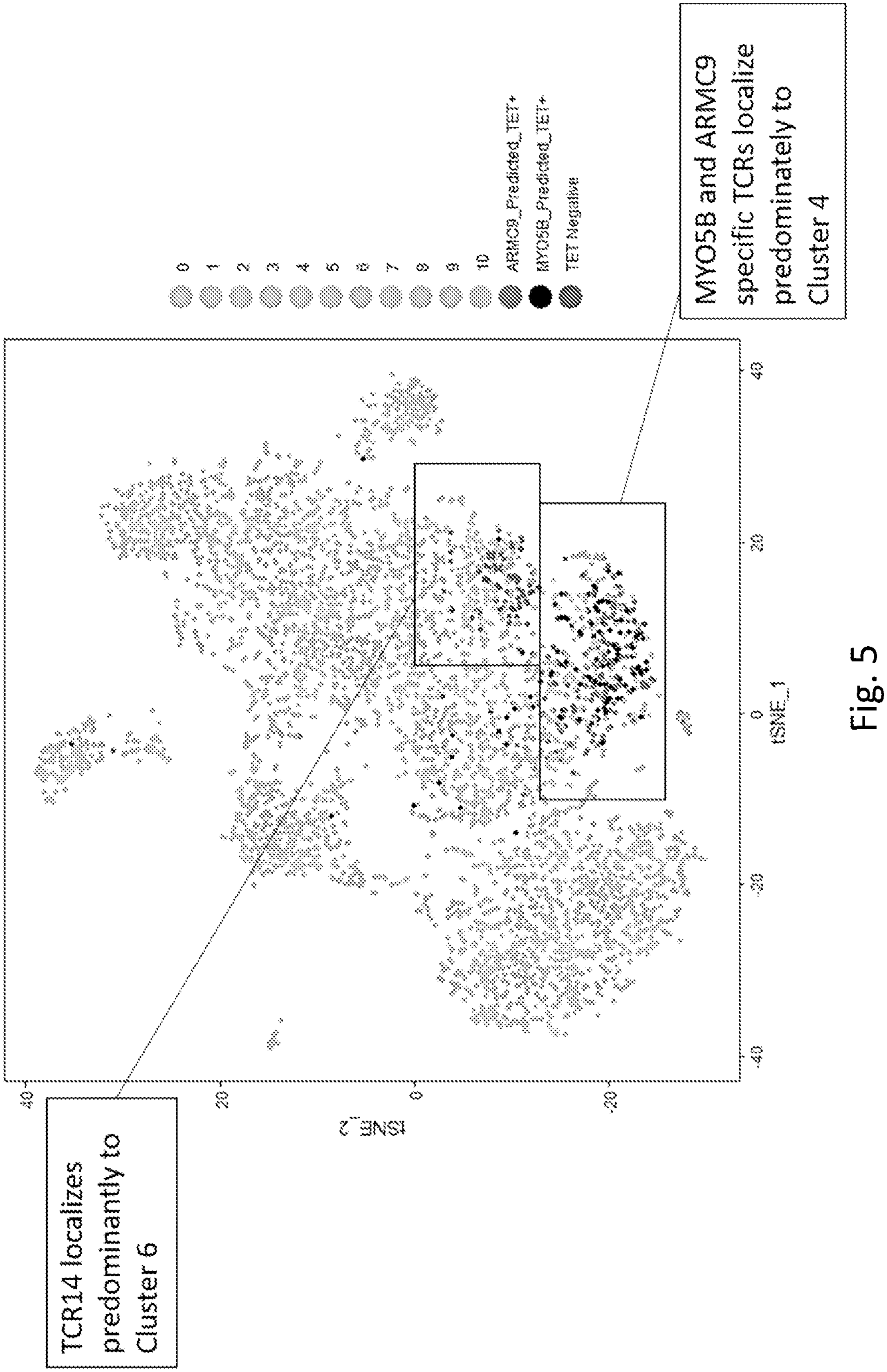

FIG. 5 shows the experimentally tested TCRs projected onto the t-SNE map of FIG. 2A. MYO5B-specific TCRs predominantly localized to cluster 4; ARMC9-specific TCRs predominantly localized to cluster 4; TCR14 predominantly localized to cluster 6. Very few MYO5B-specific TCRs or ARMC9-specific TCRs were seen in other clusters.

Figure 6A:
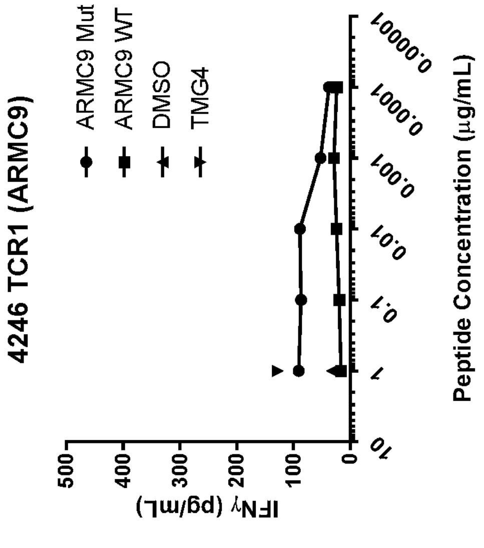
Figure 6B:
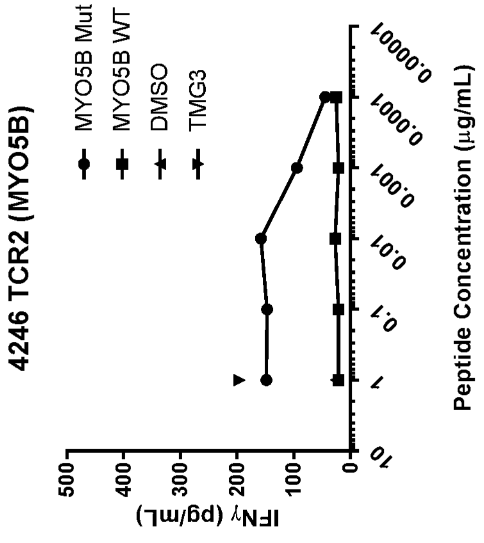
Figure 6C:
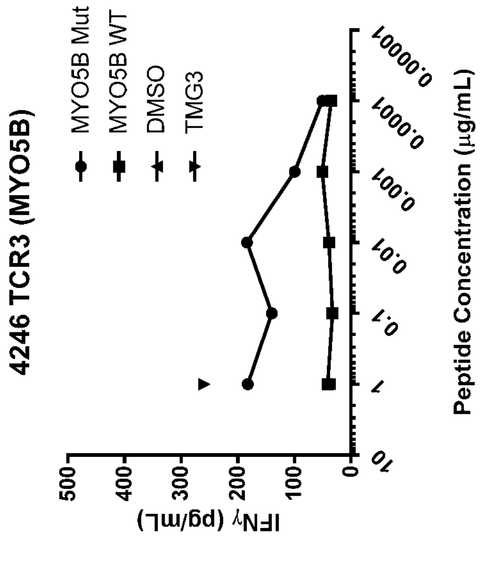
Figure 6D:
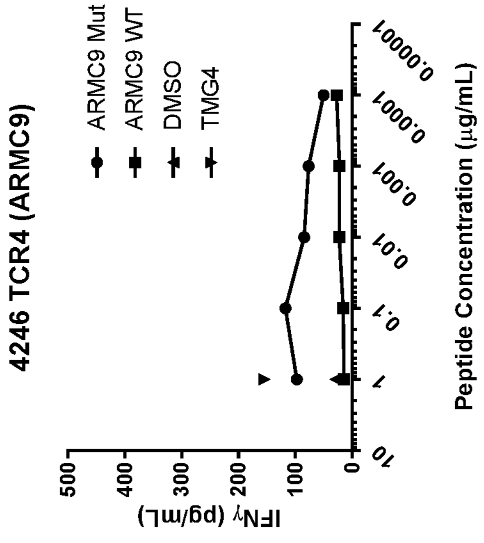
Figure 6E:
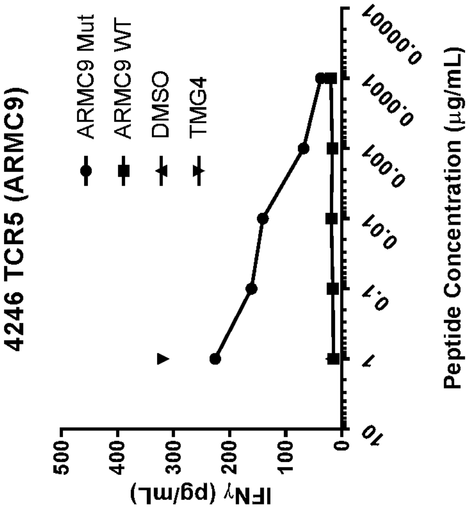
Figure 6F:
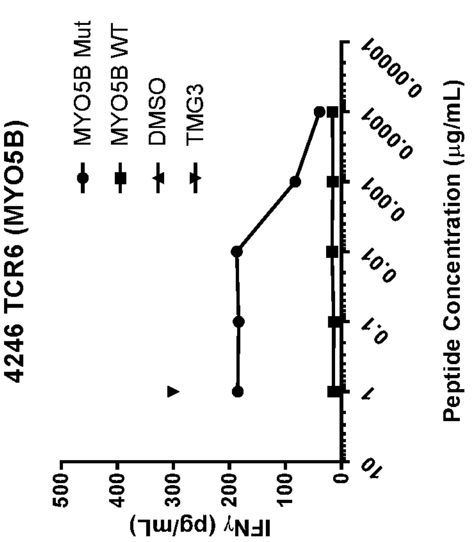
Figure 6G:
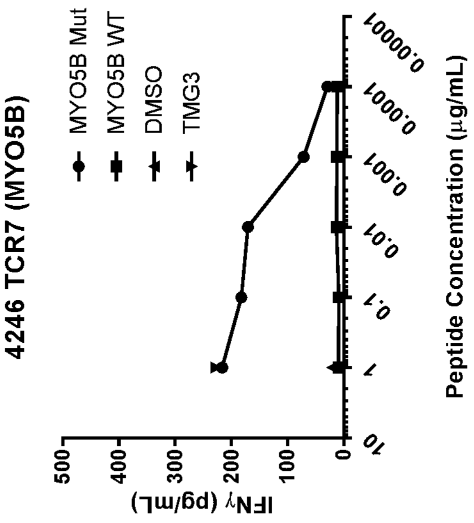
Figure 6H:
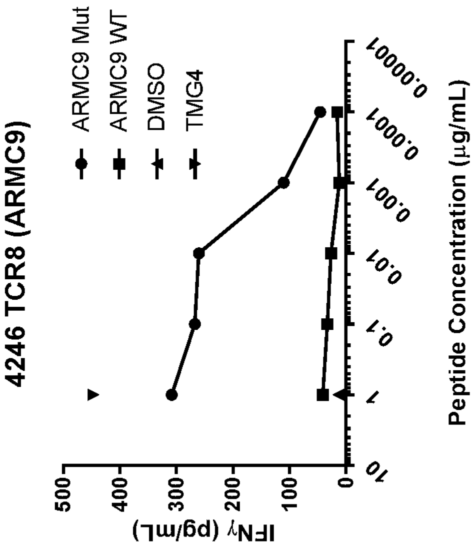
Figure 6I:
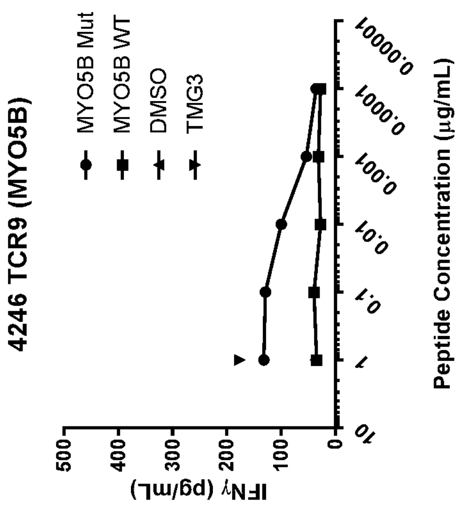
Figure 6J:
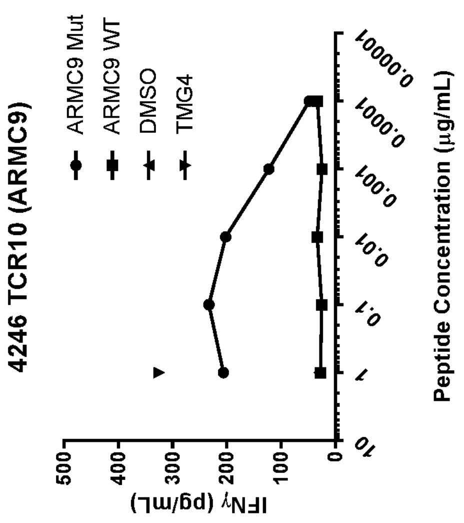
Figure 6K:
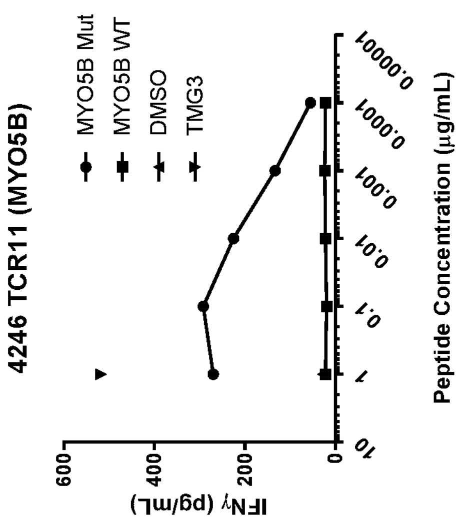
Figure 6N:
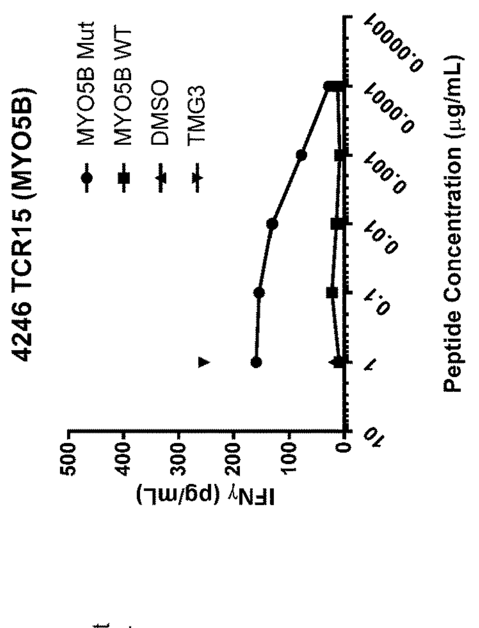
Figure 6M:
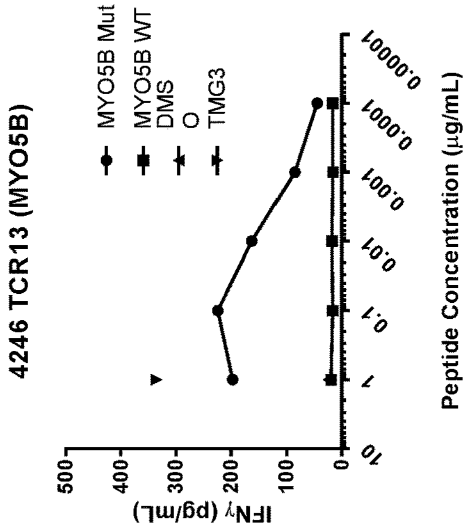
Figure 6L:
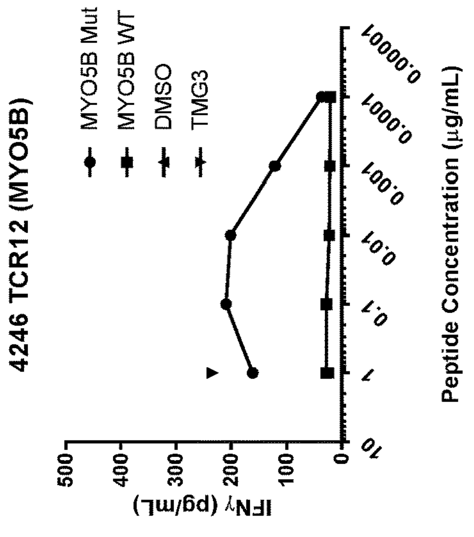

FIGS. 6A-6N are graphs showing the amount of interferon (IFN)-gamma (pg/mL) secreted by effector cells co-cultured with target Cos7 cells transfected with 100 ng HLA B40:01 and pulsed with the indicated concentration (μg/mL) of the indicated mutant (circles) or wild-type (squares) peptide. Effector cells were T cells allogeneic to Patient 4246 transduced with the indicated reconstructed TCR (TCR1 (6A), TCR2 (6B), TCR3 (6C), TCR4 (6D), TCR5 (6E), TCR6 (6F), TCR7 (6G), TCR8 (6H), TCR9 (6I), TCR10 (6J), TCR11 (6K), TCR12 (6L), TCR13 (6M), or TCR15 (6N)). Target cells treated with DMSO (▲) or transduced with tandem minigene (TMG) 3 (containing mutated MYO5B) or TMG 4 (containing mutated ARMC9) (▼) served as controls.

Figure 7A:
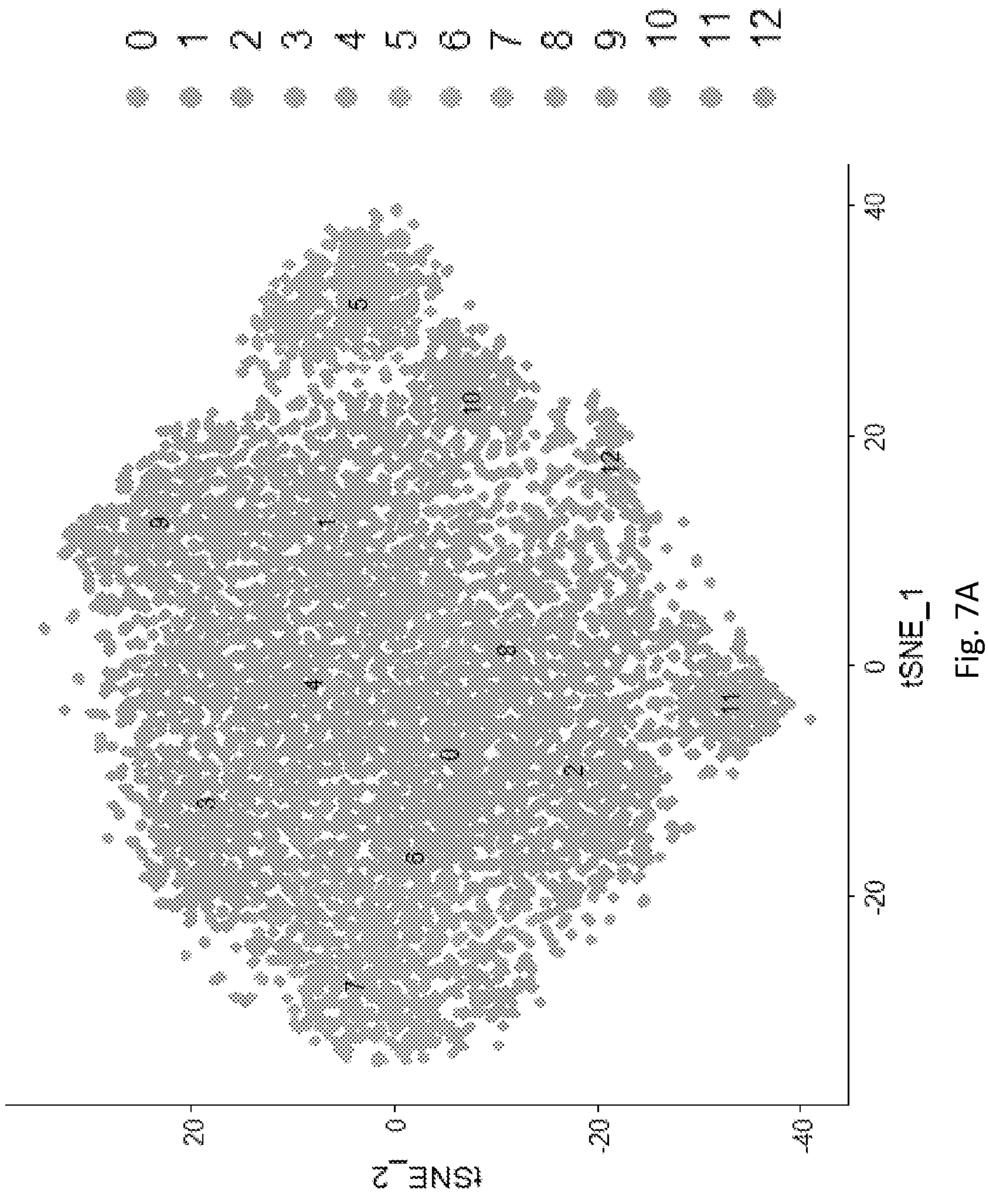

FIG. 7A shows the results of the t-SNE analysis of the single-cell transcriptome of tetramer-enriched samples from the peripheral blood of cancer Patients 4246, 4287, and 4317 (t-SNE map). The clusters are numbered 0-12.

Figure 7B:
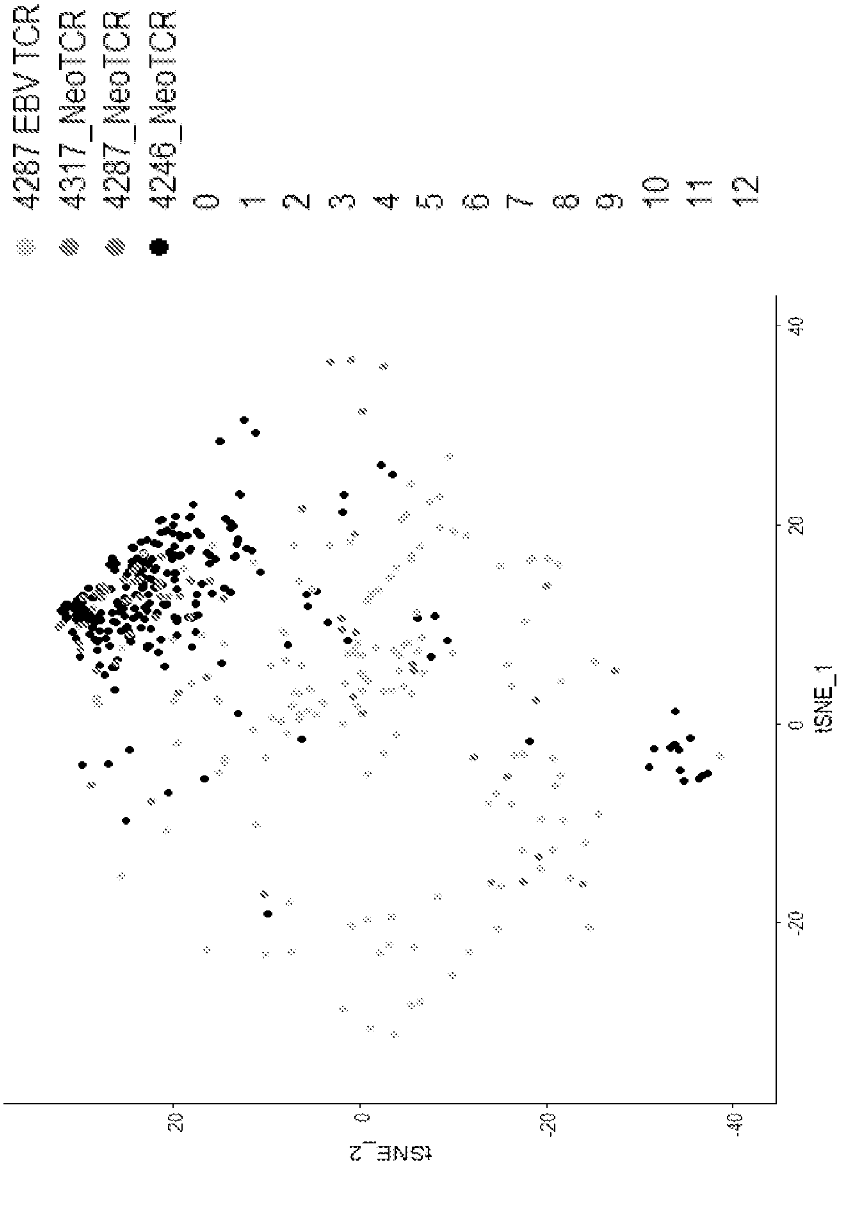

FIG. 7B shows the known neoantigen-reactive TCRs from Patients 4246, 4287, and 4317 and known EBV-reactive TCRs from Patient 4287 projected onto the t-SNE map of FIG. 7A. The known neoantigen-reactive TCRs localized to cluster 9.

Figure 8:
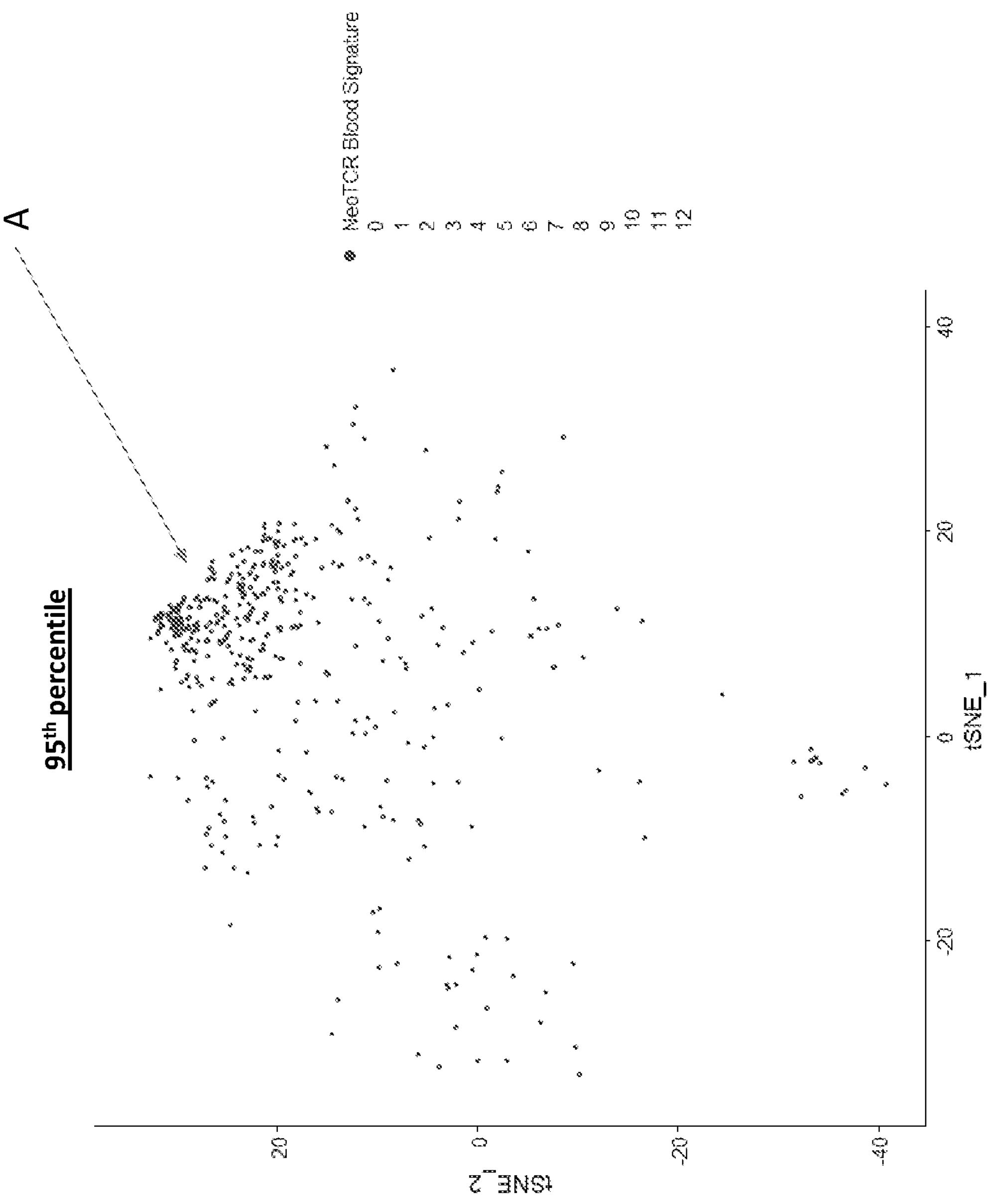

FIG. 8 shows the neoantigen-reactive peripheral blood $CD8^+$ T cells expressing the 95th percentile of the gene signature projected onto the t-SNE map of FIG. 7A. The cells in the region designated by "A" are also shown in FIG. 7B.

Figure 9A:
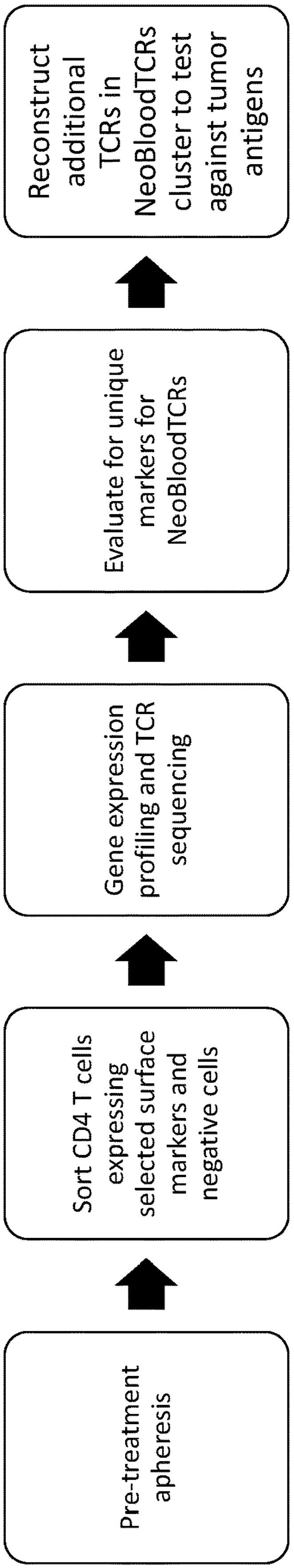

FIG. 9A is a schematic illustrating a strategy for identifying neoantigen-reactive T-cell gene signatures from pre-treatment patient peripheral blood samples by sorting for $CD4^+$ cells expressing selected surface markers followed by single-cell analysis according to an aspect of the invention.

Figure 9B:
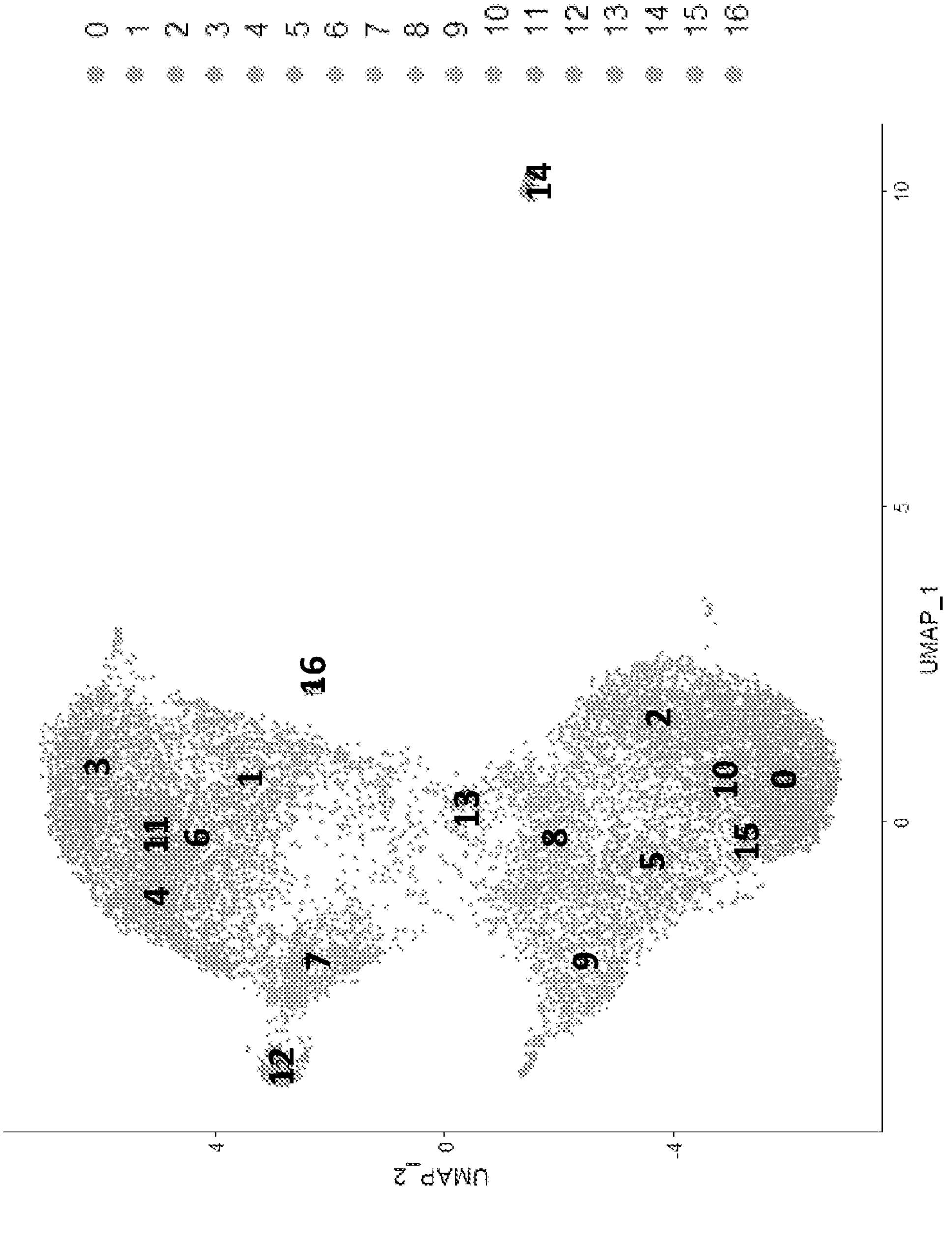

FIG. 9B shows the results of the UMAP analysis of the single-cell transcriptome of a cell surface marker-enriched sample from the peripheral blood of cancer Patient 4400 (UMAP space). The clusters are numbered 0-16.

Figure 9C:
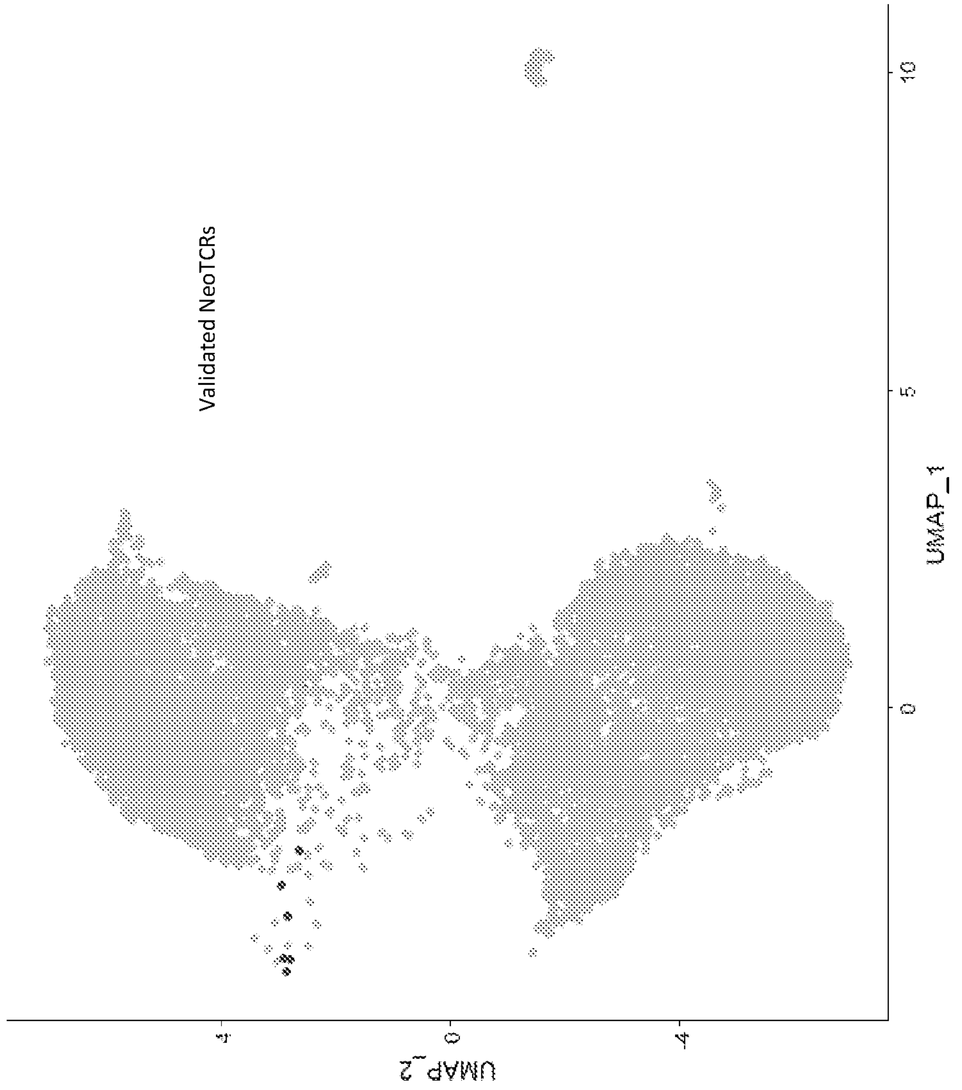

FIG. 9C shows the known neoantigen-reactive TCRs projected onto the UMAP space of FIG. 9B. The known neoantigen-reactive TCRs localized to clusters 7 and 12.

Figure 9D:
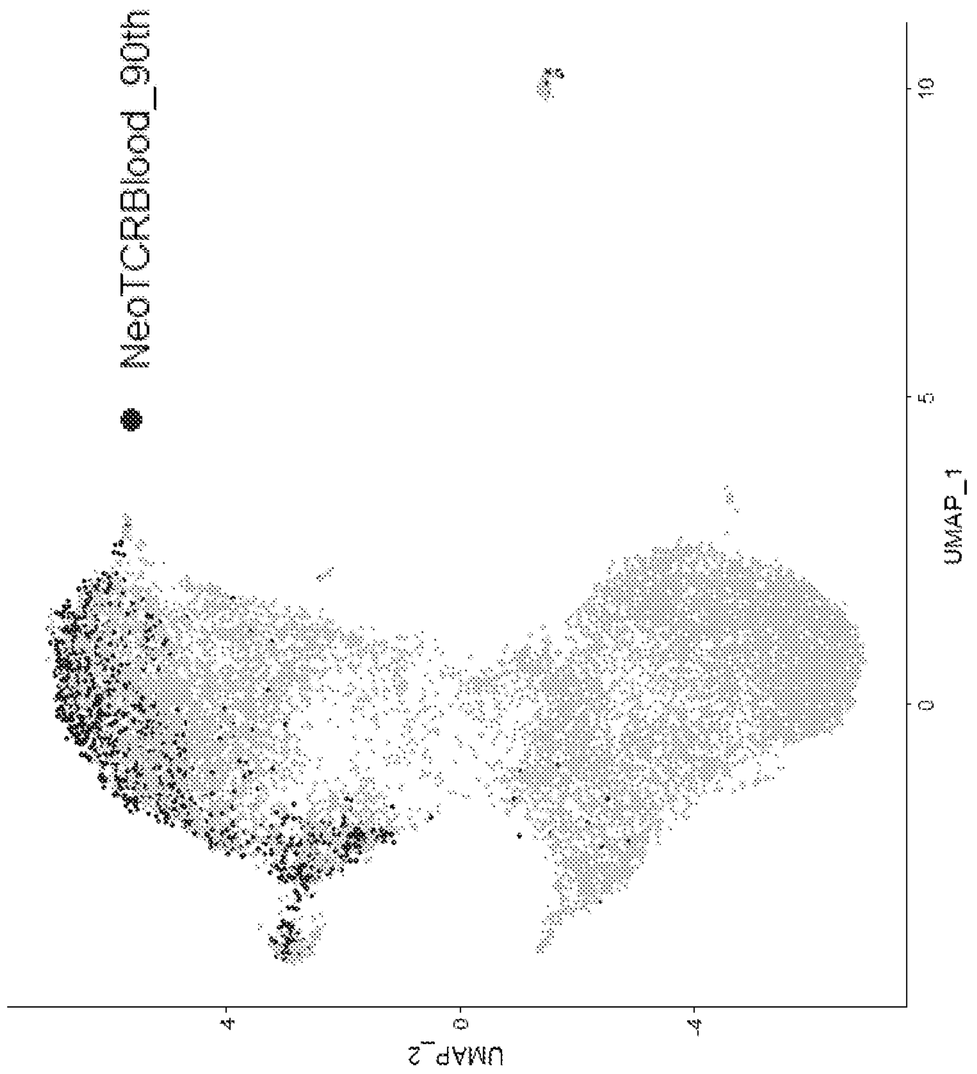

FIG. 9D shows the peripheral blood $CD4^+$ T cells expressing the 90th percentile of the gene signature projected onto the UMAP space of FIG. 9B.

Figure 9E:
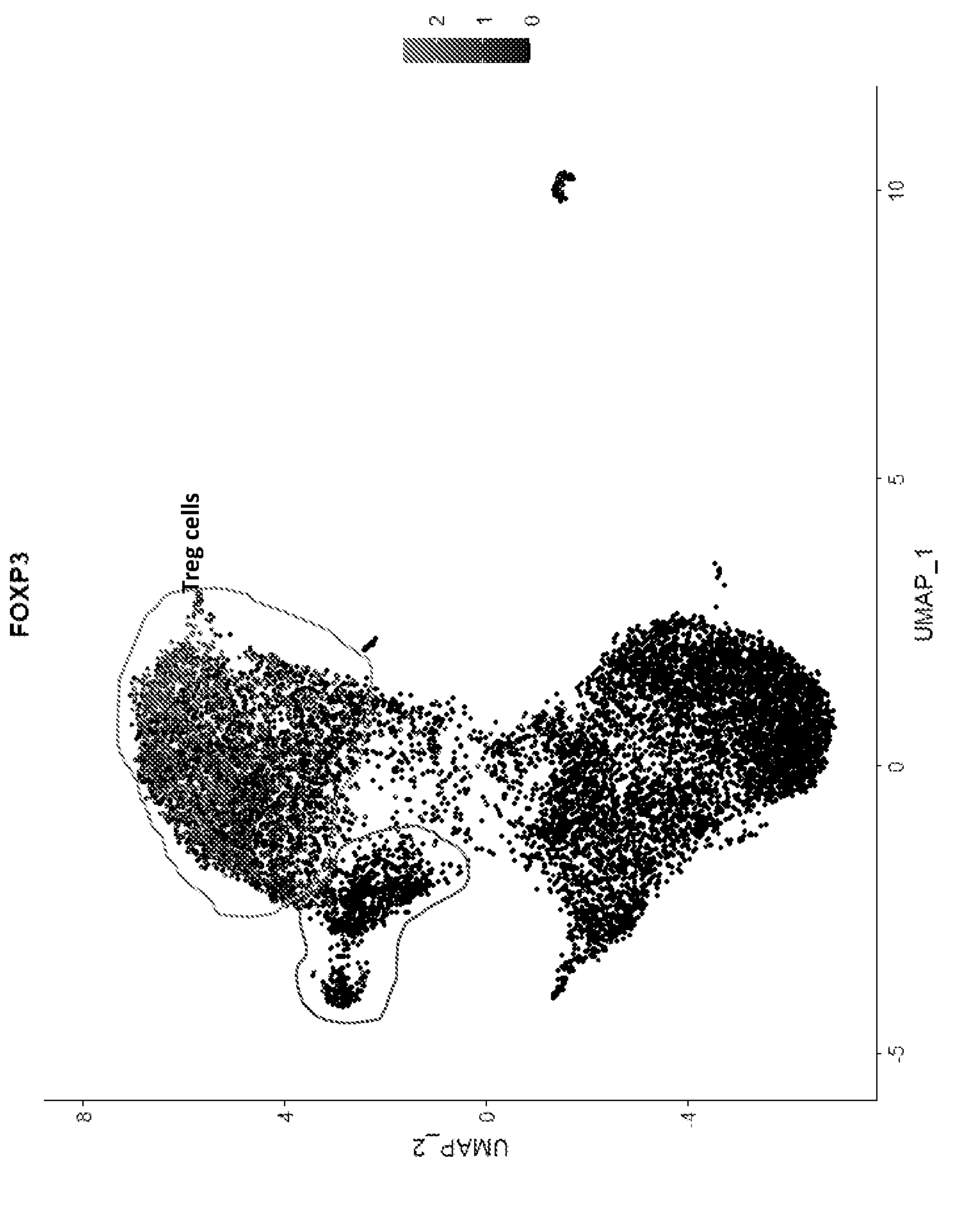

FIG. 9E shows the peripheral blood $CD4^+$ T cells expressing FoxP3 projected onto the UMAP space of FIG. 9B for the identification of Treg. The Treg cells are in the upper-most circled area.

Figure 9F:
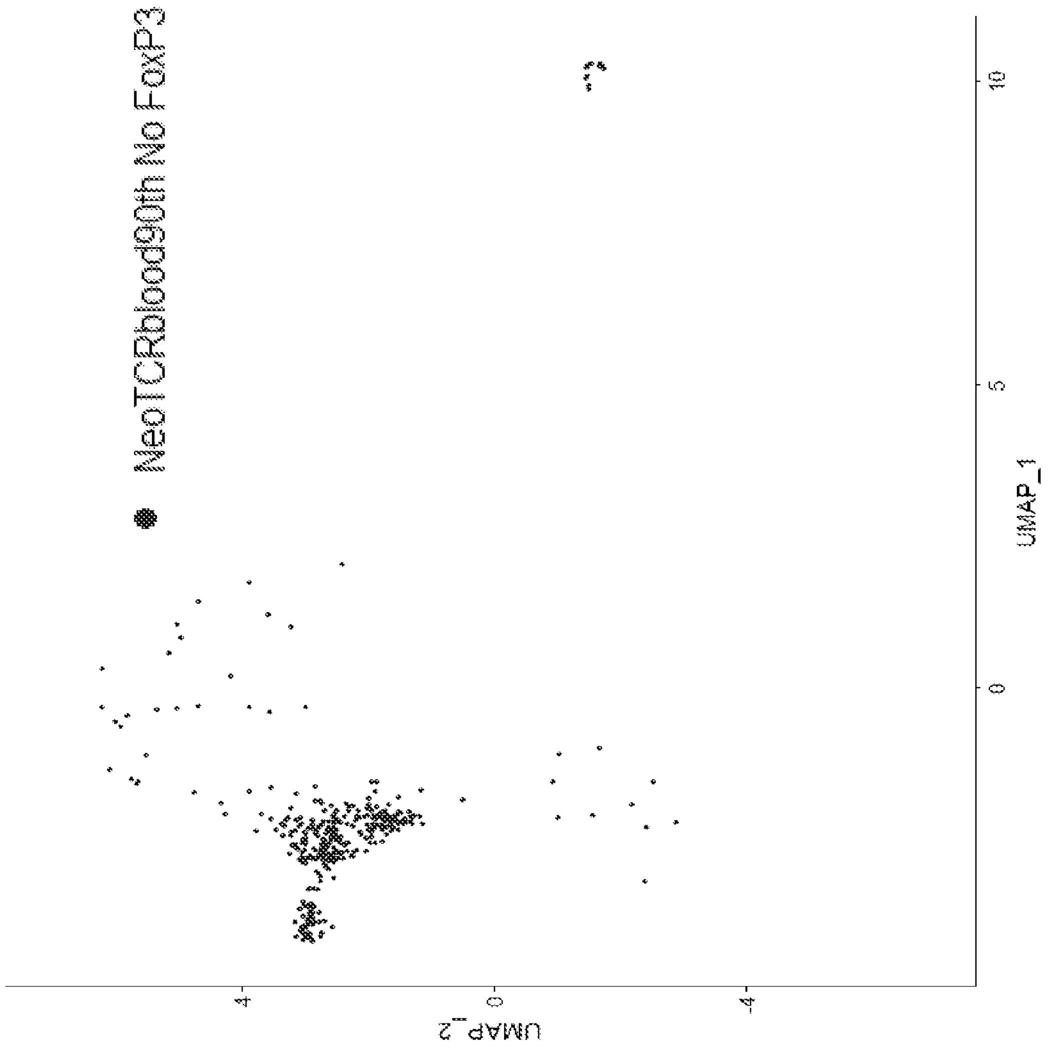

FIG. 9F shows the peripheral blood $Treg^{neg}$ $CD4^+$ expressing 90th percentile of gene signature onto the UMAP space of FIG. 9B.

Figure 10A:
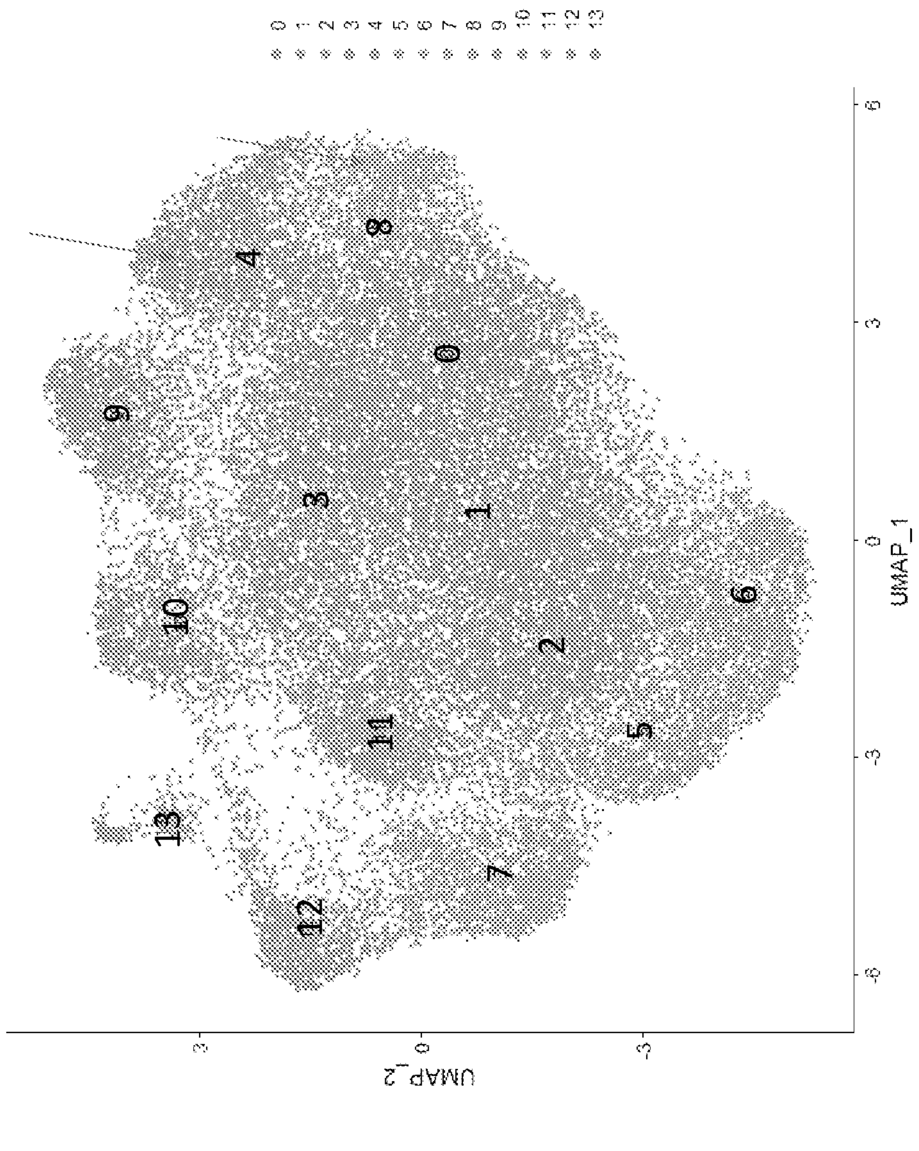

FIG. 10A shows the results of the UMAP analysis of the single-cell transcriptome of a cell surface marker-enriched sample from the peripheral blood of colorectal cancer Patients 4382, 4214, and 4422 (UMAP space). The clusters are numbered 0-13. Previously known neoantigen-reactive T cells clustered predominantly in clusters 4 and 8, indicated by arrows.

Figure 10B:
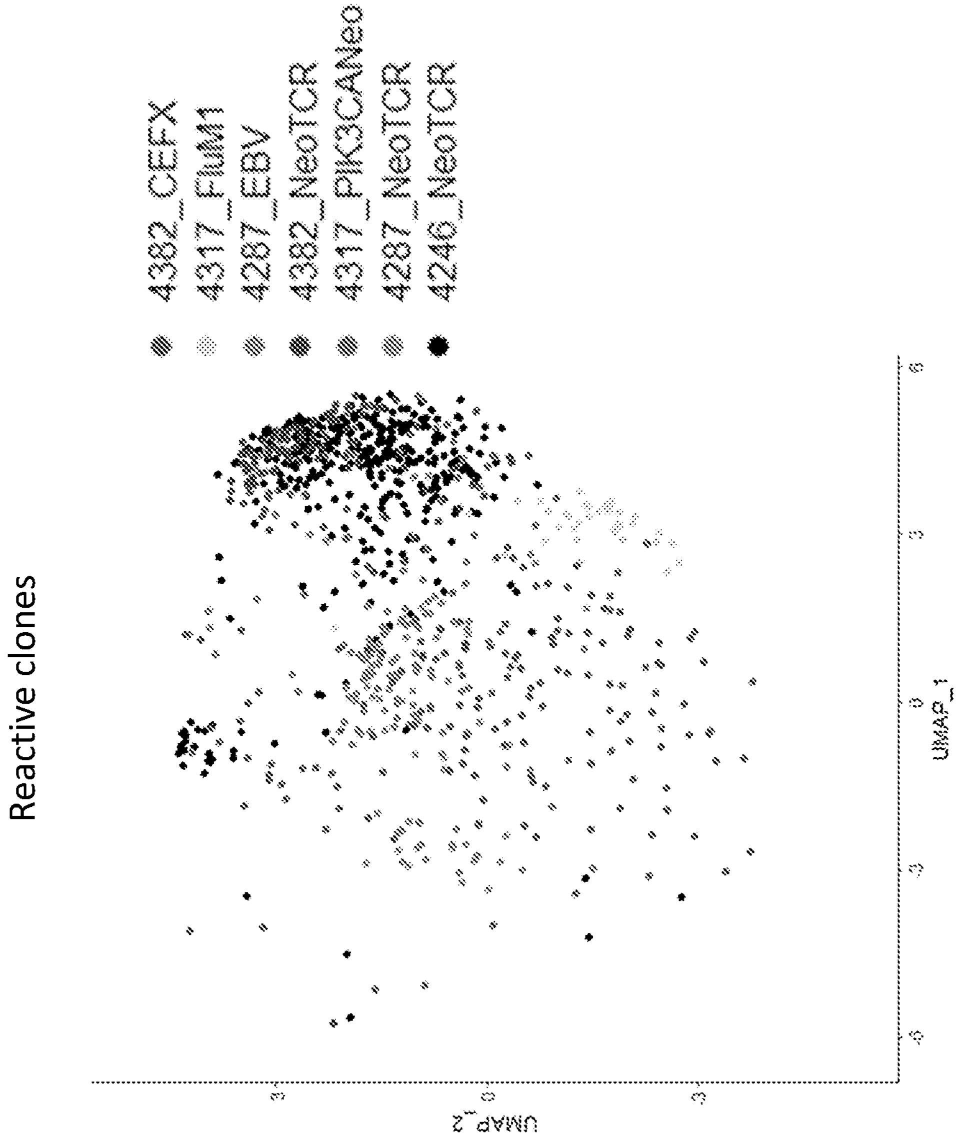

FIG. 10B shows the known neoantigen-reactive TCRs from Patients 4246, 4382, 4287 and known EBV-reactive TCRs from Patient 4287 were projected onto the UMAP space of FIG. 10A. Cells that showed reactivity against EBV, Flu, and a pool of peptides derived from CMV or EBV or Flu (CEFx) were projected on the UMAP space of FIG. 10A.

Figure 10C:
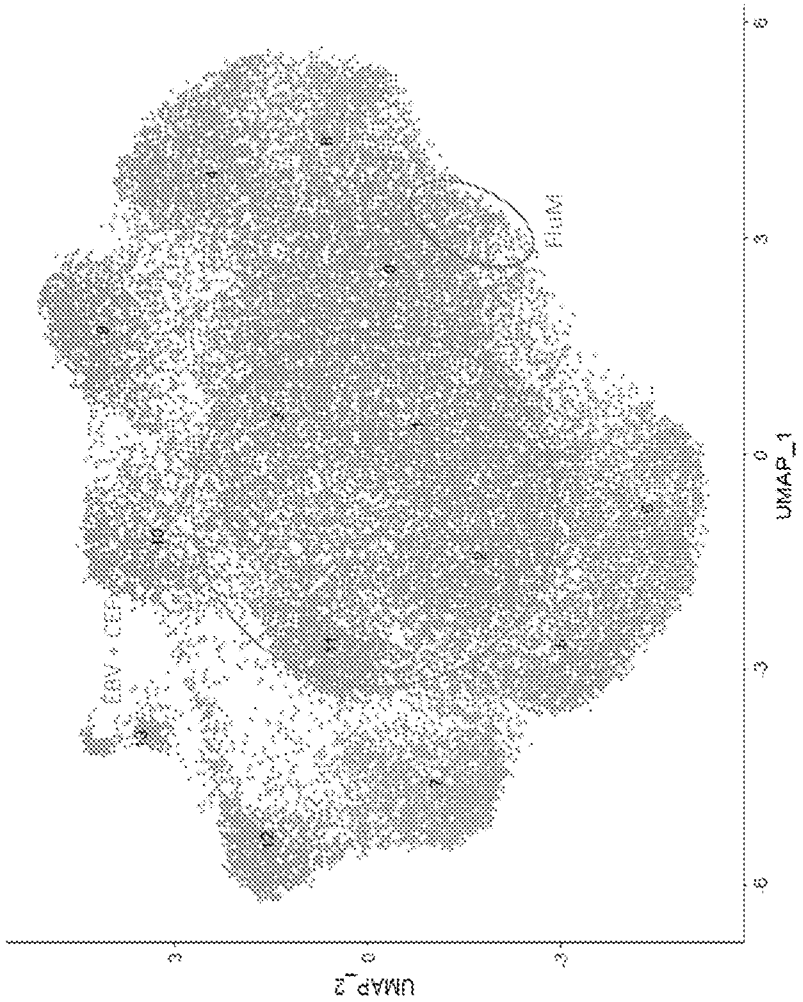

FIG. 10C shows the neoantigen-reactive peripheral blood $CD8^+$ T cells expressing the 90th percentile of the gene signature projected onto the UMAP space of FIG. 10A. The cells in the region encompassed by the large circle are reactive against EBV and CEFx. The cells in the region encompassed by the small circle are reactive against Flu.

DETAILED DESCRIPTION OF THE INVENTION

Treating advanced cancer patients with ACT involving tumor-infiltrating lymphocytes (TILs) can lead to tumor regression in solid tumors. However, TIL therapy requires tumor resection, in vitro growth of tumor fragments, functional assays to select fragments harboring tumor-reactive T cells, and finally, expansion of fragment cultures for cell transfer. TIL therapy may be invasive, laborious and/or time-consuming, which may be disadvantageous when treating advanced metastatic cancer patients. To bypass the need for surgery, several previous methods have been suggested to isolate tumor- and neoantigen-reactive T cells from the blood. However, these previous methods may have any one or more of a variety of disadvantages including, for example, requiring any one or more of: prior knowledge of patients' human leukocyte antigen (HLA) composition, prior knowledge of mutations expressed in the tumor, and prediction of the binding affinity of putative antigens to the HLA. These disadvantages may limit the methods to more commonly studied HLAs. An additional challenge to the success of these methods may be that the frequency of neoantigen-reactive cells in the blood is very low, possibly below the detection levels of these methods. Similar challenges exist with respect to the identification of T cells reactive to cancer-associated viral antigens.

The inventive methods may ameliorate these and other disadvantages by rapidly identifying T cells and TCR sequences of T-cells reactive against antigens, e.g., cancer-specific antigens and cancer-associated viral antigens, which could be used to engineer T-cells for therapy. The inventive methods may, advantageously, reduce or eliminate the need for invasive tumor resection that is commonly used to isolate tumor-reactive T cells and TCRs from tumor specimens.

It has been discovered that single-cell analysis of T cells isolated from peripheral blood has revealed a cell population that encompasses the majority of previously identified TCRs reactive against target antigens. This population may be defined by the gene expression profiles described herein. Using, for example, clonally defined T-cell receptors targeting unique somatic personalized mutations from a patient's blood, new unknown TCRs expressed by cells with the gene expression profiles described herein were reconstructed and were found to be reactive against target antigens. The inventive methods may dramatically increase the potential to rapidly isolate T cells and TCRs for cell-based immunotherapies of common cancers without the need for growing tumor infiltrating T-cells, expensive and time-consuming screening, and/or invasive tumor resection. The inventive methods may provide an unbiased approach for the isolation and construction of TCRs reactive against target antigens from blood samples of cancer patients based on a distinct T cell gene signature. The gene expression profiles described herein may also, advantageously, identify T cells and TCRs reactive to cancer-associated viral antigens.

An aspect of the invention provides a method of preparing an enriched population of T cells having antigenic specificity for a target antigen. The phrases "antigen-specific" and "antigenic specificity," as used herein, mean that the T cell can specifically bind to and immunologically recognize an antigen, or an epitope thereof, such that binding of the T cell to the antigen, or the epitope thereof, elicits an immune response. In this regard, the T cell populations obtained by the inventive methods may comprise a higher proportion of T cells having antigenic specificity for a target antigen as compared to cell populations that have not been obtained by the inventive methods.

In an aspect of the invention, the target antigen is a cancer antigen. The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host. Cancer antigens are known in the art and include, for instance, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc.

In an aspect of the invention, the target antigen is a neoantigen encoded by a cancer-specific mutation. Neoantigens are a class of cancer antigens which arise from cancer-specific mutations in expressed protein. The term "neoantigen" relates to a peptide or protein expressed by a cancer cell that includes one or more amino acid modifications compared to the corresponding wild-type (non-mutated) peptide or protein that is expressed by a normal (non-cancerous) cell. A neoantigen may be patient-specific. A "cancer-specific mutation" is a somatic mutation that is present in the nucleic acid of a tumor or cancer cell but absent in the nucleic acid of a corresponding normal, i.e. non-tumorous or non-cancerous, cell.

In an aspect of the invention, the target antigen is a viral-specific antigen. Viral-specific antigens are known in the art and include, for example, any viral protein or peptide expressed or presented by virally-infected cells (APCs) which are not expressed or presented by cells which are not infected by a virus, e.g., env, gag, pol, gp120, thymidine kinase, and the like. In an aspect of the invention, the viral-specific antigen is a cancer-associated viral antigen, for example, human papillomavirus (HPV) 16 E4, HPV 16 E6, HPV 16 E7, HPV 18 E6, HPV 18 E7, and the like. The viral-specific antigen may be, for example, a herpes virus antigen, pox virus antigen, hepadnavirus antigen, papilloma virus antigen, adenovirus antigen, coronavirus antigen, orthomyxovirus antigen, paramyxovirus antigen, flavivirus antigen, and calicivirus antigen. For example, the viral-specific antigen may be selected from the group consisting of respiratory syncytial virus (RSV) antigen, influenza virus antigen, herpes simplex virus antigen, Epstein-Barr (EBV) virus antigen, HPV antigen, varicella virus antigen, cytomegalovirus antigen, hepatitis A virus antigen, hepatitis B virus antigen, hepatitis C virus antigen, human immunodeficiency virus (HIV) antigen, human T-lymphotropic virus antigen, calicivirus antigen, adenovirus antigen, and Arena virus antigen. In an aspect of the invention, the cancer-associated viral antigen is a HPV antigen or an EBV antigen.

The method may comprise isolating T cells from a blood sample of a patient. The blood sample may be a peripheral blood sample. As such, the blood sample may be obtained by any suitable means, including, without limitation, venous puncture and arterial puncture. Although HLA molecules expressed by the patient may be identified, in an aspect of the invention, the method does not require identifying any HLA molecules expressed by the patient. Similarly, although one or more of the target antigens expressed by the patient may be identified, in an aspect of the invention, the method does not require identifying any target antigens expressed by the patient. In an aspect of the invention, the patient is a cancer patient. In another aspect of the invention, the patient is a patient suffering from a viral condition.

Although the blood sample may be from a patient who has been treated with T cell therapy, in a preferred aspect, the blood sample is from a patient who has not been treated with T cell therapy. The T cell therapy may comprise any therapy comprising the administration of one or both of (i) one or more T cells and (ii) one or more cells which have been modified to express a T cell receptor. The blood sample may be from a patient who has been treated with forms of immunotherapy other than T cell therapy. Cancer immunotherapy is a form of cancer treatment that uses the immune system to attack cancer cells. Anti-viral immunotherapy is a form of treatment that uses the immune system to attack viruses or cells infected with a virus. Immunotherapies other than T cell therapy may include, but are not limited to, administration of any one or more of checkpoint inhibitors, vaccines, cytokines, antibodies, and chimeric antigen receptors (CARs).

In an aspect of the invention, isolating T cells from the blood sample of the patient comprises isolating $CD8^+$ T cells from the blood sample. In another aspect of the invention, isolating T cells from the blood sample of the patient comprises isolating $CD4^+$ T cells from the blood sample.

The method may further comprise selecting the isolated T cells which have a gene expression profile. Selecting the isolated T cells which have the gene expression profile may comprise sorting the T cells into separate single T cell samples and separately detecting the expression and/or non-expression of one or more genes by one or more single T cells. In an aspect of the invention, selecting the isolated T cells which have the gene expression profile comprises carrying out single cell transcriptome analysis.

Detecting the expression and/or non-expression of one or more genes by the one or more single T cells may be carried out using, for example, the CHROMIUM Single Cell Gene Expression Solution system (10× Genomics, Pleasanton, CA) ("CHROMIUM system"). The CHROMIUM system performs deep profiling of complex cell populations with high-throughput digital gene expression on a cell-by-cell basis. The CHROMIUM system barcodes the cDNA of individual cells for 5' transcriptional or TCR analysis. For example, samples may start with an input of 10,000 cells and yield data for about 3000 cells/sample, with an average of about 500 genes/cell.

In an aspect of the invention, selecting the isolated T cells which have the gene expression profile comprises carrying out one or more of cellular indexing of transcriptomes analysis, epitopes by sequencing analysis, and Cellular Indexing of Transcriptomes and Epitopes by Sequencing (CITE-Seq) analysis. CITE-Seq is described at, for example, Stoeckius et al., *Nat. Methods,* 14(9): 865-868 (2017). Briefly, CITE-seq combines antibody-based detection of protein markers together with transcriptome profiling for many single cells in parallel. Oligonucleotide-labeled antibodies are used to integrate cellular protein and transcriptome measurements into an efficient, single-cell readout.

Because of the high dimensionality of the data yielded by the single cell transcriptome analysis (e.g., about 3000 cells/sample and about 500 genes/cell), dimensionality reduction may be carried out for analysis of the gene expression data. Accordingly, in an aspect of the invention, selecting the isolated T cells which have the gene expression profile comprises carrying out one or more single cell dimensional reduction methods. An example of a single cell dimensional reduction method is t-Distributed Stochastic Neighbor Embedding (t-SNE) analysis. t-SNE visualizes high-dimensional data by giving each data point a location in a two or three-dimensional map. t-SNE is described at, for example, Van der Maaten and Hinton, J. *Machine Learning Res.,* 9: 2579-2605 (2008). Briefly, t-SNE is carried out in two steps. In step 1, a probability distribution is created in the high-dimensional space that dictates the relationships between various neighboring points. In step 2, a low dimensional space is recreated that follows that probability distribution as best as possible. The "t" in t-SNE comes from the t-distribution, which is the distribution used in Step 2. The "S" and "N" ("stochastic" and "neighbor") come from the use of a probability distribution across neighboring points. Another example of a single cell dimensional reduction method is Uniform Manifold Approximation and Projection (UMAP).

The gene expression profile may include (i) positive expression of one or more genes, (ii) negative expression of one or more genes, or (iii) positive expression of one or more genes in combination with negative expression of one or more genes. As used herein, the term "positive" (which may be abbreviated as "f"), with reference to expression of the indicated gene, means that the T cell upregulates expression of the indicated gene as compared to other T cells in the blood sample of the patient. Upregulated expression may encompass, for example, a quantitative increase in expression of the indicated gene by an average logarithmic fold change (to the base 2) of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or a range of any two of the foregoing values, or more. The term "negative" (which may be abbreviated as "–"), as used herein with reference to expression of the indicated gene, means that the T cell downregulates expression of the indicated gene as compared to other T cells in the blood sample of the patient. Downregulated expression may encompass, for example, a quantitative decrease in expression of the indicated gene by an average logarithmic fold change (to the base 2) of about −1, about −2, about −3, about −4, about −5, about −6, about −7, about −8, about −9, about −10, about −20, about −30, about −40, about −50, about −60, about −70, about −80, about −90, about −100, about −110, about −120, about −130, about −140, about −150, about −160, about −170, about −180, about −190, about −200, about −210, about −220, about −230, about −240, about −250, about −260, about −270, about −280, about −290, about −300, about −310, about −320, about −330, about −340, about −350, about −360, about −370, about −380, about −390, about −400, about −410, about −420, about −430, about −440, about −450, about −460, about −470, about −480, about −490, about −500, about −510, about −520, about −530, about −540, about −550, about −560, about −570, about −580, about −590, about −600, or a range of any two of the foregoing values, or more.

In an aspect of the invention, the gene expression profile comprises one or more of ACTG1$^+$, AES$^+$, ANXA2$^+$, ANXA5$^+$, ARPC2$^+$, ARPC3$^+$, CD3D$^+$, CD52$^+$, CD7$^+$, CD62L$^+$, CD99$^+$, CORO1A$^+$, COTL1$^+$, CRIP1$^+$, CXCL13$^+$, EMP3$^+$, FLNA$^+$, FTL$^+$, FYB1$^+$, GAPDH$^+$, H2AFV$^+$, HMGB2$^+$, IL32$^+$, ITGB1$^+$, LSP1$^+$, LTB$^+$, PPIA$^+$, S100A10$^+$, S100A4$^+$, S100A6$^+$, SLC25A5$^+$, SUB1$^+$, TIGIT$^+$, TMSB10$^+$, VIM$^+$, ACTB$^-$, B2M$^-$, BTG1$^-$, CCL4$^-$, CCL4L2$^-$, CCL5$^-$, CD74$^-$, EEF1A1$^-$, FTH1$^-$, GZMK$^-$, HLA-DRA$^-$, MTRNR2L12$^-$, PNRC1$^-$, RPL10$^-$, RPL13$^-$, RPL3$^-$, RPL30$^-$, RPL32$^-$, RPL34$^-$, RPLP1$^-$, RPL39$^-$, RPL5$^-$, RPLP0$^-$, RPS12$^-$, RPS14$^-$, RPS18$^-$, RPS19$^-$, RPS21$^-$, RPS23$^-$, RPS24$^-$, RPS3$^-$, RPS3A$^-$, RPS4X$^-$, RPS6$^-$, and ZC3HAV1$^-$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or more (or a range of any two of the foregoing values) of ACTG1$^+$, AES$^+$, ANXA2$^+$, ANXA5$^+$, ARPC2$^+$, ARPC3$^+$, CD3D$^+$, CD52$^+$, CD7$^+$, CD62L$^+$, CD99$^+$, CORO1A$^+$, COTL1$^+$, CRIP1$^+$, CXCL13$^+$, EMP3$^+$, FLNA$^+$, FTL$^+$, FYB1$^+$, GAPDH$^+$, H2AFV$^+$, HMGB2$^+$, IL32$^+$, ITGB1$^+$, LSP1$^+$, LTB$^+$, PPIA$^+$, S100A10$^+$, S100A4$^+$, S100A6$^+$, SLC25A5$^+$, TMSB10$^+$, VIM$^+$, ACTB$^-$, B2M$^-$, BTG1$^-$, CCL4$^-$, CCL4L2$^-$, CCL5$^-$, CD74$^-$, EEF1A1$^-$, FTH1$^-$, GZMK$^-$, HLA-DRA$^-$, MTRNR2L12$^-$, PNRC1$^-$, RPL10$^-$, RPL13$^-$, RPL3$^-$, RPL30$^-$, RPL32$^-$, RPL34$^-$, RPLP1$^-$, RPL39$^-$, RPL5$^-$, RPLP0$^-$, RPS12$^-$, RPS14$^-$, RPS18$^-$, RPS19$^-$, RPS21$^-$, RPS23$^-$, RPS24$^-$, RPS3$^-$, RPS3A$^-$, RPS4X$^-$, RPS6$^-$, and ZC3HAV1$^-$.

In another aspect of the invention, the gene expression profile comprises all of ACTG1$^+$, AES$^+$, ANXA2$^+$, ANXA5$^+$, ARPC2$^+$, ARPC3$^+$, CD3D$^+$, CD52$^+$, CD7$^+$, CD62L$^+$, CD99$^+$, CORO1A$^+$, COTL1$^+$, CRIP1$^+$, CXCL13$^+$, EMP3$^+$, FLNA$^+$, FTL$^+$, FYB1$^+$, GAPDH$^+$, H2AFV$^+$, HMGB2$^+$, IL32$^+$, ITGB1$^+$, LSP1$^+$, LTB$^+$, PPIA$^+$, S100A10$^+$, S100A4$^+$, S100A6$^+$, SLC25A5$^+$, TMSB10$^+$, VIM$^+$, ACTB$^-$, B2M$^-$, BTG1$^-$, CCL4$^-$, CCL4L2$^-$, CCL5$^-$, CD74$^-$, EEF1A1$^-$, FTH1$^-$, GZMK$^-$, HLA-DRA$^-$, MTRNR2L12$^-$, PNRC1$^-$, RPL10$^-$, RPL13$^-$, RPL3$^-$, RPL30$^-$, RPL32$^-$, RPL34$^-$, RPLP1$^-$, RPL39$^-$, RPL5$^-$, RPLP0$^-$, RPS12$^-$, RPS14$^-$, RPS18$^-$, RPS19$^-$, RPS21$^-$, RPS23$^-$, RPS24$^-$, RPS3$^-$, RPS3A$^-$, RPS4X$^-$, RPS6$^-$, and ZC3HAV1$^-$.

In an aspect of the invention, the gene expression profile comprises one or more of CARS$^+$, CD39$^+$, CD62L$^+$, CD70$^+$, CD82$^+$, CTLA4$^+$, CXCL13$^+$, HLA-DRA$^+$, HLA-DRB1$^+$, ITAGE$^+$, LAG3$^+$, LGALS3$^+$, PDCD1$^+$, SA100A4$^+$, TIGIT$^+$, and TOX+. For example, the gene expression profile may comprise any 1, 2, 3, 4, 5, 6, 7, 8, 9, 10, 11, 12, 13, 14, 15, or more (or a range of any two of the foregoing values) of CARS⁺, CD39⁺, CD62L⁺, CD70⁺, CD82⁺, CTLA4⁺, CXCL13⁺, HLA-DRA⁺, HLA-DRB1⁺, ITAGE⁺, LAG3⁺, LGALS3⁺, PDCD1⁺, SA100A4⁺, TIGIT⁺, and TOX⁺. In an aspect of the invention, the gene expression profile comprises all of CARS⁺, CD39⁺, CD62L⁺, CD70⁺, CD82⁺, CTLA4⁺, CXCL13⁺, HLA-DRA⁺, HLA-DRB1⁺, ITAGE⁺, LAG3⁺, LGALS3⁺, PDCD1⁺, SA100A4⁺, TIGIT⁺, and TOX⁺.

In an aspect of the invention, the gene expression profile comprises CD8⁺ and one or more of ALOX5AP⁺, ANXA2⁺, ANXA5⁺, CARS⁺, CD82⁺, CDC25B⁺, CHN1⁺, CLECL1⁺, COTL1⁺, CYTOR⁺, FLNA⁺, GATA3⁺, HLA-DPA1⁺, HLA-DQA2⁺, HLA-DQB1⁺, HLA-DRA⁺, HLA-DRB1⁺, HLA-DRB5⁺, ITGB1⁺, ITM2A⁺, LGALS3⁺, MYO1G⁺, P2RY8⁺, PASK⁺, RBPJ⁺, S100A11⁺, TPM4⁺, TRADD⁺, UBXN11⁺, CCL4⁻, CCL5⁻, CCR7⁻, CYTIP⁻, EEF1G⁻, GZMH⁻, IMPDH2⁻, LINC02446⁻, LYAR⁻, MYC⁻, NKG7⁻, NUCB2⁻, PITPNC1⁻, PLAC8⁻, and TCF7⁻. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more (or a range of any two of the foregoing values) of ALOX5AP⁺, ANXA2⁺, ANXA5⁺, CARS⁺, CD82⁺, CDC25B⁺, CHN1⁺, CLECL1⁺, COTL1⁺, CYTOR⁺, FLNA⁺, GATA3⁺, HLA-DPA1⁺, HLA-DQA2⁺, HLA-DQB1⁺, HLA-DRA⁺, HLA-DRB1⁺, HLA-DRB5⁺, ITGB1⁺, ITM2A⁺, LGALS3⁺, MYO1G⁺, P2RY8⁺, PASK⁺, RBPJ⁺, S100A11⁺, TPM4⁺, TRADD⁺, UBXN11⁺, CCL4⁻, CCL5⁻, CCR7⁻, CYTIP⁻, EEF1G⁻, GZMH⁻, IMPDH2⁻, LINC02446⁻, LYAR⁻, MYC⁻, NKG7⁻, NUCB2⁻, PITPNC1⁻, PLAC8⁻, and TCF7⁻. In an aspect of the invention, the gene expression profile comprises CD8⁺ and all of ALOX5AP⁺, ANXA2⁺, ANXA5⁺, CARS⁺, CD82⁺, CDC25B⁺, CHN1⁺, CLECL1⁺, COTL1⁺, CYTOR⁺, FLNA⁺, GATA3⁺, HLA-DPA1⁺, HLA-DQA2⁺, HLA-DQB1⁺, HLA-DRA⁺, HLA-DRB1⁺, HLA-DRB5⁺, ITGB1⁺, ITM2A⁺, LGALS3⁺, LIME1⁺, MYO1G⁺, P2RY8⁺, PASK⁺, RBPJ⁺, S100A11⁺, TPM4⁺, TRADD⁺, UBXN11⁺, CCL4⁻, CCL5⁻, CCR7⁻, CYTIP⁻, EEF1G⁻, GZMH⁻, IMPDH2⁻, LINC02446⁻, LYAR⁻, MYC⁻, NKG7⁻, NUCB2⁻, PITPNC1⁻, PLAC8⁻, and TCF7⁻.

In an aspect of the invention, the gene expression profile comprises CD8⁺ and one or more of ALOX5AP⁺, ANXA2⁺, ANXA5⁺, CARS⁺, CD82⁺, CDC25B⁺, CHN1⁺, CLECL1⁺, COTL1⁺, FLNA⁺, HLA-DPA1⁺, HLA-DQA2⁺, HLA-DQB1⁺, HLA-DRA⁺, HLA-DRB1⁺, HLA-DRB5⁺, ITGB1⁺, ITM2A⁺, LGALS3⁺, MYO1G⁺, PASK⁺, S100A11⁺, TIGIT⁺, and UBXN11⁺. For example, the gene expression profile may comprise CD8⁺ and any 1, 2, 3, 4, 5, 6, 7, 8, 9, 10, 11, 12, 13, 14, 15, 16, 17, 18, 19, 20, 21, 22, 23, or 24 or more (or a range of any two of the foregoing values) of ALOX5AP⁺, ANXA2⁺, ANXA5⁺, CARS⁺, CD82⁺, CDC25B⁺, CHN1⁺, CLECL1⁺, COTL1⁺, FLNA⁺, HLA-DPA1⁺, HLA-DQA2⁺, HLA-HLA-DRA⁺, HLA-DRB1⁺, HLA-DRB5⁺, ITGB1⁺, ITM2A⁺, LGALS3⁺, MYO1G⁺, PASK⁺, S100A11⁺, TIGIT⁺, and UBXN11⁺. In an aspect of the invention, the gene expression profile comprises CD8⁺ and all of ALOX5AP⁺, ANXA2⁺, ANXA5⁺, CARS⁺, CD82⁺, CDC25B⁺, CHN1⁺, CLECL1⁺, COTL1⁺, FLNA⁺, HLA-DPA1⁺, HLA-DQA2⁺, HLA-DQB1⁺, HLA-DRA⁺, HLA-DRB1⁺, HLA-DRB5⁺, ITGB1⁺, ITM2A⁺, LGALS3⁺, MYO1G⁺, PASK⁺, S100A11⁺, TIGIT⁺, and UBXN11⁺.

In an aspect of the invention, the gene expression profile comprises CD8⁺ and one or more of CD45RO⁺, CD45RA⁻, HLA-DR⁺, CD39⁺, and CD103⁺. For example, the gene expression profile may comprise CD8⁺ and any 1, 2, 3, 4, or more (or a range of any two of the foregoing values) of CD45RO⁺, CD45RA⁻, HLA-DR⁺, CD39⁺, and CD103⁺. In an aspect of the invention, the gene expression profile comprises CD8⁺ and all of CD45R0⁺, CD45RA⁻, HLA-DR⁺, CD39⁺, and CD103⁺.

In an aspect of the invention, the gene expression profile comprises CD8⁺ and one or more of CD45RO⁺, CD45RA⁻, HLA-DR⁺, CD39⁺, and TIGIT⁺. In an aspect of the invention, the gene expression profile comprises CD8⁺ and any 1, 2, 3, 4, or more (or a range of any two of the foregoing values) of CD45RO⁺, CD45RA⁻, HLA-DR⁺, CD39⁺, and TIGIT⁺. In an aspect of the invention, the gene expression profile comprises CD8⁺ and all of CD45RO⁺, CD45RA⁻, HLA-DR⁺, CD39⁺, and TIGIT⁺.

In an aspect of the invention, the gene expression profile comprises CD8⁺ and one or more of CD45RO⁺, CD45RA⁻, HLA-DR⁺, CD39⁺, and PD-1⁺. In an aspect of the invention, the gene expression profile comprises CD8⁺ and any 1, 2, 3, 4, or more (or a range of any two of the foregoing values) of CD45RO⁺, CD45RA⁻, HLA-DR⁺, CD39⁺, and PD-1⁺. In an aspect of the invention, the gene expression profile comprises CD8⁺ and all of CD45RO⁺, CD45RA⁻, HLA-DR⁺, CD39⁺, and PD-1⁺.

In an aspect of the invention, the gene expression profile comprises CD4⁺ and one or more of CD45RO⁺, CD45RA⁻, HLA-DR⁺, and CD39⁺. In an aspect of the invention, the gene expression profile comprises CD4⁺ and any 1, 2, 3, or more (or a range of any two of the foregoing values) of CD45R0⁺, CD45RA⁻, HLA-DR⁺, and CD39⁺. In an aspect of the invention, the gene expression profile comprises CD4⁺ and all of CD45RO⁺, CD45RA⁻, HLA-DR⁺, and CD39⁺.

In an aspect of the invention, the gene expression profile comprises CD4⁺ and one or more of AK4⁺, APOBEC3G⁺, C12orf75⁺, CCL5⁺, CD74⁺, COTL1⁺, CST7⁺, CXCL13⁺, CXCR3⁺, DUSP2⁺, EEF1A1⁺, F2R⁺, GAPDH⁺, GNLY⁺, GZMA⁺, GZMK⁺, HCST⁺, HLA-DPA1⁺, LYAR⁺, LYST⁺, MRPL10⁺, MYO1G⁺, NKG7⁺, PABPC1⁺, PDCD1⁺, PFN1⁺, PRF1⁺, RAB27A⁺, RPL10⁺, RPL11⁺, RPL13⁺, RPL18A⁺, RPL19⁺, RPL30⁺, RPL32⁺, RPL34⁺, RPL8⁺, RPL9⁺, RPLP1⁺, RPS12⁺, RPS13⁺, RPS23⁺, RPS3A⁺, RPS8⁺, SARAF⁺, SELL⁺, TC2N⁺, TMSB4X⁺, and TPT1⁺.

In an aspect of the invention, the gene expression profile comprises CD4⁺ and any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or more (or a range of any two of the foregoing values) of AK4⁺, APOBEC3G⁺, C12orf75⁺, CCL5⁺, CD74⁺, CLIC1⁺, COTL1⁺, CST7⁺, CXCL13⁺, CXCR3⁺, DUSP2⁺, EEF1A1⁺, F2R⁺, GAPDH⁺, GNLY⁺, GZMA⁺, GZMK⁺, HCST⁺, HLA-DPA1⁺, LYAR⁺, LYST⁺, MRPL10⁺, MYO1G⁺, NKG7⁺, PABPC1⁺, PDCD1⁺, PFN1⁺, PRF1⁺, RAB27A⁺, RPL10⁺, RPL11⁺, RPL13⁺, RPL18A⁺, RPL19⁺, RPL30⁺, RPL32⁺, RPL34⁺, RPL8⁺, RPL9⁺, RPLP1⁺, RPS12⁺, RPS13⁺, RPS23⁺, RPS3A⁺, RPS8⁺, SARAF⁺, SELL⁺, TC2N⁺, TMSB4X⁺, and TPT1⁺.

In an aspect of the invention, the gene expression profile comprises CD4⁺ and all of AK4⁺, APOBEC3G⁺, C12orf75⁺, CCL5⁺, CD74⁺, CLIC1⁺, COTL1⁺, CST7⁺, CXCL13⁺, CXCR3⁺, DUSP2⁺, EEF1A1⁺, F2R⁺, GAPDH⁺, GNLY⁺, GZMA⁺, GZMK⁺, HCST⁺, HLA-DPA1⁺, LYAR⁺, LYST⁺, MRPL10⁺, MYO1G⁺, NKG7⁺, PABPC1⁺, PDCD1⁺, PFN1⁺, PRF1⁺, RAB27A⁺, RPL10⁺, RPL11⁺, RPL13⁺, RPL18A⁺, RPL19⁺, RPL30⁺, RPL32⁺, RPL34⁺, RPL8⁺, RPL9⁺, RPLP1⁺, RPS12⁺, RPS13⁺, RPS23⁺, RPS3A⁺, RPS8⁺, SARAF⁺, SELL⁺, TC2N⁺, TMSB4X⁺, and TPT1⁺.

In an aspect of the invention, the gene expression profile comprises CD4$^+$ and one or more of AC004585.1$^+$, ACTB$^+$, ACTG1$^+$, ALOX5AP$^+$, ANXA1$^+$, ANXA5$^+$, CD52$^+$, CD99$^+$, CNN2$^+$, COTL1$^+$, FAM45A$^+$, FTH1$^+$, FYB1$^+$, GAPDH$^+$, GIMAP4$^+$, GYPC$^+$, IFITM1$^+$, IFITM2$^+$, IGFBP4$^+$, ITGB1$^+$, LCP1$^+$, LIMS1$^+$, LMO4$^+$, MALAT1$^+$, MIF$^+$, MSN$^+$, MT-ND3$^+$, NDUFA12$^+$, PASK$^+$, PFN1$^+$, PGAM1$^+$, PPP2R5C$^+$, RARRES3$^+$, RILPL2$^+$, RPL30$^+$, RPL32$^+$, RPL34$^+$, RPL9$^+$, RPS13$^+$, RPS25$^+$, RPS3A$^+$, S100A11$^+$, S1PR4$^+$, SERF2$^+$, SLC25A5$^+$, SMC4$^+$, TIMP1$^+$, TMSB4X$^+$, VDAC1$^+$, and ZFP36L2$^+$.

In an aspect of the invention, the gene expression profile comprises CD4$^+$ and any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or more (or a range of any two of the foregoing values) of AC004585.1$^+$, ACTB$^+$, ACTG1$^+$, ALOX5AP$^+$, ANXA1$^+$, ANXA5$^+$, CD52$^+$, CD99$^+$, CNN2$^+$, COTL1$^+$, FAM45A$^+$, FTH1$^+$, FYB1$^+$, GAPDH$^+$, GIMAP4$^+$, GYPC$^+$, IFITM1$^+$, IFITM2$^+$, IGFBP4$^+$, ITGB1$^+$, LCP1$^+$, LIMS1$^+$, LMO4$^+$, MALAT1$^+$, MIF$^+$, MSN$^+$, MT-ND3$^+$, NDUFA12$^+$, PASK$^+$, PFN1$^+$, PGAM1$^+$, PPP2R5C$^+$, RARRES3$^+$, RILPL2$^+$, RPL30$^+$, RPL32$^+$, RPL34$^+$, RPL9$^+$, RPS13$^+$, RPS25$^+$, RPS3A$^+$, S100A11$^+$, S1PR4$^+$, SERF2$^+$, SLC25A5$^+$, SMC4$^+$, TIMP1$^+$, TMSB4X$^+$, VDAC1$^+$, and ZFP36L2$^+$.

In an aspect of the invention, the gene expression profile comprises CD4$^+$ and all of AC004585.1$^+$, ACM ACTG1$^+$, ALOX5AP$^+$, ANXA1$^+$, ANXA5$^+$, CD52$^+$, CD99$^+$, CNN2$^+$, COTL1$^+$, FAM45A$^+$, FTH1$^+$, FYB1$^+$, GAPDH$^+$, GIMAP4$^+$, GYPC$^+$, IFITM1$^+$, IFITM2$^+$, IGFBP4$^+$, ITGB1$^+$, LCP1$^+$, LIMS1$^+$, LMO4$^+$, MALAT1$^+$, MIF$^+$, MSN$^+$, MT-ND3$^+$, NDUFA12$^+$, PASK$^+$, PFN1$^+$, PGAM1$^+$, PPP2R5C$^+$, RARRES3$^+$, RILPL2$^+$, RPL30$^+$, RPL32$^+$, RPL34$^+$, RPL9$^+$, RPS13$^+$, RPS25$^+$, RPS3A$^+$, S100A11$^+$, S1PR4$^+$, SERF2$^+$, SLC25A5$^+$, SMC4$^+$, TIMP1$^+$, TMSB4X$^+$, VDAC1$^+$, and ZFP36L2$^+$.

In an aspect of the invention, any of the gene expression profiles described herein may further comprise one or both of CD25$^-$ and CD127$^-$. Treg cells can be defined by CD25$^+$ CD127$^{lo}$ expression. In this regard, the enriched population of T cells having antigenic specificity for a target antigen may exclude Tregs.

In an aspect of the invention, the gene expression profile comprises one or more of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, H1FX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IFI27L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1F$^+$, MYO1G$^+$, NCK2$^+$, NDUFA7$^+$, NFATC2$^+$, OPTN+, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TLN1$^+$, TMC8$^+$, TMX4$^+$, TOX$^+$, TPM4$^+$, TRAPPC5$^+$, TXN$^+$, UBXN11$^+$, UCP2$^+$, VOPP1$^+$, WNK1$^+$, YWHAE$^+$, and YWHAQ$^+$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, or more (or a range of any two of the foregoing values) of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, H1FX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IFI27L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1F$^+$, MYO1G$^+$, NCK2$^+$, NDUFA7$^+$, NFATC2$^+$, OPTN$^+$, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TLN1$^+$, TMC8$^+$, TMX4$^+$, TOX$^+$, TPM4$^+$, TRAPPC5$^+$, TXN$^+$, UBXN11$^+$, UCP2$^+$, VOPP1$^+$, WNK1$^+$, YWHAE$^+$, and YWHAQ$^+$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or more (or a range of any two of the foregoing values) of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, HIFX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IF127L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1F$^+$, MYO1G$^+$, NCK2$^+$, NDUFA7$^+$, NFATC2$^+$, OPTN$^+$, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TLN1$^+$, TMC8$^+$, TMX4$^+$, TOX+, TPM4$^+$, TRAPPC5$^+$, TXN+, UBXN11$^+$, UCP2$^+$, VOPP1$^+$, WNK1$^+$, YWHAE$^+$, and YWHAQ$^+$. In an aspect of the invention, the gene expression profile comprises all of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, HIFX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IF127L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1F$^+$, MYO1G$^+$, NCK2$^+$, NDUFA7$^+$, NFATC2$^+$, OPTN$^+$, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TLN1$^+$, TMC8$^+$, TMX4$^+$, TOX$^+$, TPM4$^+$, TRAPPC5$^+$, TXN$^+$, UBXN11$^+$, UCP2$^+$, VOPP1$^+$, WNK1$^+$, YWHAE$^+$, and YWHAQ$^+$.

In an aspect of the invention, the gene expression profile comprises one or more of ALOX5AP$^+$, ARID5B$^+$, CCR4$^+$, CD55$^+$, CDKN1B$^+$, COTL1$^+$, CREW, DCXR$^+$, DGKA$^+$, ELOVL5$^+$, EML4$^+$, EZR$^+$, GATA3$^+$, GPR183$^+$, ICAM2$^+$, IL7R$^+$, ISG20$^+$, ITGB1$^+$, ITM2A$^+$, LEF1$^+$, LEPROTL1$^+$, LTB$^+$, NR3C1$^+$, P2RY10$^+$, PASK$^+$, PLP2$^+$, PPP2R5C$^+$, PRKX$^+$, RALA$^+$, RASA3$^+$, RCAN3$^+$, RHBDD2$^+$, RNASET2$^+$, S100A11$^+$, S1PR1$^+$, S1PR4$^+$, SAMHD1$^+$, SAMSN1$^+$, SELL$^+$, SESN3$^+$, SETD2$^+$, SMCHD1$^+$, TMEM123$^+$, TRAT1$^+$, and ZFP36$^+$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more (or a range of any two of the foregoing values) of ALOX5AP$^+$, ARID5B$^+$, CCR4$^+$, CD55$^+$, CDKN1B$^+$, COTL1$^+$, CREW, DCXR$^+$, DGKA$^+$, ELOVL5$^+$, EML4$^+$, EZR$^+$, GATA3$^+$, GPR183$^+$, ICAM2$^+$, IL7R$^+$, ISG20$^+$, ITGB1$^+$, ITM2A$^+$, LEF1$^+$, LEPROTL1$^+$, LTB$^+$, NR3C1$^+$, P2RY10$^+$, PASK$^+$, PLP2$^+$, PPP2R5C$^+$, PRKX$^+$, RALA$^+$, RASA3$^+$, RCAN3$^+$, RHBDD2$^+$, RNASET2$^+$, S100A11$^+$, S1PR1$^+$, S1PR4$^+$, SAMHD1$^+$, SAMSN1$^+$, SELL$^+$, SESN3$^+$, SETD2$^+$, SMCHD1$^+$, TMEM123$^+$, TRAT1$^+$, and ZFP36$^+$. In an aspect of the invention, the gene expression profile comprises all of ALOX5AP$^+$, ARID5B$^+$, CCR4$^+$, CD55$^+$, CDKN1B$^+$, COTL1$^+$, CREM$^+$, DCXR$^+$, DGKA$^+$, ELOVL5$^+$, EML4$^+$, EZR$^+$, GATA3$^+$, GPR183$^+$, ICAM2$^+$, IL7R$^+$, ISG20$^+$, ITGB1$^+$, ITM2A$^+$, LEF1$^+$, LEPROTL1$^+$, LTB$^+$, NR3C1$^+$, P2RY10$^+$, PASK$^+$, PLP2$^+$, PPP2R5C$^+$, PRKX$^+$, RALA$^+$, RASA3$^+$, RCAN3$^+$, RHBDD2$^+$, RNASET2$^+$, S100A11$^+$, S1PR1$^+$, S1PR4$^+$, SAMHD1$^+$, SAMSN1$^+$, SELL$^+$, SESN3$^+$, SETD2$^+$, SMCHD1$^+$, TMEM123$^+$, TRAT1$^+$, and ZFP36$^+$.

In an aspect of the invention, the gene expression profile comprises one or more of ALOX5AP$^+$, ANXA2$^+$, ANXA5$^+$, ARID5B$^+$, CAPN2$^+$, CARS$^+$, CDC25B$^+$, CLDND1$^+$, COTL1$^+$, CREW, CRIP1$^+$, CXCR3$^+$, CYTOR$^+$, DCXR$^+$, EMB$^+$, FBXW5$^+$, FLNA$^+$, GATA3$^+$, HLA-DPA1$^+$, HLA-DPB1$^+$, HLA-DQB1$^+$, HLA-DRA$^+$, HLA-DRB1$^+$, HLA-DRB5$^+$, HNRNPUL1$^+$, ICAM2$^+$, IL10RA$^+$, ISG15$^+$, ISG20$^+$, ITGB1$^+$, ITGB7$^+$, ITM2A$^+$, KLF2$^+$, LGALS3$^+$, MED15$^+$, MX1$^+$, NDUFA12$^+$, NR3C1$^+$, NSMCE1$^+$, P2RY8$^+$, PASK$^+$, PPP2R5C$^+$, RHBDD2$^+$, RNASET2$^+$, S100A11$^+$, S1PR4$^+$, SAMHD1$^+$, SAMSN1$^+$, SELPLG$^+$, SMCHD1$^+$, SPN$^+$, TRADD$^+$, and UBXN11$^+$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or more (or a range of any two of the foregoing values) of ALOX5AP$^+$, ANXA2$^+$, ANXA5$^+$, ARID5B$^+$, CAPN2$^+$, CARS$^+$, CDC25B$^+$, CLDND1$^+$, COTL1$^+$, CREW, CRIP1$^+$, CXCR3$^+$, CYTOR$^+$, DCXR$^+$, EMB$^+$, FBXW5$^+$, FLNA$^+$, GATA3$^+$, HLA-DPA1$^+$, HLA-DPB1$^+$, HLA-DQB1$^+$, HLA-DRA$^+$, HLA-DRB1$^+$, HLA-DRB5$^+$, HNRNPUL1$^+$, ICAM2$^+$, IL10RA$^+$, ISG15$^+$, ISG20$^+$, ITGB1$^+$, ITGB7$^+$, ITM2A$^+$, KLF2$^+$, LGALS3$^+$, MED15$^+$, MX1$^+$, NDUFA12$^+$, NR3C1$^+$, NSMCE1$^+$, P2RY8$^+$, PASK$^+$, PPP2R5C$^+$, RHBDD2$^+$, RNASET2$^+$, S100A11$^+$, S1PR4$^+$, SAMHD1$^+$, SAMSN1$^+$, SELPLG$^+$, SMCHD1$^+$, SPN$^+$, TRADD$^+$, and UBXN11$^+$. In an aspect of the invention, the gene expression profile comprises all of ALOX5AP$^+$, ANXA2$^+$, ANXA5$^+$, ARID5B$^+$, CAPN2$^+$, CAR5$^+$, CDC25B$^+$, CLDND1$^+$, COTL1$^+$, CREW, CRIP1$^+$, CXCR3$^+$, CYTOR$^+$, DCXR$^+$, EMB$^+$, FBXW5$^+$, FLNA$^+$, GATA3$^+$, HLA-DPA1$^+$, HLA-DPB1$^+$, HLA-HLA-DRA$^+$, HLA-DRB1$^+$, HLA-DRB5$^+$, HNRNPUL1$^+$, ICAM2$^+$, IL10RA$^+$, ISG15$^+$, ISG20$^+$, ITGB1$^+$, ITGB7$^+$, ITM2A$^+$, KLF2$^+$, LGALS3$^+$, MED15$^+$, MX1$^+$, NDUFA12$^+$, NR3C1$^+$, NSMCE1$^+$, P2RY8$^+$, PASK$^+$, PPP2R5C$^+$, RHBDD2$^+$, RNASET2$^+$, S100A11$^+$, S1PR4$^+$, SAMHD1$^+$, SAMSN1$^+$, SELPLG$^+$, SMCHD1$^+$, SPN$^+$, TRADD$^+$, and UBXN11$^+$.

In an aspect of the invention, the gene expression profile comprises one or more of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHEL', FLNA$^+$, FYB1$^+$, GATA3$^+$, GNG2$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, OCIAD2$^+$, OPTN+, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, and YWHAB$^+$. For example, the gene expression profile may comprise any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, or more (or a range of any two of the foregoing values) of ALOX5AP$^+$, ANXA2$^+$, ANXA5$^+$, APOBEC3G$^+$, ARHGEF1$^+$, ARID5B$^+$, BIM$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHEL', FLNA$^+$, FYB1$^+$, GATA3$^+$, GNG2$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LIME", LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, and YWHAB$^+$. In an aspect of the invention, the gene expression profile comprises all of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHE1$^+$, FLNA$^+$, FYB1$^+$, GATA3$^+$, GNG2$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, OCIAD2$^+$, OPTN+, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, and YWHAB$^+$.

In an aspect of the invention, the gene expression profile comprises one or more of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHE1$^+$, FBXW5$^+$, FLNA$^+$, FYB1$^+$, GATA3$^+$, GNG2$^+$, GSTK1$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, HNRNPUL1$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, NUDT21$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TGFB1$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, YWHAB$^+$, ANKRD12$^-$, APMAP$^-$, CCL4$^-$, CCL5$^-$, CCR7$^-$, CD48$^-$, CD8B$^-$, CXCR4$^-$, CYTIP$^-$, DARS$^-$, EEF1B2$^-$, EEF1G$^-$, GZMH$^-$, HSP90AB1$^-$, IMPDH2$^-$, ISCU$^-$, LBH$^-$, LINC02446$^-$, LYAR$^-$, MGST3$^-$, MT-ND2$^-$, MT-ND5$^-$, MYC$^-$, NDUFV2$^-$, NFKBIA$^-$, NKG7$^-$, NUCB2$^-$, PDCD4$^-$, PITPNC1$^-$, PLAC8$^-$, PRF1$^-$, PRMT2$^-$, RPL17$^-$, RPS17$^-$, SNHG7$^-$, SNHG8$^-$, STK17A$^-$, TCF7$^-$, TOMM7$^-$, WSB1$^-$, and ZFAS1$^-$.

For example, the gene expression profile may comprise any 1-159 or more (or a range of any two of the foregoing values) of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHEL', FBXW5$^+$, FLNA$^+$, FYB1$^+$, GATA3$^+$, GNG2$^+$, GSTK1$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, HNRNPUL1$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, NUDT21$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TGFB1$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, YWHAB$^+$, ANKRD12$^-$, APMAP$^-$, CCL4$^-$, CCL5$^-$, CCR7$^-$, CD48$^-$, CD8B$^-$, CXCR4$^-$, CYTIP$^-$, DARS$^-$, EEF1B2$^-$, EEF1G$^-$, GZMH$^-$, HSP90AB1$^-$, IMPDH2$^-$, ISCU$^-$, LBH$^-$, LINC02446$^-$, LYAR$^-$, MGST3$^-$, MT-ND2$^-$, MT-ND5$^-$, MYC$^-$, NDUFV2$^-$, NFKBIA$^-$, NKG7$^-$, NUCB2$^-$, PDCD4$^-$, PITPNC1$^-$, PLAC8$^-$, PRF1$^-$, PRMT2$^-$, RPL17$^-$, RPS17$^-$, SNHG7$^-$, SNHG8$^-$, STK17A$^-$, TCF7$^-$, TOMM7$^-$, WSB1$^-$, and ZFAS1$^-$.

In an aspect of the invention, the gene expression profile comprises all of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHEL', FBXW5$^+$, FLNA$^+$, FYB1$^+$, GATA3$^+$, GNG2$^+$, GSTK1$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, HNRNPUL1$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, NUDT21$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TGFB1$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, YWHAB$^+$, ANKRD12$^-$, APMAP$^-$, CCL4$^-$, CCL5$^-$, CCR7$^-$, CD48$^-$, CD8B$^-$, CXCR4$^-$, CYTIP$^-$, DARS$^-$, EEF1B2$^-$, EEF1G$^-$, GZMH$^-$, HSP90AB1$^-$, IMPDH2$^-$, ISCU$^-$, LBH$^-$, LINC02446$^-$, LYAR$^-$, MGST3$^-$, MT-ND2$^-$, MT-ND5$^-$, MYC$^-$, NDUFV2$^-$, NFKBIA$^-$, NKG7$^-$, NUCB2$^-$, PDCD4$^-$, PITPNC1$^-$, PLAC8$^-$, PRF1$^-$, PRMT2$^-$, RPL17$^-$, RPS17$^-$, SNHG7$^-$, SNHG8$^-$, STK17A$^-$, TCF7$^-$, TOMM7$^-$, WSB1$^-$, and ZFAS1$^-$.

In an aspect of the invention, any of the gene expression profiles described herein may further comprise one or both of HAVCR2$^+$ (TIM3)$^+$ and PDCD1$^+$ (PD1$^+$).

Selecting the isolated T cells which have the gene expression profile may comprise detecting the presence or absence of, or measuring the quantity of, the product(s) of expression of the gene(s) in the gene expression profiles described herein. In this regard, selecting the isolated T cells which have the gene expression profile may comprise detecting the presence of protein(s) encoded by positively expressed gene(s) of the gene expression profile. Alternatively or additionally, selecting the isolated T cells which have the gene expression profile may comprise detecting the absence of protein(s) encoded by gene(s) that are negative for expression in the gene expression profile. For example, selecting the isolated T cells which have a gene expression profile may comprise (i) detecting the presence of protein(s) encoded by positively expressed gene(s) of the gene expression profile; and/or (ii) detecting the absence of protein(s) encoded by gene(s) that are negative for expression in the gene expression profile, wherein the gene expression profile comprises one or more of $CARS^+$, $CD39^+$, $CD62L^+$, $CD70^+$, $CD82^+$, $CTLA4^+$, $CXCL13^+$, $HLA\text{-}DRA^+$, $HLA\text{-}DRB1^+$, $ITAGE^+$, $LAG3^+$, $LGALS3^+$, $PDCD1^+$, $SA100A4^+$, $TIGIT^+$, and $TOX^+$. In an aspect of the invention, selecting the isolated T cells which have the gene expression profile comprises detecting the presence and/or absence of cell surface expression of the one or more genes in the gene expression profile. Alternatively or additionally, selecting the isolated T cells which have the gene expression profile may comprise measuring the quantity of protein(s) encoded by gene(s) that are negative for expression in the gene expression profile. Alternatively or additionally, selecting the isolated T cells which have the gene expression profile may comprise measuring the quantity of protein(s) encoded by gene(s) that are positive for expression in the gene expression profile. In an aspect of the invention, selecting the isolated T cells which have the gene expression profile comprises measuring the quantity of cell surface expression of the one or more genes in the gene expression profile. Cell surface expression may be detected or measured by any suitable method, for example, flow cytometry (e.g., fluorescence-activated cell sorting (FACS)).

Alternatively or additionally, selecting the isolated T cells which have the gene expression profile may comprise detecting the presence of RNA encoded by positively expressed gene(s) of the gene expression profile. Alternatively or additionally, selecting the isolated T cells which have the gene expression profile may comprise detecting the absence of RNA encoded by gene(s) that are negative for expression in the gene expression profile. For example, selecting the isolated T cells which have a gene expression profile may comprise (i) detecting the presence of RNA encoded by positively expressed gene(s) of the gene expression profile; and/or (ii) detecting the absence of RNA encoded by gene(s) that are negative for expression in the gene expression profile, wherein the gene expression profile comprises one or more of $ACTG1^+$, $AES^+$, $ANXA2^+$, $ANXA5^+$, $ARPC2^+$, $ARPC3^+$, $CD3D^+$, $CD52^+$, $CD7^+$, $CD62L^+$, $CD99^+$, $CORO1A^+$, $COTL1^+$, $CRIP1^+$, $CXCL13^+$, $EMP3^+$, $FLNA^+$, $FTL^+$, $FYB1^+$, $GAPDH^+$, $H2AFV^+$, $HMGB2^+$, $IL32^+$, $ITGB1^+$, $LSP1^+$, $LTB^+$, $PPIA^+$, $S100A10^+$, $S100A4^+$, $S100A6^+$, $SLC25A5^+$, $TMSB10^+$, $VIM^+$, $ACTB^-$, $B2M^-$, $BTG1^-$, $CCL4^-$, $CCL4L2^-$, $CCL5^-$, $CD74^-$, $EEF1A1^-$, $FTH1^-$, $GZMK^-$, $HLA\text{-}DRA^-$, $MTRNR2L12^-$, $PNRC1^-$, $RPL10^-$, $RPL13^-$, $RPL3^-$, $RPL30^-$, $RPL32^-$, $RPL34^-$, $RPLP1^-$, $RPL39^-$, $RPL5^-$, $RPLP0^-$, $RPS12^-$, $RPS14^-$, $RPS18^-$, $RPS19^-$, $RPS21^-$, $RPS23^-$, $RPS24^-$, $RPS3^-$, $RPS3A^-$, $RPS4X^-$, $RPS6^-$, and $ZC3HAV1^-$. Alternatively or additionally, selecting the isolated T cells which have the gene expression profile may comprise measuring the quantity of RNA encoded by positively expressed gene(s) of the gene expression profile. Alternatively or additionally, selecting the isolated T cells which have the gene expression profile may comprise measuring the quantity of RNA encoded by negatively expressed gene(s) of the gene expression profile.

In an aspect of the invention, the method of preparing an enriched population of T cells having antigenic specificity for a target antigen does not comprise expanding the numbers of the T cells. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.,* 26:332-42 (2003); and Riddell et al., *J. Immunol. Methods,* 128:189-201 (1990). For example, expansion of the numbers of T cells is carried out by culturing the T cells with OKT3 antibody, IL-2, and feeder PBMC (e.g., irradiated allogeneic PBMC). Rare and/or fragile T cells with the desired specificity for a target antigen may be lost during expansion of the numbers of T cells. The inventive methods may, advantageously, prepare an enriched population of T cells having antigenic specificity for the target antigen including such rare and/or fragile T cells by carrying out the inventive methods without expanding the numbers of the T cells.

The method may further comprise separating the selected T cells from the unselected cells, wherein the separated selected T cells provide an enriched population of T cells having antigenic specificity for the target antigen. In this regard, the selected cells may be physically separated from unselected cells, i.e., the cells that do not have the gene expression profile. The selected cells may be separated from unselected cells by any suitable method such as, for example, sorting.

Another aspect of the invention provides a method of isolating a TCR, or an antigen-binding portion thereof, having antigenic specificity for the target antigen.

The "the antigen-binding portion" of the TCR, as used herein, refers to any portion comprising contiguous amino acids of the TCR of which it is a part, provided that the antigen-binding portion specifically binds to the target antigen as described herein with respect to other aspects of the invention. The term "antigen-binding portion" refers to any part or fragment of the TCR of the invention, which part or fragment retains the biological activity of the TCR of which it is a part (the parent TCR). Antigen-binding portions encompass, for example, those parts of a TCR that retain the ability to specifically bind to the target antigen, or detect, treat, or prevent a condition, to a similar extent, the same extent, or to a higher extent, as compared to the parent TCR. In reference to the parent TCR, the functional portion can comprise, for instance, about 10%, 25%, 30%, 50%, 68%, 80%, 90%, 95%, or more, of the parent TCR.

The antigen-binding portion can comprise an antigen-binding portion of either or both of the $\alpha$ and $\beta$ chains of the TCR of the invention, such as a portion comprising one or more of the complementarity determining region (CDR)1, CDR2, and CDR3 of the variable region(s) of the $\alpha$ chain and/or $\beta$ chain of the TCR of the invention. In an aspect of the invention, the antigen-binding portion can comprise the amino acid sequence of the CDR1 of the $\alpha$ chain (CDR1$\alpha$), the CDR2 of the $\alpha$ chain (CDR2$\alpha$), the CDR3 of the $\alpha$ chain (CDR3$\alpha$), the CDR1 of the $\beta$ chain (CDR1$\beta$), the CDR2 of the $\beta$ chain (CDR2$\beta$), the CDR3 of the $\beta$ chain (CDR3$\beta$), or any combination thereof. Preferably, the antigen-binding portion comprises the amino acid sequences of CDR1$\alpha$, CDR2$\alpha$, and CDR3$\alpha$; the amino acid sequences of CDR1$\beta$, CDR2$\beta$, and CDR3$\beta$; or the amino acid sequences of all of CDR1$\alpha$, CDR2$\alpha$, CDR3$\alpha$, CDR1$\beta$, CDR2$\beta$, and CDR3$\beta$ of the inventive TCR.

In an aspect of the invention, the antigen-binding portion can comprise, for instance, the variable region of the inventive TCR comprising a combination of the CDR regions set forth above. In this regard, the antigen-binding portion can comprise the amino acid sequence of the variable region of the α chain (Vα), the amino acid sequence of the variable region of the β chain (Vβ), or the amino acid sequences of both of the Vα and Vβ of the inventive TCR.

In an aspect of the invention, the antigen-binding portion may comprise a combination of a variable region and a constant region. In this regard, the antigen-binding portion can comprise the entire length of the α or β chain, or both of the α and β chains, of the inventive TCR.

The method may comprise preparing an enriched population of T cells having antigenic specificity for the target antigen according to any of the inventive methods described herein with respect to other aspects of the invention.

The method may comprise sorting the T cells in the enriched population into separate single T cell samples and sequencing TCR alpha chain CDR3 and beta chain CDR3 in one or more of the separate single T cell samples. In an aspect of the invention, the sequencing of the TCR alpha chain CDR3 and beta chain CDR3 may be carried out using the single cell transcriptome analysis employed for the analyzing the gene expression profile described herein with respect to other aspects of the invention. Other techniques for sequencing the TCR alpha chain CDR3 and beta chain CDR3 are described at, for example, US 2020/0056237 and WO 2017/048614.

The method may further comprise pairing an alpha chain variable region comprising a CDR3 with a beta chain variable region comprising a CDR3 encoded by the nucleic acid of the separate single T cell samples. In this regard, the method may comprise reconstructing the TCR so that the pairing of the alpha chain variable region comprising a CDR3 with the beta chain variable region comprising a CDR3 yields a functional TCR. In an aspect of the invention, the TCR is reconstructed in silico. Methods of reconstructing the TCR in silico and pairing an alpha chain variable region comprising a CDR3 with a beta chain variable region comprising a CDR3 are described at, for example, US 2020/0056237 and WO 2017/048614.

The method may comprise isolating a nucleotide sequence that encodes the TCR, or the antigen-binding portion thereof, from the selected T cells, wherein the TCR, or the antigen-binding portion thereof, has antigenic specificity for the target antigen.

The method may comprise introducing a nucleotide sequence encoding the paired alpha chain variable region and beta chain variable region into host cells and expressing the paired alpha chain variable region and beta chain variable region by the host cells. Introducing the nucleotide sequence (e.g., a recombinant expression vector) encoding the isolated TCR, or the antigen-binding portion thereof, into host cells may be carried out in any of a variety of different ways known in the art as described in, e.g., Green et al. (Eds.), *Molecular Cloning: A Laboratory Manual*, Cold Spring Harbor Laboratory Press; 4th Ed. (2012). Non-limiting examples of techniques that are useful for introducing a nucleotide sequence into host cells include transformation, transduction, transfection, and electroporation.

In an aspect of the invention, the method may comprise cloning the nucleotide sequence that encodes the TCR, or the antigen-binding portion thereof, into a recombinant expression vector using established molecular cloning techniques as described in, e.g., Green et al., supra. The recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of transposon/transposase, the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector or a lentiviral vector. In an aspect of the invention, the recombinant expression vector is a transposon.

The host cell(s) can be a eukaryotic cell, e.g., plant, animal, fungi, or algae, or can be a prokaryotic cell, e.g., bacteria or protozoa. The host cell(s) can be a cultured cell or a primary cell, i.e., isolated directly from an organism, e.g., a human. The host cell(s) can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating a nucleotide sequence encoding the TCR, or antigen-binding portion thereof, the host cell is preferably a prokaryotic cell, e.g., a DH5α cell. For purposes of producing a recombinant TCR, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a PBMC. More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), TILs, memory T cells (e.g., central memory T cells and effector memory T cells), naïve T cells, and the like.

The method may comprise screening the host cells expressing the paired alpha chain variable region and beta chain variable region for antigenic specificity for the target antigen and selecting the paired alpha chain variable region and beta chain variable region that have antigenic specificity for the target antigen, wherein the TCR, or an antigen-binding portion thereof, having antigenic specificity for the target antigen is isolated. The screening of the host cells for antigenic specificity and selecting the paired alpha chain variable region and beta chain variable region that have antigenic specificity may be carried out using known techniques as described, for example, in US 2017/0218042 and US 2017/0224800.

The TCR, or the antigen-binding portion thereof, isolated by the inventive methods may be useful for preparing cells for adoptive cell therapies. In this regard, an aspect of the invention provides a method of preparing a population of cells that express a TCR, or an antigen-binding portion thereof, having antigenic specificity for a target antigen, the method comprising isolating a TCR, or an antigen-binding portion thereof, as described herein with respect to other aspects of the invention, and introducing the nucleotide sequence encoding the isolated TCR, or the antigen-binding portion thereof, into PBMC to obtain cells that express the TCR, or the antigen-binding portion thereof.

Introducing the nucleotide sequence (e.g., a recombinant expression vector) encoding the isolated TCR, or the antigen-binding portion thereof, into PBMC may be carried out in any of a variety of different ways known in the art as described in, e.g., Green et al. supra. Non-limiting examples of techniques that are useful for introducing a nucleotide sequence into PBMC include transformation, transduction, transfection, and electroporation.

In an aspect of the invention, the method comprises introducing the nucleotide sequence encoding the isolated TCR, or the antigen-binding portion thereof, into PBMC that are autologous to the patient. In this regard, the TCRs, or the antigen-binding portions thereof, identified and isolated by the inventive methods may be personalized to each patient. However, in another aspect, the inventive methods may identify and isolate TCRs, or the antigen-binding portions thereof, that have antigenic specificity against a mutated amino acid sequence that is encoded by a recurrent (also referred to as a "shared mutation") cancer-specific mutation. In this regard, the method may comprise introducing the nucleotide sequence encoding the isolated TCR, or the antigen-binding portion thereof, into PBMC that are allogeneic to the patient. For example, the method may comprise introducing the nucleotide sequence encoding the isolated TCR, or the antigen-binding portion thereof, into the PBMC of another patient whose tumors express the same mutation in the context of the same MHC molecule.

In an aspect of the invention, the PBMC include T cells. The T cells may be any type of T cell, for example, any of those described herein with respect to other aspects of the invention. Without being bound to a particular theory or mechanism, it is believed that less differentiated, "younger" T cells may be associated with any one or more of greater in vivo persistence, proliferation, and antitumor activity as compared to more differentiated, "older" T cells. Accordingly, the inventive methods may, advantageously, identify and isolate a TCR, or an antigen-binding portion thereof, that has antigenic specificity for the target antigen and introduce the TCR, or an antigen-binding portion thereof, into "younger" T cells that may provide any one or more of greater in vivo persistence, proliferation, and antitumor activity as compared to "older" T cells (e.g., effector cells in a patient's tumor) from which the TCR, or the antigen-binding portion thereof, may have been isolated.

In an aspect of the invention, the method of preparing a population of cells that express a TCR, or an antigen-binding portion thereof, further comprises expanding the numbers of PBMC that express the TCR, or the antigen-binding portion thereof. Expanding the numbers of PBMC may be carried out as described herein with respect to other aspects of the invention. In an aspect of the invention, the method of preparing a population of cells that express a TCR, or an antigen-binding portion thereof, comprises expanding the numbers of PBMC that express the TCR, or the antigen-binding portion thereof, while the method of preparing an enriched population of T cells having antigenic specificity for a target antigen does not comprise expanding the numbers of T cells.

Another aspect of the invention provides a TCR, or an antigen-binding portion thereof, isolated by any of the methods described herein with respect to other aspects of the invention. An aspect of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. Another aspect of the invention provides an antigen-binding portion of the TCR comprising one or more CDR regions, one or more variable regions, or one or both of the α and β chains of the TCR, as described herein with respect to other aspects of the invention. The polypeptides of the inventive TCR, or the antigen-binding portion thereof, can comprise any amino acid sequence, provided that the TCR, or the antigen-binding portion thereof, has antigenic specificity for the target antigen.

Another aspect of the invention provides an isolated population of cells prepared according to any of the methods described herein with respect to other aspects of the invention. The population of cells can be a heterogeneous population comprising the PBMC expressing the isolated TCR, or the antigen-binding portion thereof, in addition to at least one other cell, e.g., a host cell (e.g., a PBMC), which does not express the isolated TCR, or the antigen-binding portion thereof, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of PBMC (e.g., consisting essentially of) expressing the isolated TCR, or the antigen-binding portion thereof. The population also can be a clonal population of cells, in which all cells of the population are clones of a single PBMC expressing the isolated TCR, or the antigen-binding portion thereof, such that all cells of the population express the isolated TCR, or the antigen-binding portion thereof. In one aspect of the invention, the population of cells is a clonal population comprising PBMC expressing the isolated TCR, or the antigen-binding portion thereof, as described herein. By introducing the nucleotide sequence encoding the isolated TCR, or the antigen binding portion thereof, into PBMC, the inventive methods may, advantageously, provide a population of cells that comprises a high proportion of PBMC cells that express the isolated TCR and have antigenic specificity for the target antigen. In an aspect of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises PBMC cells that express the isolated TCR and have antigenic specificity for the target antigen. Without being bound to a particular theory or mechanism, it is believed that populations of cells that comprise a high proportion of PBMC cells that express the isolated TCR and have antigenic specificity for the target antigen have a lower proportion of irrelevant cells that may hinder the function of the PBMC, e.g., the ability of the PBMC to target the destruction of target cells and/or treat or prevent a condition. Target cells may include, for example, cancer cells or virus-infected cells.

The inventive TCRs, or the antigen-binding portions thereof, and populations of cells can be formulated into a composition, such as a pharmaceutical composition. In this regard, the invention provides a pharmaceutical composition comprising any of the inventive TCRs, or the antigen-binding portions thereof, or populations of cells and a pharmaceutically acceptable carrier. The inventive pharmaceutical composition can comprise an inventive TCR, or an antigen-binding portion thereof, or population of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR, or the antigen-binding portion thereof, or population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR, the antigen-binding portion thereof, or population of cells, as well as by the particular method used to administer the inventive TCR, the antigen-binding portion thereof, or population of cells. Accordingly, there are a variety of suitable formulations of the pharmaceutical composition of the invention. Suitable formulations may include any of those for oral, intratumoral, parenteral, subcutaneous, intravenous, intramuscular, intraarterial, intrathecal, or interperitoneal administration. More than one route can be used to administer the inventive TCR or population of cells, and in certain instances, a particular route can provide a more immediate and more effective response than another route.

Preferably, the inventive TCR, the antigen-binding portion thereof, or population of cells is administered by injection, e.g., intravenously. When the inventive population of cells is to be administered, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an aspect, the pharmaceutically acceptable carrier is supplemented with human serum albumin.

It is contemplated that the inventive TCRs, the antigen-binding portions thereof, populations of cells, and pharmaceutical compositions can be used in methods of treating or preventing a condition. Without being bound to a particular theory or mechanism, the inventive TCRs, or the antigen-binding portions thereof, are believed to bind specifically to a target antigen, such that the TCR, or the antigen-binding portion thereof, when expressed by a cell, is able to mediate an immune response against a target cell expressing the target antigen. In this regard, the invention provides a method of treating or preventing a condition in a mammal comprising (i) preparing an enriched population of T cells having antigenic specificity for a target antigen according to any of the methods described herein with respect to other aspects of the invention or (ii) preparing an isolated population of cells that express a TCR, or an antigen-binding portion thereof, according to any of the methods described herein with respect to other aspects of the invention; and administering the population of cells to the mammal in an amount effective to treat or prevent the condition in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more signs or symptoms of the condition being treated or prevented. For example, treatment or prevention can include promoting the regression of a tumor. Also, for purposes herein, "prevention" can encompass delaying the onset of the condition, or a symptom, sign, or recurrence thereof.

For purposes of the invention, the amount or dose of the inventive TCR, the antigen-binding portion thereof, population of cells, or pharmaceutical composition administered (e.g., numbers of cells when the inventive population of cells is administered) should be sufficient to effect, e.g., a therapeutic or prophylactic response, in the mammal over a reasonable time frame. For example, the dose of the inventive TCR, the antigen-binding portion thereof, population of cells, or pharmaceutical composition should be sufficient to bind to the target antigen, or detect, treat or prevent a condition in a period of from about 2 hours or longer, e.g., 12 to 24 or more hours, from the time of administration. In certain aspects, the time period could be even longer. The dose will be determined by the efficacy of the particular inventive TCR, the antigen-binding portion thereof, population of cells, or pharmaceutical composition administered and the condition of the mammal (e.g., human), as well as the body weight of the mammal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, or the antigen-binding portion thereof, upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR, the antigen-binding portion thereof, population of cells, or pharmaceutical composition also will be determined by the existence, nature and extent of any adverse side effects that might accompany the administration of a particular inventive TCR, the antigen-binding portion thereof, population of cells, or pharmaceutical composition. Typically, the attending physician will decide the dosage of the inventive TCR, the antigen-binding portion thereof, population of cells, or pharmaceutical composition with which to treat each individual patient, taking into consideration a variety of factors, such as age, body weight, general health, diet, sex, inventive TCR, the antigen-binding portion thereof, population of cells, or pharmaceutical composition to be administered, route of administration, and the severity of the condition being treated.

In an aspect in which the inventive population of cells is to be administered, the number of cells administered per infusion may vary, for example, in the range of one million to 100 billion cells; however, amounts below or above this exemplary range are within the scope of the invention. For example, the daily dose of inventive host cells can be about 1 million to about 150 billion cells (e.g., about 5 million cells, about 25 million cells, about 500 million cells, about 1 billion cells, about 5 billion cells, about 20 billion cells, about 30 billion cells, about 40 billion cells, about 60 billion cells, about 80 billion cells, about 100 billion cells, about 120 billion cells, about 130 billion cells, about 150 billion cells, or a range defined by any two of the foregoing values), preferably about 10 million to about 130 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, about 100 billion cells, about 110 billion cells, about 120 billion cells, about 130 billion cells, or a range defined by any two of the foregoing values), more preferably about 100 million cells to about 130 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, about 50 billion cells, about 75 billion cells, about 90 billion cells, about 100 billion cells, about 110 billion cells, about 120 billion cells, about 130 billion cells, or a range defined by any two of the foregoing values).

For purposes of the inventive methods, wherein populations of cells are administered, the cells can be cells that are allogeneic or autologous to the mammal. Preferably, the cells are autologous to the mammal.

Another aspect of the invention provides a method of preparing a medicament for the treatment or prevention of a condition in a mammal, the method comprising (i) preparing an enriched population of T cells having antigenic specificity for a target antigen according to any of the methods described herein with respect to other aspects of the invention; or (ii) preparing an isolated population of cells that express a TCR, or an antigen-binding portion thereof, according to any of the methods described herein with respect to other aspects of the invention.

In an aspect of the invention, the condition is cancer. The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, chronic lymphocytic leukemia, chronic myeloid cancer, colon cancer, esophageal cancer, uterine cervical cancer, gastric cancer, gastrointestinal carcinoid tumor, glioma, Hodgkin lymphoma, hypopharynx cancer, kidney cancer, larynx cancer, liver cancer, lung cancer (e.g., non-small cell lung cancer), malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. Preferably, the cancer is an epithelial cancer. In an aspect, the cancer is cholangiocarcinoma, melanoma, colon cancer, rectal cancer, breast cancer, lung cancer, anal cancer, esophageal cancer, or gastric cancer.

In an aspect of the invention, the condition is a viral condition. For purposes herein, "viral condition" means a condition that can be transmitted from person to person or from organism to organism, and is caused by a virus. In an aspect of the invention, the viral condition is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, HPV, varicella virus, cytomegalovirus, hepatitis A virus, hepatitis B virus, hepatitis C virus, human immunodeficiency virus (HIV), human T-lymphotropic virus, calicivirus, adenovirus, and Arena virus. In an aspect of the invention, the viral condition may be a chronic viral infection caused by any of the viruses described herein. The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, HPV infection, and mononucleosis. In an aspect of the invention, the viral condition is a viral infection caused by a cancer-associated virus.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). Preferably, the mammals are from the order Artiodactyla, including Bovines (cows) and Swines (pigs) or of the order Perssodactyla, including Equines (horses). Preferably, the mammals are of the order Primates, Ceboids, or Simoids (monkeys) or of the order Anthropoids (humans and apes). A more preferred mammal is the human. In an especially preferred aspect, the mammal is the patient expressing the target antigen.

The following examples further illustrate the invention but, of course, should not be construed as in any way limiting its scope.

Example 1

This example demonstrates the identification of a gene expression profile shared by neoantigen-reactive T cells from the peripheral blood of a colorectal cancer patient, wherein the gene expression profile is identified using tSNE analysis of results of single cell transcriptome analysis.

Figure 1:
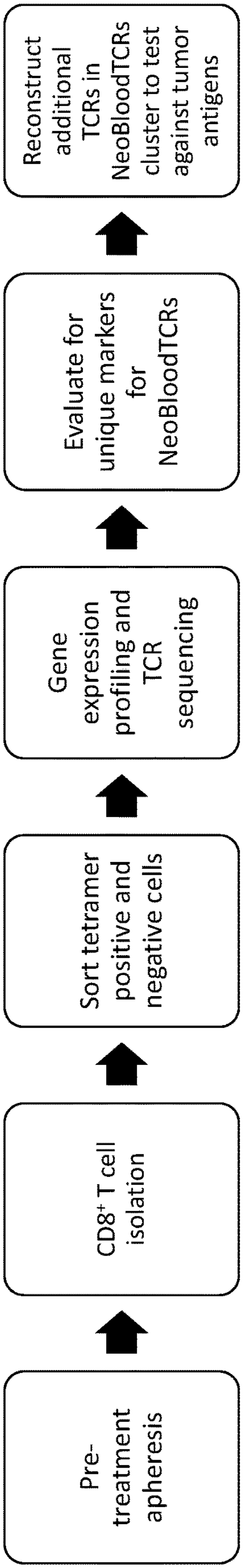
FIG. 1 is a schematic illustrating a strategy for identifying neoantigen-reactive T-cell gene signatures from pre-treatment patient peripheral blood samples using tetramer enrichment of known neoantigen-reactive T cells followed by single-cell analysis according to an aspect of the invention.
Figure 2B:
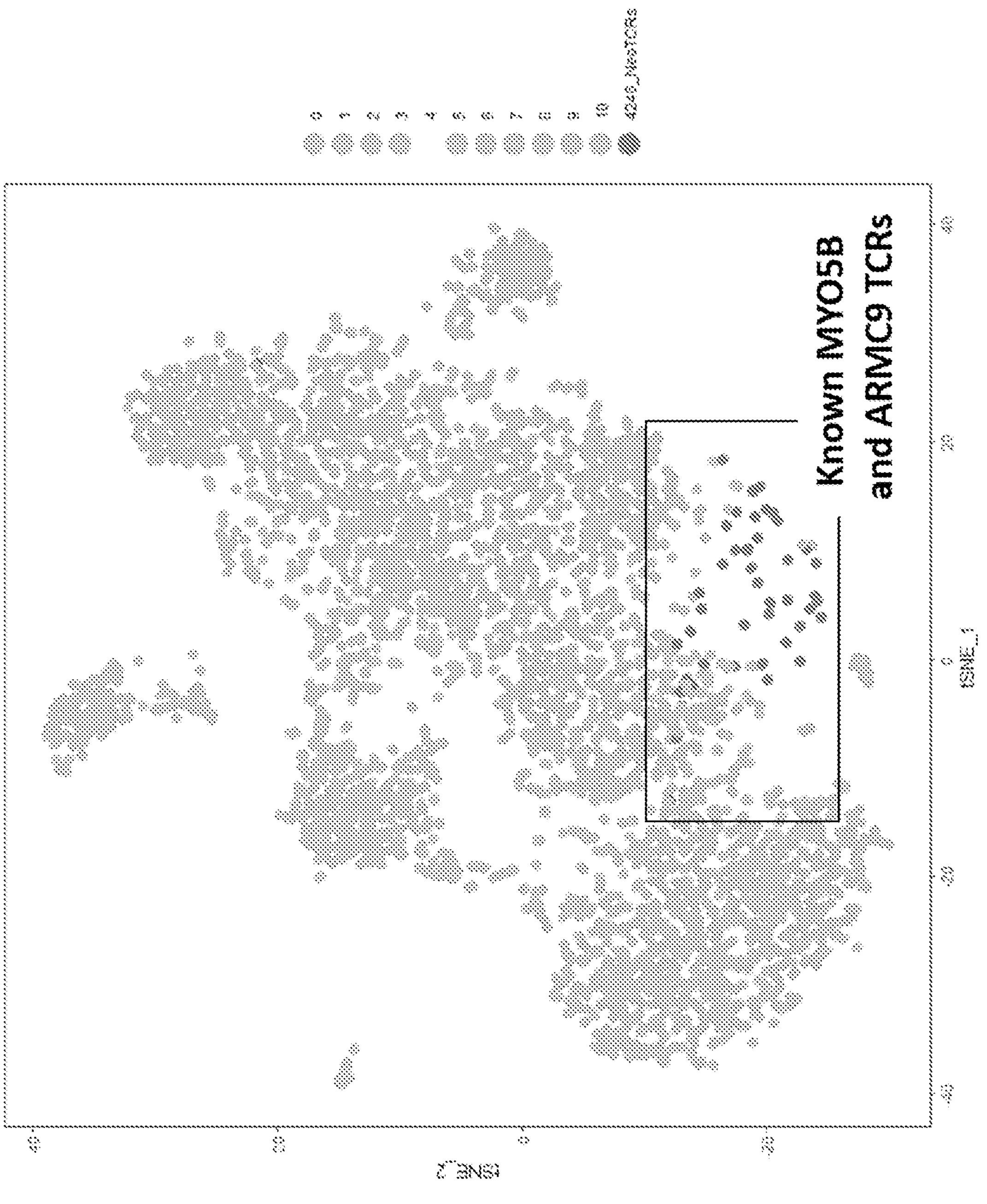
FIG. 2B shows the known neoantigen-reactive TCRs projected onto the t-SNE map of FIG. 2A. The known neoantigen-reactive TCRs localized to cluster 4 (boxed area).

To establish the gene signature, first $CD8^+$ T cells were separated from a blood sample from a colorectal cancer patient (4246) prior to administering ACT to the patient. Next, using staining with HLA tetramers loaded with known neoantigens that were previously identified by tumor fragment functional screening, neoantigen-reactive cells were separated from the remainder of the sample by fluorescence-activated cell sorting (FACS). Sorted neoantigen-reactive cells were then diluted with T cells that were not stained with the tetramer at a 1:10 ratio (neoantigen-reactive:non-reactive) and samples were sent for 10× single-cell transcriptome and TCR sequencing (FIG. 1). The sorting of neoantigen-reactive cells from the blood was carried out to increase the frequency of neoantigen-reactive cells since their frequency in blood can be as low as 1 in $1\times10^6$ T cells. The tetramer negative cells were added to test whether the neoantigen-reactive T cells in the blood display a distinct gene-signature that can separate them from non-neoantigen-reactive cells from the same blood sample (FIGS. 2A-2B). Although HLA tetramers loaded with known neoantigens were used in this experiment to identify the gene expression profiles described herein, it is believed that the gene expression profiles described herein can be used to prepare enriched populations of neoantigen-reactive T cells without having to identify any HLA molecules, neoantigens, or mutations expressed by the patient or adding any tetramer negative cells to the sample.

Two $CD8^+$ T-cell restricted neoantigens (MY05B and ARMC9) were previously identified in colorectal cancer Patient 4246 by a conventional TIL fragment screen. Neoantigen-specific HLA-mutant peptide (pHLA) tetramers were then constructed. pHLA tetramer positive and negative T-cells were sorted in a 1:10 ratio. A combined single-cell analysis of the transcriptome and T-cell receptor (scRNA and scTCR) of T cells from the blood was performed after spiking the tetramer-negative CD8-enriched/separated blood T cells with the two neoantigen-specific tetramers, as outlined in FIG. 1.

tSNE analysis of the scRNA analysis showed different and distinct populations that could be separated into clusters by their gene-signatures (FIG. 2A). Superimposing the known neoantigen-reactive TCR sequences on the tSNE plot showed that the vast majority of the known neoantigen-reactive TCRs were present in cluster 4 (FIG. 2B). This indicated that tumor-reactive neoantigen-specific T cells exhibited a unique transcriptional state that was captured in the pre-treatment blood by single-cell analysis.

Figure 3:
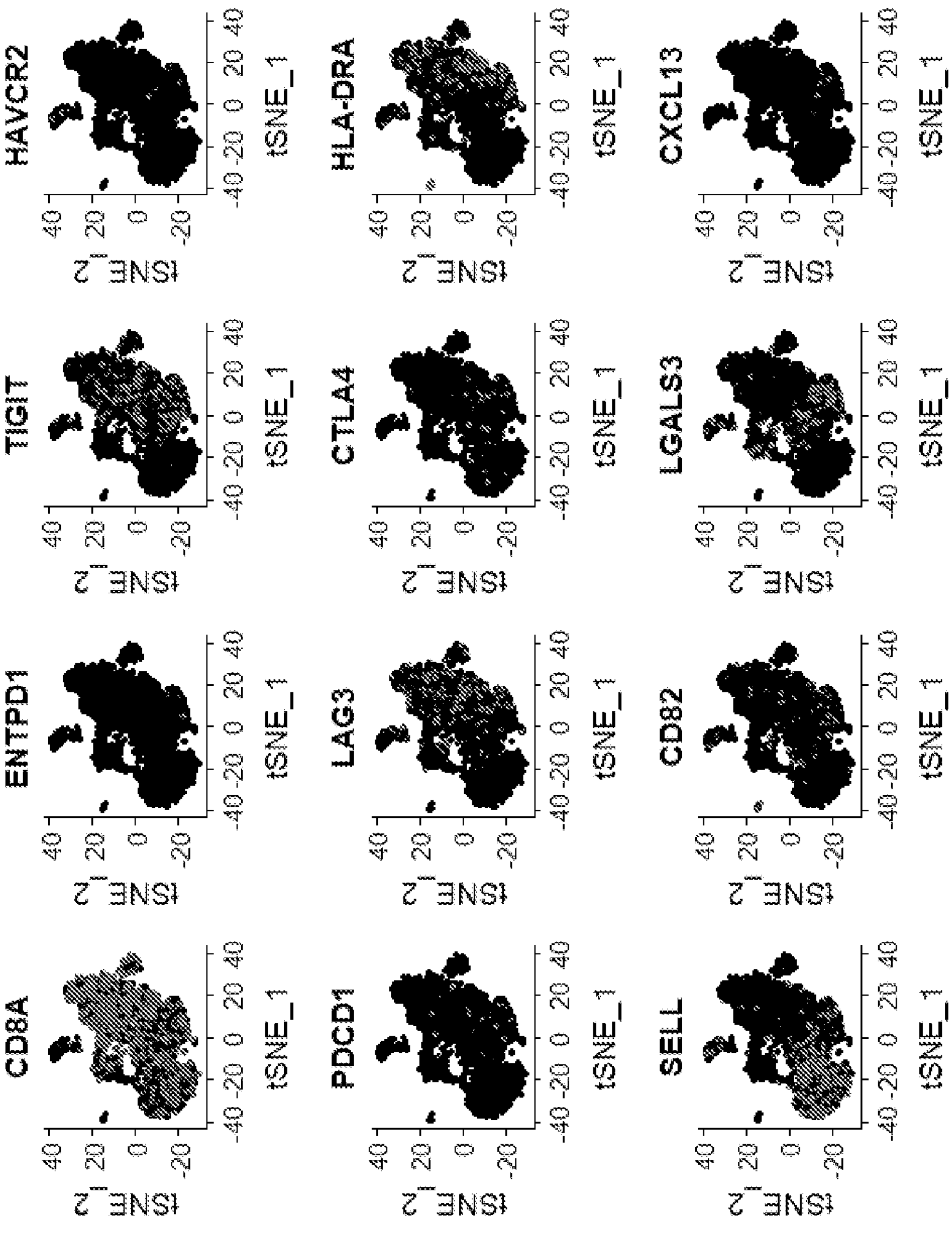
FIG. 3 shows the expression of selected genes by Patient 4246 T cells in cluster 4 of FIG. 2A.

A finer analysis of cluster 4 indicated that cluster 4, with the known neoantigen-specific TCRs, exhibited an activated-dysfunctional signature based on genes upregulated in the cluster e.g., CARS, CD39 (ENTPD1), CD70, CD82, CTLA4, CXCL13, HAVCR2 (TIM3), HLA-DRA, HLA-DRB1, ITAGE, LAG3, LGALS3, PDCD1 (PD-1), SA100A4, TIGIT, and TOX, as well as some memory-related genes like CD62L (SELL) (FIG. 3). The genes described in this Example are the genes that were upregulated in the cluster that contained the majority of reactive cells (enrichment cluster).

Example 2

This example demonstrates the identification of a gene expression profile shared by neoantigen-reactive T cells isolated from the peripheral blood of a colorectal cancer patient, wherein the gene expression profile is identified by comparing the gene expression of the neoantigen-reactive T cells to that of all other cells in the blood sample.

The expression levels of various genes by neoantigen-reactive T cells identified in Example 1 were measured and compared to those of non-neoantigen-reactive T cells in the peripheral blood sample of Patient 4246 using single cell transcriptome analysis.

Table 1A shows the top genes expressed by neoantigen-reactive T cells compared to non-neoantigen-reactive T cells, as measured by differential expression analysis.

Table 1B shows the top genes downregulated by neoantigen-reactive T cells compared to non-neoantigen-reactive T cells, as measured by differential expression analysis.

TABLE 1A

| Gene | avg_log(Fold Change) | Adjusted p value |
|---|---|---|
| ACTG1 | 30.6522572 | 2.01E−20 |
| S100A4 | 25.52500693 | 4.96E−74 |
| CD52 | 14.87771524 | 1.79E−56 |
| EMP3 | 13.88017246 | 2.51E−33 |
| GAPDH | 10.74659868 | 0.003100251 |
| CXCL13 | 10.33849313 | 5.58E−112 |
| TMSB10 | 9.652263397 | 4 64E−44 |
| LSP1 | 9.651328751 | 9.14E−28 |
| FTL | 9.649787321 | 4.55E−10 |
| ANXA5 | 9.144207385 | 1.12E−85 |
| S100A6 | 8.634874557 | 1.64E−66 |
| S100A10 | 8.490069553 | 1.94E−42 |
| LTB | 7.634051009 | 3.40E−13 |
| CD3D | 7.343139595 | 1.17E−18 |
| IL32 | 6.9499957884 | 2.92E−12 |
| VIM | 6.652013675 | 2.06E−20 |
| COTL1 | 6.546139388 | 6.07E−72 |
| FLNA | 5.692650414 | 1.16E−35 |
| ITGB1 | 5.207674077 | 3.51E−75 |
| ANXA2 | 5.059313239 | 5.35E−66 |
| PPIA | 4.941454702 | 0.002528764 |
| SUB1 | 4.438815808 | 2.06E−17 |
| ARPC3 | 4.284581111 | 4.87E−22 |
| CRIP1 | 4.162065543 | 1.35E−34 |
| ARPC2 | 4.102482365 | 1.35E−06 |
| FYB1 | 3.975646347 | 1.23E−20 |

TABLE 1A-continued

| Gene | avg_log(Fold Change) | Adjusted p value |
|---|---|---|
| SELL | 3.871132202 | 8.51E−27 |
| SLC25A5 | 3.852388809 | 9.43E−06 |
| CD99 | 3.697428941 | 1.58E−16 |
| CD7 | 3.693000635 | 5.21E−35 |
| CORO1A | 3.627458905 | 3.41E−29 |
| TIGIT | 3.535538969 | 3.76E−68 |
| HMGB2 | 3.389185552 | 2.32E−10 |
| H2AFV | 3.299578964 | 8.19E−07 |
| AES | 3.298626895 | 2.74E−32 |

TABLE 1B

| Gene | avg_log(Fold Change) | Adjusted p value |
|---|---|---|
| GZMK | −26.26487648 | 5.76E−06 |
| BTG1 | −26.92043022 | 0.000382896 |
| RPS3A | −28.18836463 | 1.95E−11 |
| PNRC1 | −30.172237 | 5.54E−06 |
| RPS14 | −30.34773577 | 8.40E−11 |
| RPL34 | −30.4721558 | 5.19E−10 |
| RPLP1 | −31.04195466 | 0.01169429 |
| RPS19 | −32.34773487 | 1.59E−05 |
| CCL5 | −33.2644597 | 3.89E−24 |
| ZC3HAV1 | −33.78245197 | 2.99E−05 |
| RPS6 | −34.21296323 | 1.94E−05 |
| RPL39 | −35.52218116 | 4.82E−10 |
| CD74 | −36.35987671 | 1.32E−08 |
| RPS21 | −36.78208167 | 8.96E−05 |
| RPL32 | −37.34778201 | 0.001382364 |
| RPL3 | −39.34771011 | 8.85E−24 |
| B2M | −42.34771376 | 8.58E−28 |
| RPL13 | −44.67268817 | 0.041586251 |
| RPLP0 | −47.03380414 | 1.25E−06 |
| ACTB | −47.3477366 | 5.46E−40 |
| RPS23 | −47.3478597 | 0.000200326 |
| RPS12 | −49.35021229 | 7.42E−31 |
| RPS3 | −50.34523778 | 9.12E−09 |
| RPS18 | −50.35016553 | 0.00416526 |
| HLA-DRA | −50.67730801 | 2.92E−27 |
| RPL30 | −53.31020011 | 2.74E−07 |
| RPL5 | −54.17063958 | 1.65E−09 |
| RPS24 | −55.42556516 | 0.007784781 |
| MTRNR2L12 | −59.3477366 | 2.59E−18 |
| RPL10 | −65.34775105 | 7.85E−10 |
| EEF1A1 | −84.3477366 | 1.16E−14 |
| RPS4X | −96.85239234 | 0.000142781 |
| FTH1 | −225.3474009 | 5.88E−26 |
| CCL4 | −303.8802857 | 1.76E−18 |
| CCL4L2 | −524.3477366 | 7.24E−15 |

Example 3

This example demonstrates that the vast majority (93.33%) of the reconstructed TCRs isolated from the T cells identified in cluster 4 of Example 1 specifically recognized one of the two neoantigens expressed by the patient.

Next, 15 different TCRs that were present in cluster 4 were constructed in order to test whether the gene-signature of this cluster can predict neoantigen-reactivity (Table 2A). Table 2A shows the top TCRs of cluster 4 by frequency, excluding known TCRs. All four known TCRs were in the top 19 by frequency in cluster 4. TCRs 1-15 were constructed based on their frequency in the cluster. Previously known neoantigen-reactive TCRs are set forth in Table 2B.

TABLE 2A

| TCR No. | TRAV | TRBV | % of pre-Rx1 pheresis* (CD4 and CD8) | % of 10× (CD8) | Ratio of 10×/pre-Rx pheresis | % of 10× cluster 4 | Ratio of % Cluster 4/% 10× |
|---|---|---|---|---|---|---|---|
| 6 | 38-1 | 10-2 | 0.004619994 | 1.36 | 295 | 12.8 | 9.38 |
| 8 | 8-3 | 4-1 | <0.000001 | 1.28 | 1279899 | 10.41 | 8.14 |
| 1 | 30 | 11-2 | 0.00044423 | 1.01 | 2267 | 8.03 | 7.97 |
| 4 | 25 | 4-3 | <0.000001 | 0.9 | 902224 | 7.16 | 7.93 |
| 2 | 8-3 | 10-3 | 0.002887496 | 0.44 | 153 | 3.69 | 8.37 |
| 5 | 27 | 4-3 | 0.009906334 | 0.36 | 36 | 3.47 | 9.73 |
| 10 | 27 | 3-1 | 0.000710768 | 0.27 | 384 | 2.6 | 9.54 |
| 9 | 3 | 10-3 | <0.000001 | 0.34 | 335711 | 2.6 | 7.75 |
| 11 | 25 | 10-3 | 0.002620958 | 0.31 | 120 | 2.6 | 8.27 |
| 7 | 44046 | 15 | <0.000001 | 0.19 | 188838 | 1.74 | 9.19 |
| 14 | 19 | 2 | 0.000222115 | 2.16 | 9730 | 1.74 | 0.8 |
| 12 | 13-1 | 10-3 | <0.000001 | 0.17 | 167856 | 1.74 | 10.34 |
| 15 | 13-1 | 10-3 | 0.000932883 | 0.13 | 135 | 1.08 | 8.62 |
| 13 | 13-1 | 5-5 | 0.000799614 | 0.13 | 157 | 1.08 | 8.62 |
| 3 | 13-1 | 10-3 | 0.003775957 | 0.27 | 72 | 0.65 | 2.39 |

*Based on TCR sequencing by Adaptive Biotechnology

TABLE 2B

| TRAV | TRBV | % of pre-Rx1 pheresis* (CD4 and CD8) | % of 10× (CD8) | Ratio of 10×/pre-Rx pheresis | % of 10× cluster 4 | Ratio of % Cluster 4/% 10× | Known Reactivity |
|---|---|---|---|---|---|---|---|
| 13-1 | 6-2 | <0.000001 | 0.34 | 335711 | 2.82 | 8.4 | MYO5B |
| 19 | 10-3 | 0.002443266 | 0.29 | 120 | 2.39 | 8.12 | MYO5B |
| 13-1 | 10-3 | <0.000001 | 0.29 | 293747 | 1.95 | 6.65 | MYO5B |
| 14/DV4 | 5-4 | 0.002843073 | 0.1 | 37 | 1.08 | 10.34 | ARMC9 |

*Based on TCR sequencing by Adaptive Biotechnology

For each one of the 15 TCRs, a recombinant expression vector comprising a nucleotide sequence which encoded the TCR was then virally transduced into allogeneic T cells and were stained with tetramers encompassing the known neoantigens. Tetramer with streptavidin conjugated to APC or PE fluorophore was used to sort the cells by FACS based on binding. The use of both fluorophores is more specific since it would be expected that the true TCR would bind to tetramer with either fluorophore, but nonspecific binding generally occurs as only a single positive.

Out of 15 TCRs that were constructed, 14 TCRs (93.33%) showed specific staining to one of the two tetramers (FIG. 4A-4C). Interestingly, TCR No. 14 that did not show staining to either of the tetramers was the only TCR that did not show enrichment in cluster 4 as compared to other clusters (Table 3, FIG. 5). It is estimated that around 68% of the T cells in cluster 4 were neoantigen specific.

TCR-transduced cells (n=50,000) were co-cultured with target Cos7 cells (n=60,000) which had been transfected with 100 ng HLA B40:01 and pulsed with various concentrations or mutant MYO5B, wild-type (WT) MYO5B, mutant ARMC9, or WT ARMC9. The TCR-transduced cell specifically recognized the mutated peptide (FIGS. 6A-6N).

TABLE 3

| TCR No. | TRBV | % of pre-Rx1 pheresis* (CD4 and CD8) | % of 10× (CD8) | Ratio of 10×/pre-Rx pheresis | % of 10× cluster 4 | Ratio of % Cluster 4/% 10× | Known Reactivity |
|---|---|---|---|---|---|---|---|
| 6 | 10-2 | 0.004619994 | 1.36 | 295 | 12.8 | 9.38 | MYO5B |
| 8 | 4-1 | <0.000001 | 1.28 | 1279899 | 10.41 | 8.14 | ARMC9 |
| 1 | 11-2 | 0.00044423 | 1.01 | 2267 | 8.03 | 7.97 | ARMC9 |
| 4 | 4-3 | <0.000001 | 0.9 | 902224 | 7.16 | 7.93 | ARMC9 |
| 2 | 10-3 | 0.002887496 | 0.44 | 153 | 3.69 | 8.37 | MYO5B |
| 5 | 4-3 | 0.009906334 | 0.36 | 36 | 3.47 | 9.73 | ARMC9 |
| 10 | 3-1 | 0.000710768 | 0.27 | 384 | 2.6 | 9.54 | ARMC9 |
| 9 | 10-3 | <0.000001 | 0.34 | 335711 | 2.6 | 7.75 | MYO5B |
| 11 | 10-3 | 0.002620958 | 0.31 | 120 | 2.6 | 8.27 | MYO5B |
| 7 | 15 | <0.000001 | 0.19 | 188838 | 1.74 | 9.19 | MYO5B |
| 14 | 2 | 0.000222115 | 2.16 | 9730 | 1.74 | 0.8 | |
| 12 | 10-3 | <0.000001 | 0.17 | 167856 | 1.74 | 10.34 | MYO5B |
| 15 | 10-3 | 0.000932883 | 0.13 | 135 | 1.08 | 8.62 | MYO5B |
| 13 | 5-5 | 0.000799614 | 0.13 | 157 | 1.08 | 8.62 | MYO5B |
| 3 | 10-3 | 0.003775957 | 0.27 | 72 | 0.65 | 2.39 | MYO5B |

*Based on TCR sequencing by Adaptive Biotechnology

The data obtained in Examples 1-3 indicated the following conclusions:

1. Neo-antigen specific T-cells in the blood expressed a unique transcriptional signature that was captured by scRNA (FIG. 3, Tables 1A-1B);

2. Reconstruction of other unknown TCRs from the same transcriptional module captured 14 additional TCRs which recognized the same two neo-antigens (FIG. 4A-4C, Table 3); and 3. Identifying and reconstructing patient tumor-specific neo-antigen reactive TCRs from pre-treatment blood is feasible using high dimensional analysis.

Prior attempts to isolate neo-antigen specific TCRs from patient blood has historically been difficult due to very low precursor frequencies of these T-cells as well as the lack of accurate approaches that can determine phenotypic markers of these cells from the blood. The inventive methods provide a platform for identifying and potentially isolating tumor-specific TCRs prior to their tumor resections, providing a unique opportunity to employ less invasive immunotherapy regimens.

Example 4

This example demonstrates the identification of a comprehensive gene expression profile shared by neoantigen-reactive T cells from the peripheral blood of three cancer patients, wherein the gene expression profile is identified using tSNE analysis of results of single cell transcriptome analysis. This example also demonstrates the identification of a comprehensive gene expression profile shared by EBV-reactive T cells from the peripheral blood of a cancer patient, wherein the gene expression profile is identified using tSNE analysis of results of single cell transcriptome analysis.

The methods described in Examples 1-3 were carried out for two additional metastatic cancer patients 4287 (colon cancer) and 4317 (rectal cancer). The analysis provided a comprehensive gene-signature from samples from a total of three patients, namely patients 4287 and 4317 and patient 4246. Patient 4246 was analyzed in Examples 1-3.

Patient 4287 was also positive for Epstein-Barr virus (EBV). The methods described in Examples 1-3 were also carried out with respect to the EBV-reactive T cells for Patient 4287.

tSNE analysis of the scRNA analysis showed different and distinct populations that could be separated into clusters by their gene-signatures (FIG. 7A). Superimposing the known neoantigen-reactive TCR sequences (and the EBV-reactive TCR sequences for Patient 4287) on the tSNE plot showed that the vast majority of the known neoantigen-reactive TCRs (and the EBV-reactive TCR sequences) were present in cluster 9 (FIG. 7B).

The expression levels of various genes by neoantigen-reactive T cells identified in this example were measured and compared to those of non-neoantigen-reactive T cells in the peripheral blood sample of Patients 4246, 4287, and 4317 using single cell transcriptome analysis.

Table 4A shows the top genes expressed by neoantigen-reactive T cells compared to non-neoantigen-reactive T cells, as measured by differential expression analysis.

Table 4B shows the top genes downregulated by neoantigen-reactive T cells compared to non-neoantigen-reactive T cells, as measured by differential expression analysis.

The gene expression by peripheral blood CD8$^{+}$ T cells of Patients 4246, 4287, and 4317 was examined to determine how close the gene expression profile of each cell was to the gene expression profile identified in Tables 4A-4B. The top 95th percentile of those cells exhibiting the closest gene expression profile to that identified in Tables 4A-4B were identified (FIG. 8). The gene expression profile of the top 95th percentile of those cells exhibiting the closest gene expression profile to that identified in Tables 4A-4B is set forth below in Table 5.

TABLE 4A

| | average_logFoldChange | p_val_adj |
|---|---|---|
| CHN1 | 1.329457827 | 2.69E−240 |
| CLECL1 | 1.131774123 | 6.73E−170 |
| PASK | 0.934654095 | 1.33E−90 |
| UBXN11 | 0.850500271 | 1.00E−49 |
| LGALS3 | 0.847532241 | 1.76E−57 |
| ITGB1 | 0.84060359 | 1.92E−72 |
| LIME1 | 0.809077933 | 3.47E−52 |
| TIGIT | 0.788510988 | 4.07E−58 |
| HLA-DRA | 0.767792393 | 2.63E−53 |
| ALOX5AP | 0.76567169 | 9.06E−69 |
| MYO1G | 0.755746764 | 6.73E−50 |
| HLA-DRB1 | 0.755026591 | 1.63E−57 |
| HLA-DRB5 | 0.74306221 | 2.04E−69 |
| CD82 | 0.737838016 | 1.56E−44 |
| CDC25B | 0.733458585 | 4.58E−42 |
| ANXA5 | 0.728110042 | 1.35E−50 |
| ANXA2 | 0.709044305 | 3.46E−41 |
| FLNA | 0.653976427 | 1.83E−32 |
| P2RY8 | 0.637695424 | 1.39E−26 |
| GATA3 | 0.631822721 | 1.50E−17 |
| HLA-DQA2 | 0.625146226 | 7.80E−61 |
| ITM2A | 0.596488637 | 4.80E−49 |
| TPM4 | 0.594495731 | 9.82E−21 |
| HLA-DPA1 | 0.581726611 | 2.53E−47 |
| COTL1 | 0.574193576 | 2.56E−44 |
| S100A11 | 0.558325899 | 5.33E−44 |
| RBPJ | 0.550035019 | 3.13E−17 |
| HLA-DQB1 | 0.536435972 | 1.69E−32 |
| CYTOR | 0.53382937 | 2.71E−22 |
| TRADD | 0.533499295 | 7.73E−15 |
| CARS | 0.53280646 | 5.61E−31 |

TABLE 4B

| | average_logFoldChange | p_val_adj |
|---|---|---|
| LINC02446 | −0.450046699 | 1.45E−05 |
| IMPDH2 | −0.471567915 | 9.42E−06 |
| CYTIP | −0.502345494 | 1.54E−14 |
| NUCB2 | −0.505172439 | 6.44E−08 |
| EEF1G | −0.562848342 | 4.20E−15 |
| MYC | −0.564363277 | 6.22E−06 |
| CCL5 | −0.576868426 | 2.30E−17 |
| CCR7 | −0.582681624 | 7.45E−16 |
| LYAR | −0.596306859 | 1.45E−09 |
| PITPNC1 | −0.644586391 | 1.16E−09 |
| TCF7 | −0.661697531 | 2.60E−15 |
| CCL4 | −0.738902905 | 9.16E−11 |
| PLAC8 | −0.841351385 | 1.26E−13 |
| NKG7 | −0.917748154 | 5.11E−29 |
| GZMH | −1.037027439 | 1.73E−17 |

Alternative gene expression profiles identified in this Example are set forth in Table 4C.

TABLE 4C

| Alternative 1 (cluster 9) (upregulated) | Alternative 2 (All neoantigen reactive with cluster 9) (upregulated) | Alternative 3 (Neoantigen reactive without cluster 9) | |
|---|---|---|---|
| ALOX5AP | ALOX5AP | ALOX5AP | Upregulated in Neoantigen clones |
| ANXA2 | ANXA2 | ANXA2 | |
| ANXA5 | ANXA5 | ANXA5 | |

TABLE 4C-continued

| Alternative 1 (cluster 9) (upregulated) | Alternative 2 (All neoantigen reactive with cluster 9) (upregulated) | Alternative 3 (Neoantigen reactive without cluster 9) |
|---|---|---|
| ARID5B | APOBEC3G | APOBEC3G |
| CAPN2 | ARHGEF1 | ARHGEF1 |
| CARS | ARID5B | ARID5B |
| CDC25B | BIN1 | BIN1 |
| CLDND1 | BIN2 | BIN2 |
| COTL1 | C12orf75 | C12orf75 |
| CREM | C4orf48 | C4orf48 |
| CRIP1 | CAMK4 | CAMK4 |
| CXCR3 | CAPN2 | CAPN2 |
| CYTOR | CAPZB | CAPZB |
| DCXR | CARD16 | CARD16 |
| EMB | CARS | CARS |
| FBXW5 | CCNDBP1 | CCNDBP1 |
| FLNA | CD5 | CD5 |
| GATA3 | CD55 | CD55 |
| HLA-DPA1 | CD82 | CD82 |
| HLA-DPB1 | CDC25B | CDC25B |
| HLA-DQB1 | CHN1 | CHN1 |
| HLA-DRA | CLECL1 | CLECL1 |
| HLA-DRB1 | CNN2 | CNN2 |
| HLA-DRB5 | CORO1B | CORO1B |
| HNRNPUL1 | COTL1 | COTL1 |
| ICAM2 | CRIP1 | CRIP1 |
| IL10RA | CYTOR | CYTOR |
| ISG15 | DCXR | DCXR |
| ISG20 | DYNLL1 | DYNLL1 |
| ITGB1 | DYNLT1 | DYNLT1 |
| ITGB7 | EID1 | EID1 |
| ITM2A | EIF3A | EIF3A |
| KLF2 | ELOVL5 | ELOVL5 |
| LGALS3 | EMB | EMB |
| LIME1 | ETHE1 | ETHE1 |
| MED15 | FLNA | FBXW5 |
| MX1 | FYB1 | FLNA |
| NDUFA12 | GATA3 | FYB1 |
| NR3C1 | GNG2 | GATA3 |
| NSMCE1 | HLA-DPA1 | GNG2 |
| P2RY8 | HLA-DPB1 | GSTK1 |
| PASK | HLA-DQA2 | HLA-DPA1 |
| PPP2R5C | HLA-DQB1 | HLA-DPB1 |
| RHBDD2 | HLA-DRA | HLA-DQA2 |
| RNASET2 | HLA-DRB1 | HLA-DQB1 |
| S100A11 | HLA-DRB5 | HLA-DRA |
| S1PR4 | ICAM2 | HLA-DRB1 |
| SAMHD1 | ICAM3 | HLA-DRB5 |
| SAMSN1 | IL10RA | HNRNPUL1 |
| SELPLG | IRF7 | ICAM2 |
| SMCHD1 | ISG15 | ICAM3 |
| SPN | ISG20 | IL10RA |
| TIGIT | ITGAE | IRF7 |
| TRADD | ITGB1 | ISG15 |
| UBXN11 | ITGB7 | ISG20 |
| | ITM2A | ITGAE |
| | KLF2 | ITGB1 |
| | LGALS3 | ITGB7 |
| | LIME1 | ITM2A |
| | LY6E | KLF2 |
| | MAD1L1 | LGALS3 |
| | MED15 | LIME1 |
| | MFNG | LY6E |
| | MTERF4 | MAD1L1 |
| | MX1 | MED15 |
| | MYO1G | MFNG |
| | NDUFA12 | MTERF4 |
| | NDUFB9 | MX1 |
| | NELL2 | MYO1G |
| | NR3C1 | NDUFA12 |
| | OCIAD2 | NDUFB9 |
| | OPEN | NELL2 |
| | P2RY8 | NR3C1 |
| | PARP1 | NUDT21 |
| | PASK | OCIAD2 |
| | PLP2 | OPTN |
| | PPP1R7 | P2RY8 |
| | PPP2R5C | PARP1 |

TABLE 4C-continued

| Alternative 1 (cluster 9) (upregulated) | Alternative 2 (All neoantigen reactive with cluster 9) (upregulated) | Alternative 3 (Neoantigen reactive without cluster 9) | |
|---|---|---|---|
| | PSMB2 | PASK | |
| | PSTPIP1 | PLP2 | |
| | PYCARD | PPP1R7 | |
| | RBPJ | PPP2R5C | |
| | RHBDD2 | PSMB2 | |
| | RNASEH2B | PSTPIP1 | |
| | RNASET2 | PYCARD | |
| | S100A11 | RBPJ | |
| | S100A4 | RHBDD2 | |
| | S1PR4 | RNASEH2B | |
| | SAMSN1 | RNASET2 | |
| | SELPLG | S100A11 | |
| | SH3KBP1 | S100A4 | |
| | SHMT2 | S1PR4 | |
| | SIT1 | SAMSN1 | |
| | SMCHD1 | SELPLG | |
| | SPN | SH3KBP1 | |
| | STK38 | SHMT2 | |
| | SYTL1 | SIT1 | |
| | SYTL3 | SMCHD1 | |
| | TAGAP | SPN | |
| | TBC1D10C | STK38 | |
| | TIGIT | SYTL1 | |
| | TMPO | SYTL3 | |
| | TMX4 | TAGAP | |
| | TPGS1 | TBC1D10C | |
| | TPM4 | TGFB1 | |
| | TRADD | TIGIT | |
| | TSPO | TMPO | |
| | TXN | TMX4 | |
| | UBE2L6 | TPGS1 | |
| | UBXN11 | TPM4 | |
| | UCP2 | TRADD | |
| | YWHAB | TSPO | |
| | | TXN | |
| | | UBE2L6 | |
| | | UBXN11 | |
| | | UCP2 | |
| | | YWHAB | |
| | | ANKRD12 | Downregulated in Neoantigen clones |
| | | APMAP | |
| | | CCL4 | |
| | | CCL5 | |
| | | CCR7 | |
| | | CD48 | |
| | | CD8B | |
| | | CXCR4 | |
| | | CYTIP | |
| | | DARS | |
| | | EEF1B2 | |
| | | EEF1G | |
| | | GZMH | |
| | | HSP90AB1 | |
| | | IMPDH2 | |
| | | ISCU | |
| | | LBH | |
| | | LINC02446 | |
| | | LYAR | |
| | | MGST3 | |
| | | MT-ND2 | |
| | | MT-ND5 | |
| | | MYC | |
| | | NDUFV2 | |
| | | NFKBIA | |
| | | NKG7 | |
| | | NUCB2 | |
| | | PDCD4 | |
| | | PITPNC1 | |
| | | PLAC8 | |
| | | PRF1 | |
| | | PRMT2 | |
| | | RPL17 | |
| | | RPS17 | |
| | | SNHG7 | |
| | | SNHG8 | |

TABLE 4C-continued

| Alternative 1 (cluster 9) (upregulated) | Alternative 2 (All neoantigen reactive with cluster 9) (upregulated) | Alternative 3 (Neoantigen reactive without cluster 9) |
|---|---|---|
| | | STK17A |
| | | TCF7 |
| | | TOMM7 |
| | | WSB1 |
| | | ZFAS1 |

TABLE 5

| | | |
|---|---|---|
| $ALOX5AP^+$ | $COTL1^+$ | $ITGB1^+$ |
| $ANXA2^+$ | $FLNA^+$ | $ITM2A^+$ |
| $ANXA5^+$ | $HLA\text{-}DPA1^+$ | $LGALS3^+$ |
| $CARS^+$ | $HLA\text{-}DQA2^+$ | $LIME1^+$ |
| $CD82^+$ | $HLA\text{-}DQB1^+$ | $MYO1G^+$ |
| $CDC25B^+$ | $HLA\text{-}DRA^+$ | $PASK^+$ |
| $CHN1^+$ | $HLA\text{-}DRB1^+$ | $S100A11^+$ |
| $CLECL1^+$ | $HLA\text{-}DRB5^+$ | $TIGIT^+$ |
| | | $UBXN11^+$ |

Example 5

This example demonstrates the detection of neoantigen-reactive TCRs from a pre-treatment blood sample of Patient 4246 by FACS-sorting $CD39^+CD103^+$-expressing cells.

Based on the single-cell sequencing results of Example 4, a method to sort-enrich neoantigen-reactive T cells based on the expression of surface markers on activated memory T cells in the blood (e.g. $CD39^+CD103^+$, $CD39^+$ $TIGIT^+$, $CD39^+PD\text{-}1^+$) was developed.

$CD8^+$ cells from a pre-treatment blood sample of Patient 4246 were sorted based on the expression of $CD45RO^+$ $CD45RA^-HLA\text{-}DR^+$ and the co-expression of CD39 and CD103 and subjected to TCR sequencing. The frequencies of known neoantigen-reactive TCRs in the sorted population as compared to their frequencies in a bulk pre-treatment blood sample are shown in Table 6 (N.D—not detected, N/A—not applicable).

TABLE 6

| Target neoantigen | Frequency in Bulk CD3 | Frequency in $CD39^+CD103^+$ | Fold enrichment ($CD39^+$ $CD103^+$/ Bulk CD3) |
|---|---|---|---|
| $ARMC9^{L146F}$ | 4.44E−06 | 0.0077 (1/131) | 1718 |
| $MYO5B^{K1410Q}$ | 2.89E−05 | 0.077 (10/131) | 2644 |
| $MYO5B^{K1410Q}$ | 3.78E−05 | 0.046 (6/131) | 1213 |
| $ARMC9^{L146F}$ | N.D. | 0.015 (2/131) | N/A |
| $ARMC9^{L146F}$ | 9.91E−05 | 0.015 (2/131) | 154 |
| $MYO5B^{K1410Q}$ | 4.62E−05 | 0.023 (3/131) | 496 |
| $MYO5B^{K1410Q}$ | N.D. | N.D. | N/A |
| $ARMC9^{L146F}$ | 9.77E−06 | 0.0077 (1/131) | 781 |
| $MYO5B^{K1410Q}$ | N.D. | 0.046 (6/131) | N/A |
| $ARMC9^{L146F}$ | 7.11E−06 | 0.015 (2/131) | 2148 |
| $MYO5B^{K1410Q}$ | 2.62E−05 | 0.084 (11/131) | 3204 |
| $MYO5B^{K1410Q}$ | N.D. | N.D. | N/A |
| $MYO5B^{K1410Q}$ | 8.00E−06 | 0.031 (4/131) | 3819 |
| $MYO5B^{K1410Q}$ | 9.33E−06 | 0.0077 (1/131) | 818 |
| $MYO5B^{K1410Q}$ | 2.44E−03 | 0.11 (14/131) | 44 |
| $MYO5B^{K1410Q}$ | N.D. | 0.0077 (1/131) | N/A |
| $MYO5B^{K1410Q}$ | N.D. | 0.061 (8/131) | N/A |
| $ARMC9^{L146F}$ | 0.002843073 | N.D. | N/A |
| Total | 5.56E−03 | 0.549618321 | |

Example 6

This example demonstrates the detection of HPV-reactive $CD8^+$ T cells from the peripheral blood of a metastatic $HPV^+$ anal cancer patient.

$CD8^+$ T cells expressing $CD39^+CD103^+$ (gated through $CD8^+CD45RO^+CD45RA^-HLA\text{-}DR^+$) were sorted from a blood sample of a metastatic $HPV^+$ anal cancer patient. The sorted cells were enriched for HPV-reactive $CD8^+$ T cells. The frequencies of known HPV-reactive TCRs in the sorted population were compared to their frequencies in a bulk pre-treatment blood sample as described in Example 5. The frequency of HPV-reactive clone was 4% (4/96) in the sorted subset and 0.2% in the blood.

Example 7

This example demonstrates the detection of neoantigen-reactive $CD4^+$ T cell receptors from a pre-treatment blood sample of colorectal cancer patient 4400 by FACS-sorting $CD39^+$-expressing cells.

The enrichment strategy of $CD4^+$ cells is illustrated in FIG. 9A. Briefly, similar to the approach that was used in Examples 1-3 for $CD8^+$ T cells, neoantigen-reactive $CD4^+$ T cells co-expressing HLA-DR and CD39 were sorted and mixed with bulk $CD4^+$ T cells (1:1 ratio). This mixture was sent for 10× single-cell transcriptome and TCR sequencing. Since the availability and reliability of tetramers against $CD4^+$ TCRs were limited, neoantigen-reactive $CD4^+$ T cells were enriched by FACS-sorting $CD4^+CD45RO^+CD45RA^-$ $HLA\text{-}DR^+CD39^+$-expressing cells, based on the $CD8^+$ results and the assumption that neoantigen-reactive $CD4^+$ cells express an activated memory phenotype (FIG. 9B).

Based on Uniform Manifold Approximation and Projection (UMAP) analysis, previously known reactive clones were predominantly present in clusters 7 and 12 (FIGS. 9B-9C). A table of genes that were significantly upregulated in these clusters was generated (Table 7). Genes in Table 7 overlapped with the gene signature that was generated for $CD8^+$ cells.

Next, it was tested whether the gene signature can capture the known-reactive clones and the putative neoantigen-reactive clusters. The analysis showed that the gene signature can be used for $CD4^+$ cells and was able to capture the putative neoantigen-reactive clusters (FIG. 9D). Notably, among cells that showed high expression (90th percentile) of the gene signature was a subset of $CD4^+$ Treg cells. These cells can be removed bioinformatically (FIGS. 9E-9F) and can be excluded from FACS-sorting using CD25 and CD127 surface markers (e.g., $CD25^-$ and $CD127^-$) (Treg cells can be defined by $CD25^+CD127^{lo}$ expression).

TABLE 7

| Cluster 12 | Cluster 7 |
|---|---|
| $AK4^+$ | $AC004585.1^+$ |
| $APOBEC3G^+$ | $ACTB^+$ |
| $C12orf75^+$ | $ACTG1^+$ |
| $CCL5^+$ | $ALOX5AP^+$ |
| $CD74^+$ | $ANXA1^+$ |
| $CLIC1^+$ | $ANXA5^+$ |
| $COTL1^+$ | $CD52^+$ |
| $CST7^+$ | $CD99^+$ |
| $CXCL13^+$ | $CNN2^+$ |
| $CXCR3^+$ | $COTL1^+$ |
| $DUSP2^+$ | $FAM45A^+$ |
| $EEF1A1^+$ | $FTH1^+$ |
| $F2R^+$ | $FYB1^+$ |

TABLE 7-continued

| Cluster 12 | Cluster 7 |
|---|---|
| GAPDH$^+$ | GAPDH$^+$ |
| GNLY$^+$ | GIMAP4$^+$ |
| GZMA$^+$ | GYPC$^+$ |
| GZMK$^+$ | IFITM1$^+$ |
| HCST$^+$ | IFITM2$^+$ |
| HLA-DPA1$^+$ | IGFBP4$^+$ |
| LYAR$^+$ | ITGB1$^+$ |
| LYST$^+$ | LCP1$^+$ |
| MRPL10$^+$ | LIMS1$^+$ |
| MYO1G$^+$ | LMO4$^+$ |
| NKG7$^+$ | MALAT1$^+$ |
| PABPC1$^+$ | MIF$^+$ |
| PDCD1$^+$ | MSN$^+$ |
| PFN1$^+$ | MT-ND3$^+$ |
| PRF1$^+$ | NDUFA12$^+$ |
| RAB27A$^+$ | PASK$^+$ |
| RPL10$^+$ | PFN1$^+$ |
| RPL11$^+$ | PGAM1$^+$ |
| RPL13$^+$ | PPP2R5C$^+$ |
| RPL18A$^+$ | RARRES3$^+$ |
| RPL19$^+$ | RILPL2$^+$ |
| RPL30$^+$ | RPL30$^+$ |
| RPL32$^+$ | RPL32$^+$ |
| RPL34$^+$ | RPL34$^+$ |
| RPL8$^+$ | RPL9$^+$ |
| RPL9$^+$ | RPS13$^+$ |
| RPLP1$^+$ | RPS25$^+$ |
| RPS12$^+$ | RPS3A$^+$ |
| RPS13$^+$ | S100A11$^+$ |
| RPS23$^+$ | S1PR4$^+$ |
| RPS3A$^+$ | SERF2$^+$ |
| RPS8$^+$ | SLC25A5$^+$ |
| SARAF | SMC4$^+$ |
| SELL$^+$ | TIMP1$^+$ |
| TC2N$^+$ | TMSB4X$^+$ |
| TMSB4X$^+$ | VDAC1$^+$ |
| TPT1$^+$ | ZFP36L2$^+$ |

Example 8

This example demonstrates the detection of neoantigen-reactive CD8$^+$ T cells from pre-treatment blood samples of three additional metastatic gastrointestinal cancer patients by FACS-sorting cells based on cell surface markers.

To test the method, neoantigen-reactive CD8$^+$ T cells were cell enriched from three additional metastatic gastrointestinal cancer patients (4382, 4214, and 4422) using cell surface markers. Cells expressing CD8$^+$CD45RO$^+$ CD45RA$^-$HLA-DR$^+$ and either CD39$^+$ or CD103$^+$ or CD39$^+$CD103$^+$ were mixed with bulk CD8$^+$ cells in a known ratio. Next, cells were submitted for single-cell next-generation-sequencing and analyzed with the first three patients. In FIG. 10A, UMAP analysis shows that the cells clustered in 13 clusters, and previously known neoantigen-reactive T cells from 4 patients clustered predominantly in clusters 4 and 8 (FIG. 10B). The genes upregulated in clusters 4 and 8 are shown in Tables 8A (cluster 8) and 8B (cluster 4).

TABLE 8A

| Genes upregulated in cluster 8 | | | |
|---|---|---|---|
| AHNAK$^+$ | EMB$^+$ | LIMS1$^+$ | RBPJ$^+$ |
| AK4$^+$ | ESYT1$^+$ | MAD1L1$^+$ | RCSD1$^+$ |
| ALOX5AP$^+$ | FLNA$^+$ | MAP2K2$^+$ | RNPEPL1$^+$ |
| ANXA2$^+$ | GPR171$^+$ | MAP4K1$^+$ | S1PR4$^+$ |
| ANXA5$^+$ | GYG1$^+$ | MBD2$^+$ | SH2D1A$^+$ |
| ANXA6$^+$ | GZMA$^+$ | MED15$^+$ | SH3KBP1$^+$ |
| ARL6IP1$^+$ | GZMK$^+$ | MIS18BP1$^+$ | SHMT2$^+$ |

TABLE 8A-continued

| Genes upregulated in cluster 8 | | | |
|---|---|---|---|
| ARPC4$^+$ | H1FX$^+$ | MKNK2$^+$ | SIT1$^+$ |
| ATP2B4$^+$ | HACD4$^+$ | MXD4$^+$ | SLC16A3$^+$ |
| BIN1$^+$ | HIST1H1C$^+$ | MYADM$^+$ | SLC2A4RG$^+$ |
| BRI3$^+$ | HLA-DMA$^+$ | MYO1F$^+$ | SLC4A7$^+$ |
| C12orf75$^+$ | HLA-DPA1$^+$ | MYO1G$^+$ | SLF1$^+$ |
| CALHM2$^+$ | HLA-DPB1$^+$ | NCK2$^+$ | SPN$^+$ |
| CAPN2$^+$ | HLA-DQB1$^+$ | NDUFA7$^+$ | STK24$^+$ |
| CAPNS1$^+$ | HLA-DRA$^+$ | NFATC2$^+$ | TC2N$^+$ |
| CARHSP1$^+$ | HLA-DRB1$^+$ | OPTN$^+$ | TEX264$^+$ |
| CD74$^+$ | HLA-DRB5$^+$ | OSBPL8$^+$ | TGFB1$^+$ |
| CD81$^+$ | ICAM3$^+$ | P2RY8$^+$ | TIGIT$^+$ |
| CDC25B$^+$ | IDH2$^+$ | PAG1$^+$ | TLN1$^+$ |
| CDCA7$^+$ | IFI27L2$^+$ | PARP1$^+$ | TMC8$^+$ |
| CLDND1$^+$ | INPP5D$^+$ | PASK$^+$ | TMX4$^+$ |
| CNN2$^+$ | IQGAP2$^+$ | PHACTR2$^+$ | TOX$^+$ |
| COTL1$^+$ | ITGAL$^+$ | PRDX3$^+$ | TPM4$^+$ |
| CRIP1$^+$ | ITGB1$^+$ | PREX1$^+$ | TRAPPC5$^+$ |
| CXCR3$^+$ | ITGB7$^+$ | PRKCB$^+$ | TXN$^+$ |
| CYTOR$^+$ | ITM2A$^+$ | PSD4$^+$ | UBXN11$^+$ |
| DOK2$^+$ | JPT1$^+$ | PSMA2$^+$ | UCP2$^+$ |
| DYNLL1$^+$ | LAG3$^+$ | PYCARD$^+$ | VOPP1$^+$ |
| EIF3A$^+$ | LGALS1$^+$ | RAD23B$^+$ | WNK1$^+$ |
| ELOVL5$^+$ | LGALS3$^+$ | RASA3$^+$ | YWHAE$^+$ |
| | LIME1$^+$ | RBM38$^+$ | YWHAQ$^+$ |

TABLE 8B

| Genes upregulated in cluster 4 | | | |
|---|---|---|---|
| ALOX5AP$^+$ | GATA3$^+$ | P2RY10$^+$ | S1PR1$^+$ |
| ARID5B$^+$ | GPR183$^+$ | PASK$^+$ | S1PR4$^+$ |
| CCR4$^+$ | ICAM2$^+$ | PLP2$^+$ | SAMHD1$^+$ |
| CD55$^+$ | IL7R$^+$ | PPP2R5C$^+$ | SAMSN1$^+$ |
| CDKN1B$^+$ | ISG20$^+$ | PRKX$^+$ | SELL$^+$ |
| COTL1$^+$ | ITGB1$^+$ | RALA$^+$ | SESN3$^+$ |
| CREM$^+$ | ITM2A$^+$ | RASA3$^+$ | SETD2$^+$ |
| DCXR$^+$ | LEF1$^+$ | RCAN3$^+$ | SMCHD1$^+$ |
| DGKA$^+$ | LEPROTL1$^+$ | RHBDD2$^+$ | TMEM123$^+$ |
| ELOVL5$^+$ | LTB$^+$ | RNASET2$^+$ | TRAT1$^+$ |
| EML4$^+$ | NR3C1$^+$ | S100A11$^+$ | ZFP36$^+$ |
| EZR$^+$ | | | |

Cells that showed reactivity against EBV, Flu, and a pool of peptides derived from CMV or EBV or Flu (CEFx) were projected on the UMAP space in FIG. 10B. To test the gene-signature that was developed from samples of 3 patients (4246, 4317, and 4287) (Tables 4A-4B), the top 90th percentile of those cells exhibiting the closest gene expression profile to that identified in Tables 4A-4B were projected on the UMAP and highlighted clusters 4 and 8 (FIG. 10C).

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing an enriched population of T cells having antigenic specificity for a target antigen, the method comprising:

isolating T cells from a blood sample of a patient;

selecting the isolated T cells which have a gene expression profile; and separating the selected T cells from the unselected cells, wherein the separated selected T cells provide an enriched population of T cells having antigenic specificity for the target antigen, wherein the target antigen is a neoantigen encoded by a cancer-specific mutation, a cancer antigen, or a cancer-associated viral antigen, and wherein:

(a) the gene expression profile comprises all of ACTG1$^+$, AES$^+$, ANXA2$^+$, ANXA5$^+$, ARPC2$^+$, ARPC3$^+$, CD3D$^+$, CD52$^+$, CD7$^+$, CD62L$^+$, CD99$^+$, CORO1A$^+$, COTL1$^+$, CRIP1$^+$, CXCL13$^+$, EMP3$^+$, FLNA$^+$, FTL$^+$, FYB1$^+$, GAPDH$^+$, H2AFV$^+$, HMGB2$^+$, IL32$^+$, ITGB1$^+$, LSP1$^+$, LTB$^+$, PPIA$^+$, S100A10$^+$, S100A4$^+$, S100A6$^+$, SLC25A5$^+$, SUB1$^+$, TIGIT$^+$, TMSB10$^+$, VIM$^+$, ACTB$^-$, B2M$^-$, BTG1$^-$, CCL4$^-$, CCL4L2$^-$, CCL5$^-$, CD74$^-$, EEF1A1$^-$, FTH1$^-$, GZMK$^-$, HLA-DRA$^-$, MTRNR2L12$^-$, PNRC1$^-$, RPL10$^-$, RPL13$^-$, RPL3$^-$, RPL30$^-$, RPL32$^-$, RPL34$^-$, RPLP1$^-$, RPL39$^-$, RPL5$^-$, RPLP0$^-$, RPS12$^-$, RPS14$^-$, RPS18$^-$, RPS19$^-$, RPS21$^-$, RPS23$^-$, RPS24$^-$, RPS3$^-$, RPS3A$^-$, RPS4X$^-$, RPS6$^-$, and ZC3HAV1$^-$;

(b) the gene expression profile comprises all of CARS$^+$, CD39$^+$ (ENTPD1)$^+$, CD62L$^+$, CD70$^+$, CD82$^+$, CXCL13$^+$, HLA-DRB1$^+$, ITGAE$^+$, LGALS3$^+$, SA100A4$^+$, TIGIT$^+$, and TOX$^+$;

(c) the gene expression profile comprises CD8+ and all of ALOX5AP$^+$, ANXA2$^+$, ANXA5$^+$, CARS$^+$, CD82$^+$, CDC25B$^+$, CHN1$^+$, CLECL1$^+$, COTL1$^+$, CYTOR$^+$, FLNA$^+$, GATA3$^+$, HLA-DPA1$^+$, HLA-DQA2$^+$, HLA-DQB1$^+$, HLA-DRA$^+$, HLA-DRB1$^+$, HLA-DRB5$^+$, ITGB1$^+$, ITM2A$^+$, LGALS3$^+$, LIME1$^+$, MYO1G$^+$, P2RY8$^+$, PASK$^+$, RBPJ$^+$, S100A11$^+$, TIGIT$^+$, TPM4$^+$, TRADD$^+$, UBXN11$^+$, CCL4$^-$, CCL5$^-$, CCR7$^-$, CYTIP$^-$, EEF1G$^-$, GZMH$^-$, IMPDH2$^-$, LINCO2446$^-$, LYAR$^-$, MYC$^-$, NKG7$^-$, NUCB2$^-$, PITPNC1$^-$, PLAC8$^-$, and TCF7$^-$;

(d) the gene expression profile comprises CD8$^+$ and all of ALOX5AP$^+$, ANXA2$^+$, ANXA5$^+$, CARS$^+$, CD82$^+$, CDC25B$^+$, CHN1$^+$, CLECL1$^+$, COTL1$^+$, FLNA$^+$, HLA-DPA1$^+$, HLA-DQA2$^+$, HLA-DQB1$^+$, HLA-DRA$^+$, HLA-DRB1$^+$, HLA-DRB5$^+$, ITGB1$^+$, ITM2A$^+$, LGALS3$^+$, LIME1$^+$, MYO1G$^+$, PASK$^+$, S100A11$^+$, TIGIT$^+$, and UBXN11$^+$;

(e) the gene expression profile comprises CD8$^+$ and all of CD45RO$^+$, CD45RA$^-$, HLA-DR$^+$, CD39$^+$, and CD103$^+$;

(f) the gene expression profile comprises CD8$^+$ and all of CD45RO$^+$, CD45RA$^-$, HLA-DR$^+$, CD39$^+$, and TIGIT$^+$;

(g) the gene expression profile comprises CD8$^+$ and all of CD45RO$^+$, CD45RA$^-$, HLA-DR$^+$, CD39$^+$, and PDCD1$^+$;

(h) the gene expression profile comprises CD4$^+$ and all of CD45RO$^+$, CD45RA$^-$, HLA-DR$^+$, and CD39$^+$;

(i) the gene expression profile comprises CD4$^+$ and all of AK4$^+$, APOBEC3G$^+$, C12orf75$^+$, CCL5$^+$, CD74$^+$, CLIC1$^+$, COTL1$^+$, CST7$^+$, CXCL13$^+$, CXCR3$^+$, DUSP2$^+$, EEF1A1$^+$, F2R$^+$, GAPDH$^+$, GNLY$^+$, GZMA$^+$, GZMK$^+$, HCST$^+$, HLA-DPA1$^+$, LYAR$^+$, LYST$^+$, MRPL10$^+$, MYO1G$^+$, NKG7$^+$, PABPC1$^+$, PDCD1$^+$, PFN1$^+$, PRF1$^+$, RAB27A$^+$, RPL10$^+$, RPL11$^+$, RPL13$^+$, RPL18A$^+$, RPL19$^+$, RPL30$^+$, RPL32$^+$, RPL34$^+$, RPL8$^+$, RPL9$^+$, RPLP1$^+$, RPS12$^+$, RPS13$^+$, RPS23$^+$, RPS3A$^+$, RPS8$^+$, SARAF$^+$, SELL$^+$, TC2N$^+$, TMSB4X$^+$, and TPT1$^+$;

(j) the gene expression profile comprises CD4$^+$ and all of AC004585.1$^+$, ACTB$^+$, ACTG1$^+$, ALOX5AP$^+$, ANXA1$^+$, ANXA5$^+$, CD52$^+$, CD99$^+$, CNN2$^+$, COTL1$^+$, FAM45A$^+$, FTH1$^+$, FYB1$^+$, GAPDH$^+$, GIMAP4$^+$, GYPC$^+$, IFITM1$^+$, IFITM2$^+$, IGFBP4$^+$, ITGB1$^+$, LCP1$^+$, LIMS1$^+$, LMO4$^+$, MALAT1$^+$, MIF$^+$, MSN$^+$, MT-ND3$^+$, NDUFA12$^+$, PASK$^+$, PFN1$^+$, PGAM1$^+$, PPP2R5C$^+$, RARRES3$^+$, RILPL2$^+$, RPL30$^+$, RPL32$^+$, RPL34$^+$, RPL9$^+$, RPS13$^+$, RPS25$^+$, RPS3A$^+$, S100A11$^+$, S1PR4$^+$, SERF2$^+$, SLC25A5$^+$, SMC4$^+$, TIMP1$^+$, TMSB4X$^+$, VDAC1$^+$, and ZFP36L2$^+$;

(k) the gene expression profile comprises all of AHNAK$^+$, AK4$^+$, ALOX5AP$^+$, ANXA2$^+$, ANXA5$^+$, ANXA6$^+$, ARL6IP1$^+$, ARPC4$^+$, ATP2B4$^+$, BIN1$^+$, BRI3$^+$, C12orf75$^+$, CALHM2$^+$, CAPN2$^+$, CAPNS1$^+$, CARHSP1$^+$, CD74$^+$, CD81$^+$, CDC25B$^+$, CDCA7$^+$, CLDND1$^+$, CNN2$^+$, COTL1$^+$, CRIP1$^+$, CXCR3$^+$, CYTOR$^+$, DOK2$^+$, DYNLL1$^+$, EIF3A$^+$, ELOVL5$^+$, EMB$^+$, ESYT1$^+$, FLNA$^+$, GPR171$^+$, GYG1$^+$, GZMA$^+$, GZMK$^+$, H1FX$^+$, HACD4$^+$, HIST1H1C$^+$, HLA-DMA$^+$, HLA-DPA1$^+$, HLA-DPB1$^+$, HLA-DQB1$^+$, HLA-DRA$^+$, HLA-DRB1$^+$, HLA-DRB5$^+$, ICAM3$^+$, IDH2$^+$, IFI27L2$^+$, INPP5D$^+$, IQGAP2$^+$, ITGAL$^+$, ITGB1$^+$, ITGB7$^+$, ITM2A$^+$, JPT1$^+$, LAG3$^+$, LGALS1$^+$, LGALS3$^+$, LIME1$^+$, LIMS1$^+$, MAD1L1$^+$, MAP2K2$^+$, MAP4K1$^+$, MBD2$^+$, MED15$^+$, MIS18BP1$^+$, MKNK2$^+$, MXD4$^+$, MYADM$^+$, MYO1F$^+$, MYO1G$^+$, NCK2$^+$, NDUFA7$^+$, NFATC2$^+$, OPTN$^+$, OSBPL8$^+$, P2RY8$^+$, PAG1$^+$, PARP1$^+$, PASK$^+$, PHACTR2$^+$, PRDX3$^+$, PREX1$^+$, PRKCB$^+$, PSD4$^+$, PSMA2$^+$, PYCARD$^+$, RAD23B$^+$, RASA3$^+$, RBM38$^+$, RBPJ$^+$, RCSD1$^+$, RNPEPL1$^+$, S1PR4$^+$, SH2D1A$^+$, SH3KBP1$^+$, SHMT2$^+$, SIT1$^+$, SLC16A3$^+$, SLC2A4RG$^+$, SLC4A7$^+$, SLF1$^+$, SPN$^+$, STK24$^+$, TC2N$^+$, TEX264$^+$, TGFB1$^+$, TIGIT$^+$, TLN1$^+$, TMC8$^+$, TMX4$^+$, TOX$^+$, TPM4$^+$, TRAPPC5$^+$, TXN$^+$, UBXN11$^+$, UCP2$^+$, VOPP1$^+$, WNK1$^+$, YWHAE$^+$, and YWHAQ$^+$;

(l) the gene expression profile comprises all of ALOX5AP$^+$, ARID5B$^+$, CCR4$^+$, CD55$^+$, CDKN1B$^+$, COTL1$^+$, CREM$^+$, DCXR$^+$, DGKA$^+$, ELOVL5$^+$, EML4$^+$, EZR$^+$, GATA3$^+$, GPR183$^+$, ICAM2$^+$, IL7R$^+$, ISG20$^+$, ITGB1$^+$, ITM2A$^+$, LEF1$^+$, LEPROTL1$^+$, LTB$^+$, NR3C1$^+$, P2RY10$^+$, PASK$^+$, PLP2$^+$, PPP2R5C$^+$, PRKX$^+$, RALA$^+$, RASA3$^+$, RCAN3$^+$, RHBDD2$^+$, RNASET2$^+$, S100A11$^+$, S1PR1$^+$, S1PR4$^+$, SAMHD1$^+$, SAMSN1$^+$, SELL$^+$, SESN3$^+$, SETD2$^+$, SMCHD1$^+$, TMEM123$^+$, TRAT1$^+$, and ZFP36$^+$;

(m) the gene expression profile comprises all of ALOX5AP$^+$, ANXA2$^+$, ANXA5$^+$, ARID5B$^+$, CAPN2$^+$, CARS$^+$, CDC25B$^+$, CLDND1$^+$, COTL1$^+$, CREM$^+$, CRIP1$^+$, CXCR3$^+$, CYTOR$^+$, DCXR$^+$, EMB$^+$, FBXW5$^+$, FLNA$^+$, GATA3$^+$, HLA-DPA1$^+$, HLA-DPB1$^+$, HLA-DQB1$^+$, HLA-DRA$^+$, HLA-DRB1$^+$, HLA-DRB5$^+$, HNRNPUL1$^+$, ICAM2$^+$, IL10RA$^+$, ISG15$^+$, ISG20$^+$, ITGB1$^+$, ITGB7$^+$, ITM2A$^+$, KLF2$^+$, LGALS3$^+$, LIME1$^+$, MED15$^+$, MX1$^+$, NDUFA12$^+$, NR3C1$^+$, NSMCE1$^+$, P2RY8$^+$, PASK$^+$, PPP2R5C$^+$, RHBDD2$^+$, RNASET2$^+$, S100A11$^+$, S1PR4$^+$, SAMHD1$^+$, SAMSN1$^+$, SELPLG$^+$, SMCHD1$^+$, SPN$^+$, TIGIT$^+$, TRADD$^+$, and UBXN11$^+$;

(n) the gene expression profile comprises all of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHE1$^+$, FLNA$^+$, FYB1$^+$, GATA3$^+$, GNG2$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LIME1$^+$, LY6E$^+$, MAD1L1$^+$, MED15$^+$, MFNG$^+$, MTERF4$^+$, MX1$^+$, MYO1G$^+$, NDUFA12$^+$, NDUFB9$^+$, NELL2$^+$, NR3C1$^+$, OCIAD2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TIGIT$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, and YWHAB$^+$; or (o) the gene expression profile comprises all of ALOX5AP$^+$, ANXA2$^+$, ANXA5$^+$, APOBEC3G$^+$, ARHGEF1$^+$, ARID5B$^+$, BIN1$^+$, BIN2$^+$, C12orf75$^+$, C4orf48$^+$, CAMK4$^+$, CAPN2$^+$, CAPZB$^+$, CARD16$^+$, CARS$^+$, CCNDBP1$^+$, CD5$^+$, CD55$^+$, CD82$^+$, CDC25B$^+$, CHN1$^+$, CLECL1$^+$, CNN2$^+$, CORO1B$^+$, COTL1$^+$, CRIP1$^+$, CYTOR$^+$, DCXR$^+$, DYNLL1$^+$, DYNLT1$^+$, EID1$^+$, EIF3A$^+$, ELOVL5$^+$, EMB$^+$, ETHE1$^+$, FBXW5$^+$, FLNA$^+$, FYB1$^+$, GATA3$^+$, GNG2$^+$, GSTK1$^+$, HLA-DPA1$^+$, HLA-DPB1$^+$, HLA-DQA2$^+$, HLA-DQB1$^+$, HLA-DRA$^+$, HLA-DRB1$^+$, HLA-DRB5$^+$, HNRNPUL1$^+$, ICAM2$^+$, ICAM3$^+$, IL10RA$^+$, IRF7$^+$, ISG15$^+$, ISG20$^+$, ITGAE$^+$, ITGB1$^+$, ITGB7$^+$, ITM2A$^+$, KLF2$^+$, LGALS3$^+$, LIME1$^+$, LY6E$^+$, MAD1L1$^+$, MED15$^+$, MENG$^+$, MTERF4$^+$, MX1$^+$, MYO1G$^+$, NDUFA12$^+$, NDUFB9$^+$, NELL2$^+$, NR3C1$^+$, NUDT21$^+$, OCIAD 2$^+$, OPTN$^+$, P2RY8$^+$, PARP1$^+$, PASK$^+$, PLP2$^+$, PPP1R7$^+$, PPP2R5C$^+$, PSMB2$^+$, PSTPIP1$^+$, PYCARD$^+$, RBPJ$^+$, RHBDD2$^+$, RNASEH2B$^+$, RNASET2$^+$, S100A11$^+$, S100A4$^+$, S1PR4$^+$, SAMSN1$^+$, SELPLG$^+$, SH3KBP1$^+$, SHMT2$^+$, SIT1$^+$, SMCHD1$^+$, SPN$^+$, STK38$^+$, SYTL1$^+$, SYTL3$^+$, TAGAP$^+$, TBC1D10C$^+$, TGFB1$^+$, TIGIT$^+$, TMPO$^+$, TMX4$^+$, TPGS1$^+$, TPM4$^+$, TRADD$^+$, TSPO$^+$, TXN$^+$, UBE2L6$^+$, UBXN11$^+$, UCP2$^+$, YWHAB$^+$, ANKRD12$^-$, APMAP$^-$, CCL4$^-$, CCL5$^-$, CCR7$^-$, CD48$^-$, CD8B$^-$, CXCR4$^-$, CYTIP$^-$, DARS$^-$, EEF1B2$^-$, EEF1G$^-$, GZMH$^-$, HSP90AB1$^-$, IMPDH2$^-$, ISCU$^-$, LBH$^-$, LINCO2446$^-$, LYAR$^-$, MGST3$^-$, MT-ND2$^-$, MT-ND5$^-$, MYC$^-$, NDUFV2$^-$, NFKBIA$^-$, NKG7$^-$, NUCB2$^-$, PDCD4$^-$, PITPNC1$^-$, PLAC8$^-$, PRF1$^-$, PRMT2$^-$, RPL17$^-$, RPS17$^-$, SNHG7$^-$, SNHG8$^-$, STK17A$^-$, TCF7$^-$, TOMM7$^-$, WSB1$^-$, and ZFAS1$^-$.

2. The method of claim 1, wherein the gene expression profile further comprises one or both of HAVCR2$^+$ (TIM3)$^+$ and PDCD1$^+$ (PD1$^+$).

3. The method of claim 1, wherein the blood sample is from a patient who has not been treated with T cell therapy.

4. The method of claim 1, wherein isolating T cells from the blood sample of the patient comprises isolating CD8$^+$ T cells from the blood sample.

5. The method of claim 1, wherein isolating T cells from the blood sample of the patient comprises isolating CD4$^+$ T cells from the blood sample.

6. The method of claim 1, wherein the method does not require identifying any HLA molecules expressed by the patient.

7. The method of claim 1, wherein selecting the isolated T cells which have a gene expression profile comprises:

(i) detecting the presence of protein(s) encoded by positively expressed gene(s) of the gene expression profile;

(ii) detecting the absence of protein(s) encoded by gene(s) that are negative for expression in the gene expression profile;

(iii) measuring the quantity of protein(s) encoded by gene(s) that are negative for expression in the gene expression profile; and/or (iv) measuring the quantity of protein(s) encoded by gene(s) that are positive for expression in the gene expression profile.

8. The method of claim 1, wherein selecting the isolated T cells which have a gene expression profile comprises:

(i) detecting the presence of RNA encoded by positively expressed gene(s) of the gene expression profile;

(ii) detecting the absence of RNA encoded by gene(s) that are negative for expression in the gene expression profile;

(iii) measuring the quantity of RNA encoded by gene(s) that are negative for expression in the gene expression profile; and/or (iv) measuring the quantity of RNA encoded by gene(s) that are positive for expression in the gene expression profile.

9. The method of claim 1, wherein selecting the isolated T cells which have a gene expression profile comprises carrying out one or more single cell dimensional reduction methods.

10. The method of claim 1, wherein selecting the isolated T cells which have a gene expression profile comprises carrying out cellular indexing of transcriptomes analysis.

11. The method of claim 1, wherein selecting the isolated T cells which have a gene expression profile comprises carrying out cellular indexing of transcriptomes and epitopes by sequencing analysis.

12. The method of claim 1, wherein selecting the isolated T cells which have a gene expression profile comprises carrying out single cell transcriptome analysis.

13. The method of claim 1, wherein the method comprises (a).

14. The method of claim 1, wherein the method comprises (b).

15. The method of claim 1, wherein the method comprises (i) or (j) and the gene expression profile further comprises one or both of $CD25^-$ and $CD127^-$.

16. The method of claim 1, wherein the cancer-associated viral antigen is a human papillomavirus (HPV) antigen or an Epstein-Barr virus (EBV) antigen.

17. A method of isolating a T cell receptor (TCR), or an antigen-binding portion thereof, having antigenic specificity for a target antigen, the method comprising:

preparing an enriched population of T cells having antigenic specificity for the target antigen according to the method of claim 1;

sorting the T cells in the enriched population into separate single T cell samples;

sequencing TCR complementarity determining regions 3 (CDR3) in one or more of the separate single T cell samples;

pairing an alpha chain variable region comprising a CDR3 with a beta chain variable region comprising a CDR3 encoded by the nucleic acid of the separate single T cell samples;

introducing a nucleotide sequence encoding the paired alpha chain variable region and beta chain variable region into host cells and expressing the paired alpha chain variable region and beta chain variable region by the host cells;

screening the host cells expressing the paired alpha chain variable region and beta chain variable region for antigenic specificity for the target antigen; and selecting the paired alpha chain variable region and beta chain variable region that have antigenic specificity for the target antigen, wherein the TCR, or an antigen-binding portion thereof, having antigenic specificity for the target antigen is isolated.

18. A method of preparing a population of cells that express a TCR, or an antigen-binding portion thereof, having antigenic specificity for a target antigen, the method comprising:

isolating a TCR, or an antigen-binding portion thereof, according to the method of claim 17, and introducing a nucleotide sequence encoding the isolated TCR, or the antigen-binding portion thereof, into peripheral blood mononuclear cells (PBMC) to obtain cells that express the TCR, or the antigen-binding portion thereof.

19. The method of claim 18, further comprising expanding the numbers of PBMC that express the TCR, or the antigen-binding portion thereof.

20. A method of treating a condition in a mammal, the method comprising:

preparing an enriched population of T cells having antigenic specificity for a target antigen according to the method of claim 1; and administering the enriched population of T cells to the mammal in an amount effective to treat the condition in the mammal, wherein the condition is cancer or a viral condition.

* * * * *